(12) United States Patent
Perrin

(10) Patent No.: US 11,234,813 B2
(45) Date of Patent: Feb. 1, 2022

(54) VENTRICULAR STABILITY ELEMENTS FOR SIDE-DELIVERABLE PROSTHETIC HEART VALVES AND METHODS OF DELIVERY

(71) Applicant: VDyne, Inc., Maple Grove, MN (US)

(72) Inventor: Chad Perrin, Andover, MN (US)

(73) Assignee: VDyne, Inc., Maple Grove, MN (US)

( * ) Notice: Subject to any disclaimer, the term of this patent is extended or adjusted under 35 U.S.C. 154(b) by 0 days.

(21) Appl. No.: 17/154,438

(22) Filed: Jan. 21, 2021

(65) Prior Publication Data

US 2021/0220126 A1   Jul. 22, 2021

Related U.S. Application Data

(63) Continuation of application No. PCT/US2021/013570, filed on Jan. 15, 2021.
(Continued)

(51) Int. Cl.
*A61F 2/24* (2006.01)

(52) U.S. Cl.
CPC .......... *A61F 2/2418* (2013.01); *A61F 2/2433* (2013.01)

(58) Field of Classification Search
CPC .. A61F 2/24; A61F 2/2418; A61F 2250/0039; A61F 2/2412; A61F 2/246;
(Continued)

(56) References Cited

U.S. PATENT DOCUMENTS

| 3,744,060 A | 7/1973 | Bellhouse et al. |
|---|---|---|
| 4,079,468 A | 3/1978 | Liotta et al. |
| (Continued) | | |

FOREIGN PATENT DOCUMENTS

| AU | 2006203686 B2 | 11/2008 |
|---|---|---|
| AU | 2009219415 A1 | 9/2009 |
| (Continued) | | |

OTHER PUBLICATIONS

Office Action for U.S. Appl. No. 16/435,687, dated Aug. 7, 2019, 19 pages.
(Continued)

*Primary Examiner* — Seema Mathew
(74) *Attorney, Agent, or Firm* — Cooley LLP

(57) ABSTRACT

A side-deliverable prosthetic heart valve includes a valve frame defining an aperture that extends along a central axis and a flow control component mounted within the aperture and configured to permit selective blood flow therethrough. The prosthetic heart valve has a compressed configuration for side-delivery to a heart of a patient via a delivery catheter. The prosthetic heart valve is configured to transition to an expanded configuration when released from the delivery catheter for seating in a native annulus. The valve frame includes distal, proximal, and septal anchoring elements, each of which is insertable through the native annulus prior to seating the prosthetic heart valve therein. The septal anchoring element is configured to extend below the annulus and contact ventricular septal tissue to stabilize the prosthetic heart valve in the annulus when the prosthetic heart valve is seated in the annulus.

27 Claims, 12 Drawing Sheets

Related U.S. Application Data

(60) Provisional application No. 62/962,902, filed on Jan. 17, 2020.

(58) Field of Classification Search
CPC ........ A61F 2002/068; A61F 2/07; A61F 2/06; A61F 2/2409
See application file for complete search history.

(56) References Cited

U.S. PATENT DOCUMENTS

| | | |
|---|---|---|
| 5,397,351 A | 3/1995 | Pavcnik et al. |
| 5,509,428 A | 4/1996 | Dunlop |
| 5,554,185 A | 9/1996 | Block et al. |
| 6,006,134 A | 12/1999 | Hill et al. |
| 6,197,013 B1 | 3/2001 | Reed et al. |
| 6,290,719 B1 | 9/2001 | Garberoglio |
| 6,449,507 B1 | 9/2002 | Hill et al. |
| 6,458,153 B1 | 10/2002 | Bailey et al. |
| 6,532,388 B1 | 3/2003 | Hill et al. |
| 6,582,467 B1 | 6/2003 | Teitelbaum et al. |
| 6,628,987 B1 | 9/2003 | Hill et al. |
| 6,669,724 B2 | 12/2003 | Park et al. |
| 6,718,208 B2 | 4/2004 | Hill et al. |
| 6,769,434 B2 | 8/2004 | Liddicoat et al. |
| 6,890,330 B2 | 5/2005 | Streeter et al. |
| 6,896,690 B1 | 5/2005 | Lambrecht et al. |
| 6,904,318 B2 | 6/2005 | Hill et al. |
| 6,929,653 B2 | 8/2005 | Streeter |
| 7,074,189 B1 | 7/2006 | Montegrande |
| 7,125,418 B2 | 10/2006 | Duran et al. |
| 7,175,660 B2 | 2/2007 | Cartledge et al. |
| 7,201,761 B2 | 4/2007 | Woolfson et al. |
| 7,225,019 B2 | 5/2007 | Jahns et al. |
| 7,269,457 B2 | 9/2007 | Shafer et al. |
| 7,331,991 B2 | 2/2008 | Kheradvar et al. |
| 7,361,189 B2 | 4/2008 | Case et al. |
| 7,374,571 B2 | 5/2008 | Pease et al. |
| 7,442,204 B2 | 10/2008 | Schwammenthal et al. |
| 7,449,027 B2 | 11/2008 | Hunt et al. |
| 7,621,948 B2 | 11/2009 | Herrmann et al. |
| 7,648,527 B2 | 1/2010 | Agnew |
| 7,717,952 B2 | 5/2010 | Case et al. |
| 7,749,245 B2 | 7/2010 | Cohn et al. |
| 7,753,949 B2 | 7/2010 | Lamphere et al. |
| 7,811,316 B2 | 10/2010 | Kalmann et al. |
| 7,828,840 B2 | 11/2010 | Biggs et al. |
| 7,846,199 B2 | 12/2010 | Paul, Jr. et al. |
| 8,303,648 B2 | 11/2012 | Grewe et al. |
| 8,366,768 B2 | 2/2013 | Zhang |
| 8,491,650 B2 | 7/2013 | Wiemeyer et al. |
| 8,568,474 B2 | 10/2013 | Yeung et al. |
| 8,628,571 B1 | 1/2014 | Hacohen et al. |
| 8,641,752 B1 | 2/2014 | Holm et al. |
| 8,696,743 B2 | 4/2014 | Holecek et al. |
| 8,728,153 B2 | 5/2014 | Bishop et al. |
| 8,758,395 B2 | 6/2014 | Kleshinski et al. |
| 8,846,390 B2 | 9/2014 | Dove et al. |
| 8,876,892 B2 | 11/2014 | Tran et al. |
| 8,900,295 B2 | 12/2014 | Migliazza et al. |
| 8,915,958 B2 | 12/2014 | Braido |
| 8,926,690 B2 | 1/2015 | Kovalsky |
| 8,926,692 B2 | 1/2015 | Dwork |
| 8,926,694 B2 | 1/2015 | Costello |
| 8,940,044 B2 | 1/2015 | Hammer et al. |
| 8,956,404 B2 | 2/2015 | Bortlein et al. |
| 8,986,370 B2 | 3/2015 | Annest |
| 9,011,524 B2 | 4/2015 | Eberhardt |
| 9,017,399 B2 | 4/2015 | Gross et al. |
| 9,050,188 B2 | 6/2015 | Schweich, Jr. et al. |
| 9,072,604 B1 | 7/2015 | Melnick et al. |
| 9,119,714 B2 | 9/2015 | Shandas et al. |
| 9,216,076 B2 | 12/2015 | Mitra et al. |
| 9,232,995 B2 | 1/2016 | Kovalsky et al. |
| 9,241,792 B2 | 1/2016 | Benichou et al. |
| 9,248,016 B2 | 2/2016 | Oba et al. |
| 9,259,215 B2 | 2/2016 | Chou et al. |
| 9,277,990 B2 | 3/2016 | Klima et al. |
| 9,289,282 B2 | 3/2016 | Olson et al. |
| 9,289,296 B2 | 3/2016 | Braido et al. |
| 9,295,547 B2 | 3/2016 | Costello et al. |
| 9,301,839 B2 | 4/2016 | Stante et al. |
| 9,308,086 B2 | 4/2016 | Ho |
| 9,339,367 B2 | 5/2016 | Carpenter et al. |
| 9,370,418 B2 | 6/2016 | Pintor et al. |
| 9,381,083 B2 | 7/2016 | Costello |
| 9,387,075 B2 | 7/2016 | Bortlein et al. |
| 9,393,111 B2 | 7/2016 | Ma et al. |
| 9,414,915 B2 | 8/2016 | Lombardi et al. |
| 9,433,500 B2 | 9/2016 | Chau et al. |
| 9,440,054 B2 | 9/2016 | Bishop et al. |
| 9,456,899 B2 | 10/2016 | Yeung et al. |
| 9,468,525 B2 | 10/2016 | Kovalsky et al. |
| 9,474,604 B2 | 10/2016 | Centola et al. |
| 9,486,306 B2 | 11/2016 | Tegels et al. |
| 9,510,941 B2 | 12/2016 | Bishop et al. |
| 9,554,902 B2 | 1/2017 | Braido et al. |
| 9,579,196 B2 | 2/2017 | Morriss et al. |
| 9,579,200 B2 | 2/2017 | Lederman et al. |
| 9,597,181 B2 * | 3/2017 | Christianson ......... A61F 2/2463 |
| 9,610,159 B2 | 4/2017 | Christianson et al. |
| 9,615,925 B2 | 4/2017 | Subramanian et al. |
| 9,629,719 B2 | 4/2017 | Rothstein |
| 9,636,222 B2 | 5/2017 | Oslund |
| 9,649,191 B2 | 5/2017 | Savage et al. |
| 9,662,202 B2 | 5/2017 | Quill et al. |
| 9,662,203 B2 | 5/2017 | Sheahan et al. |
| 9,662,209 B2 | 5/2017 | Gross et al. |
| 9,675,454 B2 | 6/2017 | Vidlund et al. |
| 9,675,485 B2 | 6/2017 | Essinger et al. |
| 9,687,343 B2 | 6/2017 | Bortlein et al. |
| 9,707,076 B2 | 7/2017 | Stack et al. |
| 9,713,530 B2 | 7/2017 | Cabiri et al. |
| 9,750,607 B2 | 9/2017 | Ganesan et al. |
| 9,763,778 B2 | 9/2017 | Eidenschink et al. |
| 9,763,779 B2 | 9/2017 | Bortlein et al. |
| 9,788,946 B2 | 10/2017 | Bobo, Jr. et al. |
| 9,839,511 B2 | 12/2017 | Ma et al. |
| 9,849,011 B2 | 12/2017 | Zimmerman et al. |
| 9,855,384 B2 | 1/2018 | Cohen et al. |
| 9,861,464 B2 | 1/2018 | Azimpour et al. |
| 9,895,219 B2 | 2/2018 | Costello et al. |
| 9,901,330 B2 | 2/2018 | Akpinar |
| 9,918,838 B2 | 3/2018 | Ring |
| 9,943,409 B2 | 4/2018 | Kim et al. |
| 9,949,825 B2 | 4/2018 | Braido et al. |
| 9,968,444 B2 | 5/2018 | Millwee et al. |
| 9,968,445 B2 | 5/2018 | Kheradvar |
| 9,980,815 B2 | 5/2018 | Nitzan et al. |
| 9,987,121 B2 | 6/2018 | Blanzy |
| 10,010,411 B2 | 7/2018 | Peter |
| 10,010,412 B2 | 7/2018 | Taft et al. |
| 10,022,054 B2 | 7/2018 | Najafi et al. |
| 10,022,222 B2 | 7/2018 | Groothuis et al. |
| 10,022,223 B2 | 7/2018 | Bruchman |
| 10,028,821 B2 | 7/2018 | Centola et al. |
| 10,028,831 B2 | 7/2018 | Morin et al. |
| 10,034,667 B2 | 7/2018 | Morris et al. |
| 10,034,747 B2 | 7/2018 | Harewood |
| 10,039,638 B2 | 8/2018 | Bruchman et al. |
| 10,058,315 B2 | 8/2018 | Rafiee et al. |
| 10,058,411 B2 | 8/2018 | Fifer et al. |
| 10,058,421 B2 | 8/2018 | Eberhardt et al. |
| 10,058,426 B2 | 8/2018 | Barbarino |
| 10,064,405 B2 | 9/2018 | Dale et al. |
| 10,080,653 B2 | 9/2018 | Conklin et al. |
| 10,085,835 B2 | 10/2018 | Thambar et al. |
| 10,105,224 B2 | 10/2018 | Buchbinder et al. |
| 10,117,741 B2 | 11/2018 | Schweich, Jr. et al. |
| 10,123,874 B2 | 11/2018 | Khairkhahan et al. |
| 10,130,331 B2 | 11/2018 | Stigall et al. |
| 10,130,467 B2 | 11/2018 | Braido et al. |
| 10,149,685 B2 | 12/2018 | Kizuka |
| 10,154,905 B2 | 12/2018 | Duffy |
| 10,179,043 B2 | 1/2019 | Cohen-Tzemach et al. |

(56) References Cited

U.S. PATENT DOCUMENTS

| | | |
|---|---|---|
| 10,182,908 B2 | 1/2019 | Tubishevitz et al. |
| 10,182,911 B2 | 1/2019 | Hillukka |
| 10,206,775 B2 | 2/2019 | Kovalsky et al. |
| 10,219,895 B2 | 3/2019 | Wagner et al. |
| 10,219,896 B2 | 3/2019 | Sandstrom et al. |
| 10,220,192 B2 | 3/2019 | Drasler et al. |
| 10,226,178 B2 | 3/2019 | Cohen et al. |
| 10,226,335 B2 | 3/2019 | Cartledge et al. |
| 10,245,142 B2 | 4/2019 | Bonhoeffer |
| 10,258,467 B2 | 4/2019 | Hou et al. |
| 10,265,173 B2 | 4/2019 | Griffin et al. |
| 10,321,987 B2 | 6/2019 | Wang et al. |
| 10,321,995 B1* | 6/2019 | Christianson ......... A61F 2/2409 |
| 10,327,895 B2 | 6/2019 | Lozonschi et al. |
| 10,327,899 B2 | 6/2019 | Sandstrom et al. |
| 10,329,066 B2 | 6/2019 | Kruetzfeldt et al. |
| 10,350,047 B2 | 7/2019 | Rajpara et al. |
| 10,357,361 B2 | 7/2019 | Rafi et al. |
| 10,368,989 B2 | 8/2019 | Duffy et al. |
| 10,398,550 B2 | 9/2019 | Chalekian et al. |
| 10,426,611 B2 | 10/2019 | Hariton et al. |
| 10,433,957 B2 | 10/2019 | Khouengboua et al. |
| 10,433,960 B1 | 10/2019 | Sutherland et al. |
| 10,463,489 B2 | 11/2019 | Christianson et al. |
| 10,485,976 B2 | 11/2019 | Streeter et al. |
| 10,595,994 B1 | 3/2020 | Christianson et al. |
| 10,631,983 B1* | 4/2020 | Christianson ............ A61F 2/243 |
| 10,653,522 B1* | 5/2020 | Vidlund ................ A61F 2/2433 |
| 10,758,346 B1* | 9/2020 | Christianson ......... A61F 2/2418 |
| 10,761,511 B2* | 9/2020 | Chen ..................... G06T 7/0004 |
| 10,779,937 B2* | 9/2020 | Vidlund ................ A61F 2/2427 |
| 11,071,627 B2 | 7/2021 | Saikrishnan et al. |
| 11,076,956 B2 | 8/2021 | Christianson et al. |
| 11,109,969 B2 | 9/2021 | Vidlund et al. |
| 11,166,814 B2* | 11/2021 | Vidlund, I ............. A61F 2/9522 |
| 11,173,027 B2* | 11/2021 | Christianson ......... A61F 2/2436 |
| 2003/0040772 A1 | 2/2003 | Hyodoh et al. |
| 2003/0040808 A1 | 2/2003 | Stack et al. |
| 2003/0153901 A1 | 8/2003 | Herweck et al. |
| 2003/0166990 A1 | 9/2003 | Trauthen et al. |
| 2003/0171801 A1 | 9/2003 | Bates |
| 2004/0049207 A1 | 3/2004 | Goldfarb et al. |
| 2004/0088047 A1 | 5/2004 | Spence et al. |
| 2004/0093060 A1 | 5/2004 | Seguin et al. |
| 2004/0116996 A1 | 6/2004 | Freitag |
| 2004/0199209 A1 | 10/2004 | Hill et al. |
| 2004/0225352 A1 | 11/2004 | Osborne et al. |
| 2005/0010246 A1 | 1/2005 | Streeter et al. |
| 2005/0075659 A1 | 4/2005 | Realyvasquez et al. |
| 2005/0075725 A1 | 4/2005 | Rowe |
| 2005/0107811 A1 | 5/2005 | Starksen et al. |
| 2005/0137686 A1 | 6/2005 | Salahieh et al. |
| 2005/0228495 A1 | 10/2005 | Macoviak |
| 2006/0015167 A1 | 1/2006 | Armstrong et al. |
| 2006/0190075 A1 | 8/2006 | Jordan et al. |
| 2006/0195180 A1 | 8/2006 | Kheradvar et al. |
| 2006/0229708 A1 | 10/2006 | Powell et al. |
| 2006/0241745 A1 | 10/2006 | Solem |
| 2006/0271098 A1 | 11/2006 | Peacock, III |
| 2006/0276887 A1 | 12/2006 | Brady et al. |
| 2007/0016286 A1 | 1/2007 | Herrmann et al. |
| 2007/0027535 A1 | 2/2007 | Purdy et al. |
| 2007/0032850 A1 | 2/2007 | Ruiz et al. |
| 2007/0038295 A1 | 2/2007 | Case et al. |
| 2007/0100427 A1 | 5/2007 | Perouse |
| 2007/0162102 A1 | 7/2007 | Ryan et al. |
| 2007/0208417 A1 | 9/2007 | Agnew |
| 2007/0213805 A1 | 9/2007 | Schaeffer et al. |
| 2007/0233176 A1 | 10/2007 | Gilson et al. |
| 2007/0233228 A1 | 10/2007 | Eberhardt et al. |
| 2007/0239271 A1 | 10/2007 | Nguyen |
| 2007/0288087 A1 | 12/2007 | Fearnot et al. |
| 2008/0004686 A1 | 1/2008 | Hunt et al. |
| 2008/0020013 A1 | 1/2008 | Reyes et al. |
| 2008/0065204 A1 | 3/2008 | Macoviak et al. |
| 2008/0071287 A1 | 3/2008 | Goto |
| 2008/0132999 A1 | 6/2008 | Mericle et al. |
| 2008/0140181 A1 | 6/2008 | Reynolds et al. |
| 2008/0154355 A1 | 6/2008 | Benichou et al. |
| 2008/0183279 A1 | 7/2008 | Bailey et al. |
| 2008/0200977 A1 | 8/2008 | Paul et al. |
| 2008/0200980 A1 | 8/2008 | Robin et al. |
| 2008/0208332 A1 | 8/2008 | Lamphere et al. |
| 2008/0221672 A1 | 9/2008 | Lamphere et al. |
| 2008/0262592 A1 | 10/2008 | Jordan et al. |
| 2008/0262609 A1 | 10/2008 | Gross et al. |
| 2008/0275550 A1 | 11/2008 | Kheradvar et al. |
| 2009/0005863 A1 | 1/2009 | Goetz et al. |
| 2009/0054976 A1 | 2/2009 | Tuval et al. |
| 2009/0094189 A1 | 4/2009 | Stephens |
| 2009/0192586 A1 | 7/2009 | Tabor et al. |
| 2009/0254174 A1 | 10/2009 | Case et al. |
| 2009/0264991 A1 | 10/2009 | Paul, Jr. et al. |
| 2009/0287290 A1 | 11/2009 | Macaulay et al. |
| 2010/0049294 A1 | 2/2010 | Zukowski et al. |
| 2010/0049313 A1 | 2/2010 | Alon et al. |
| 2010/0121434 A1 | 5/2010 | Paul et al. |
| 2010/0160773 A1 | 6/2010 | Cohen et al. |
| 2010/0161043 A1 | 6/2010 | Maisano et al. |
| 2010/0168844 A1 | 7/2010 | Toomes et al. |
| 2010/0174363 A1 | 7/2010 | Castro |
| 2010/0179583 A1 | 7/2010 | Carpenter et al. |
| 2010/0179584 A1 | 7/2010 | Carpenter et al. |
| 2010/0179647 A1 | 7/2010 | Carpenter et al. |
| 2010/0280591 A1 | 11/2010 | Shin et al. |
| 2010/0298929 A1 | 11/2010 | Thornton et al. |
| 2010/0305685 A1 | 12/2010 | Millwee et al. |
| 2011/0004237 A1 | 1/2011 | Schneider et al. |
| 2011/0029071 A1 | 2/2011 | Zlotnick et al. |
| 2011/0029072 A1 | 2/2011 | Gabbay |
| 2011/0066233 A1 | 3/2011 | Thornton et al. |
| 2011/0071613 A1 | 3/2011 | Wood et al. |
| 2011/0098804 A1 | 4/2011 | Yeung et al. |
| 2011/0125145 A1 | 5/2011 | Mody et al. |
| 2011/0137397 A1 | 6/2011 | Chau et al. |
| 2011/0160836 A1 | 6/2011 | Behan |
| 2011/0172764 A1 | 7/2011 | Badhwar |
| 2011/0224785 A1 | 9/2011 | Hacohen et al. |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0257721 A1 | 10/2011 | Tabor |
| 2011/0264191 A1 | 10/2011 | Rothstein |
| 2012/0022605 A1 | 1/2012 | Jahns et al. |
| 2012/0022633 A1 | 1/2012 | Olson et al. |
| 2012/0022639 A1 | 1/2012 | Hacohen et al. |
| 2012/0022640 A1 | 1/2012 | Gross et al. |
| 2012/0022644 A1 | 1/2012 | Reich et al. |
| 2012/0035701 A1 | 2/2012 | To |
| 2012/0065723 A1 | 3/2012 | Drasler et al. |
| 2012/0083874 A1 | 4/2012 | Dale et al. |
| 2012/0123531 A1 | 5/2012 | Tsukashima et al. |
| 2012/0137521 A1 | 6/2012 | Millwee et al. |
| 2012/0165928 A1 | 6/2012 | Nitzan et al. |
| 2012/0172981 A1 | 7/2012 | DuMontelle |
| 2012/0203336 A1 | 8/2012 | Annest |
| 2012/0209375 A1 | 8/2012 | Madrid et al. |
| 2012/0232574 A1 | 9/2012 | Kim et al. |
| 2012/0277853 A1 | 11/2012 | Rothstein |
| 2012/0310327 A1 | 12/2012 | McHugo |
| 2012/0310328 A1 | 12/2012 | Olson et al. |
| 2013/0035759 A1 | 2/2013 | Gross et al. |
| 2013/0055941 A1 | 3/2013 | Holecek et al. |
| 2013/0131714 A1 | 5/2013 | Wang et al. |
| 2013/0131792 A1 | 5/2013 | Miller et al. |
| 2013/0166017 A1 | 6/2013 | Cartledge et al. |
| 2013/0184742 A1 | 7/2013 | Ganesan et al. |
| 2013/0190857 A1 | 7/2013 | Mitra et al. |
| 2013/0190861 A1 | 7/2013 | Chau et al. |
| 2013/0197621 A1 | 8/2013 | Ryan et al. |
| 2013/0226289 A1 | 8/2013 | Shaolian et al. |
| 2013/0238010 A1 | 9/2013 | Johnson et al. |
| 2013/0238089 A1 | 9/2013 | Lichtenstein et al. |
| 2013/0253570 A1 | 9/2013 | Bates |

(56) References Cited

U.S. PATENT DOCUMENTS

| | | |
|---|---|---|
| 2013/0274618 A1 | 10/2013 | Hou et al. |
| 2013/0274855 A1 | 10/2013 | Stante et al. |
| 2013/0282110 A1 | 10/2013 | Schweich, Jr. et al. |
| 2013/0297010 A1 | 11/2013 | Bishop et al. |
| 2013/0304197 A1 | 11/2013 | Buchbinder et al. |
| 2013/0304200 A1 | 11/2013 | McLean et al. |
| 2013/0331929 A1 | 12/2013 | Mitra et al. |
| 2013/0338764 A1 | 12/2013 | Thornton et al. |
| 2014/0000112 A1 | 1/2014 | Braido et al. |
| 2014/0005540 A1 | 1/2014 | Merhi |
| 2014/0005768 A1 | 1/2014 | Thomas et al. |
| 2014/0005778 A1 | 1/2014 | Buchbinder et al. |
| 2014/0012372 A1 | 1/2014 | Chau et al. |
| 2014/0018915 A1 | 1/2014 | Baidillah et al. |
| 2014/0039511 A1 | 2/2014 | Morris et al. |
| 2014/0039611 A1 | 2/2014 | Lane et al. |
| 2014/0052237 A1 | 2/2014 | Lane et al. |
| 2014/0081383 A1 | 3/2014 | Eberhardt et al. |
| 2014/0088680 A1 | 3/2014 | Costello et al. |
| 2014/0107758 A1 | 4/2014 | Glazier |
| 2014/0110279 A1 | 4/2014 | Kruetzfeldt et al. |
| 2014/0114403 A1 | 4/2014 | Dale et al. |
| 2014/0121763 A1 | 5/2014 | Duffy et al. |
| 2014/0135895 A1 | 5/2014 | Andress et al. |
| 2014/0135908 A1 | 5/2014 | Glozman et al. |
| 2014/0142695 A1 | 5/2014 | Gross et al. |
| 2014/0172070 A1 | 6/2014 | Seguin |
| 2014/0180069 A1 | 6/2014 | Millett |
| 2014/0180070 A1 | 6/2014 | Millett et al. |
| 2014/0194704 A1 | 7/2014 | Millett et al. |
| 2014/0194983 A1 | 7/2014 | Kovalsky et al. |
| 2014/0207231 A1 | 7/2014 | Hacohen et al. |
| 2014/0214069 A1 | 7/2014 | Franklin |
| 2014/0214159 A1 | 7/2014 | Vidlund et al. |
| 2014/0222136 A1 | 8/2014 | Geist et al. |
| 2014/0222137 A1 | 8/2014 | Miller et al. |
| 2014/0222142 A1 | 8/2014 | Kovalsky et al. |
| 2014/0249566 A1 | 9/2014 | Quinn et al. |
| 2014/0257466 A1 | 9/2014 | Board et al. |
| 2014/0257467 A1 | 9/2014 | Lane et al. |
| 2014/0276616 A1 | 9/2014 | Smith et al. |
| 2014/0276971 A1 | 9/2014 | Kovach |
| 2014/0277342 A1 | 9/2014 | Roeder et al. |
| 2014/0277388 A1 | 9/2014 | Skemp |
| 2014/0277408 A1 | 9/2014 | Folan |
| 2014/0296962 A1 | 10/2014 | Cartledge et al. |
| 2014/0296969 A1 | 10/2014 | Tegels et al. |
| 2014/0296975 A1* | 10/2014 | Tegels ................ A61F 2/07 623/2.18 |
| 2014/0303718 A1 | 10/2014 | Tegels et al. |
| 2014/0303724 A1 | 10/2014 | Bluestein et al. |
| 2014/0309732 A1 | 10/2014 | Solem |
| 2014/0324161 A1 | 10/2014 | Tegels et al. |
| 2014/0350662 A1 | 11/2014 | Vaturi |
| 2014/0358224 A1 | 12/2014 | Tegels et al. |
| 2014/0371789 A1 | 12/2014 | Hariton et al. |
| 2014/0379076 A1 | 12/2014 | Vidlund et al. |
| 2015/0005808 A1 | 1/2015 | Chouinard et al. |
| 2015/0005874 A1 | 1/2015 | Vidlund et al. |
| 2015/0039081 A1 | 2/2015 | Costello |
| 2015/0045880 A1 | 2/2015 | Hacohen |
| 2015/0051687 A1 | 2/2015 | Dickerhoff et al. |
| 2015/0094802 A1 | 4/2015 | Buchbinder et al. |
| 2015/0112188 A1 | 4/2015 | Stigall et al. |
| 2015/0119982 A1 | 4/2015 | Quill et al. |
| 2015/0127093 A1 | 5/2015 | Hosmer et al. |
| 2015/0142103 A1 | 5/2015 | Vidlund |
| 2015/0157457 A1 | 6/2015 | Hacohen |
| 2015/0173898 A1 | 6/2015 | Drasler et al. |
| 2015/0196390 A1 | 7/2015 | Ma et al. |
| 2015/0196391 A1 | 7/2015 | Dwork |
| 2015/0202044 A1 | 7/2015 | Chau et al. |
| 2015/0216661 A1 | 8/2015 | Hacohen et al. |
| 2015/0230919 A1 | 8/2015 | Chau et al. |
| 2015/0245934 A1 | 9/2015 | Lombardi et al. |
| 2015/0257878 A1 | 9/2015 | Lane et al. |
| 2015/0257880 A1 | 9/2015 | Bortlein et al. |
| 2015/0257882 A1 | 9/2015 | Bortlein et al. |
| 2015/0265400 A1 | 9/2015 | Eidenschink et al. |
| 2015/0272731 A1 | 10/2015 | Racchini et al. |
| 2015/0282922 A1 | 10/2015 | Hingston et al. |
| 2015/0282931 A1 | 10/2015 | Brunnett et al. |
| 2015/0289971 A1 | 10/2015 | Costello et al. |
| 2015/0289975 A1 | 10/2015 | Costello |
| 2015/0297241 A1 | 10/2015 | Yodfat et al. |
| 2015/0305867 A1 | 10/2015 | Liu et al. |
| 2015/0313701 A1 | 11/2015 | Krahbichler |
| 2015/0335424 A1 | 11/2015 | McLean et al. |
| 2015/0342717 A1 | 12/2015 | O'Donnell et al. |
| 2015/0351904 A1 | 12/2015 | Cooper et al. |
| 2015/0351906 A1 | 12/2015 | Hammer et al. |
| 2015/0351910 A1 | 12/2015 | Gilmore et al. |
| 2015/0359629 A1 | 12/2015 | Ganesan et al. |
| 2016/0008130 A1 | 1/2016 | Hasin |
| 2016/0008131 A1 | 1/2016 | Christianson et al. |
| 2016/0022417 A1 | 1/2016 | Karapetian et al. |
| 2016/0030165 A1 | 2/2016 | Mitra et al. |
| 2016/0030167 A1 | 2/2016 | Delaloye et al. |
| 2016/0038280 A1 | 2/2016 | Morriss et al. |
| 2016/0038283 A1 | 2/2016 | Divekar et al. |
| 2016/0045165 A1 | 2/2016 | Braido et al. |
| 2016/0045306 A1 | 2/2016 | Agrawal et al. |
| 2016/0045309 A1 | 2/2016 | Valdez et al. |
| 2016/0067031 A1 | 3/2016 | Kassab et al. |
| 2016/0081799 A1 | 3/2016 | Leo et al. |
| 2016/0095703 A1 | 4/2016 | Thomas et al. |
| 2016/0095704 A1 | 4/2016 | Whitman |
| 2016/0113764 A1 | 4/2016 | Sheahan et al. |
| 2016/0113766 A1 | 4/2016 | Ganesan et al. |
| 2016/0113768 A1 | 4/2016 | Ganesan et al. |
| 2016/0143721 A1 | 5/2016 | Rosenbluth et al. |
| 2016/0143730 A1 | 5/2016 | Kheradvar |
| 2016/0143735 A1 | 5/2016 | Subramanian et al. |
| 2016/0143739 A1 | 5/2016 | Horgan et al. |
| 2016/0158004 A1 | 6/2016 | Kumar et al. |
| 2016/0158007 A1 | 6/2016 | Centola et al. |
| 2016/0158008 A1 | 6/2016 | Miller et al. |
| 2016/0166382 A1 | 6/2016 | Nguyen |
| 2016/0184488 A1 | 6/2016 | Toyoda et al. |
| 2016/0194425 A1 | 7/2016 | Mitra et al. |
| 2016/0213470 A1 | 7/2016 | Ahlberg et al. |
| 2016/0213473 A1 | 7/2016 | Hacohen et al. |
| 2016/0220367 A1 | 8/2016 | Barrett |
| 2016/0220372 A1 | 8/2016 | Medema et al. |
| 2016/0220734 A1 | 8/2016 | Dyamenahalli et al. |
| 2016/0228250 A1 | 8/2016 | Casley et al. |
| 2016/0235530 A1 | 8/2016 | Thomas et al. |
| 2016/0256269 A1 | 9/2016 | Cahalane et al. |
| 2016/0256270 A1 | 9/2016 | Folan et al. |
| 2016/0270911 A1 | 9/2016 | Ganesan et al. |
| 2016/0303804 A1 | 10/2016 | Grbic et al. |
| 2016/0310274 A1 | 10/2016 | Gross et al. |
| 2016/0317301 A1 | 11/2016 | Quadri et al. |
| 2016/0324633 A1 | 11/2016 | Gross et al. |
| 2016/0324639 A1 | 11/2016 | Nguyen et al. |
| 2016/0331534 A1 | 11/2016 | Buchbinder et al. |
| 2016/0354201 A1 | 12/2016 | Keogh |
| 2016/0361169 A1 | 12/2016 | Gross et al. |
| 2016/0361184 A1 | 12/2016 | Tabor et al. |
| 2016/0367360 A1 | 12/2016 | Cartledge et al. |
| 2016/0367364 A1 | 12/2016 | Torrianni et al. |
| 2017/0000603 A1 | 1/2017 | Conklin et al. |
| 2017/0000604 A1 | 1/2017 | Conklin et al. |
| 2017/0020670 A1 | 1/2017 | Murray et al. |
| 2017/0035562 A1 | 2/2017 | Quadri et al. |
| 2017/0035568 A1 | 2/2017 | Lombardi et al. |
| 2017/0056166 A1 | 3/2017 | Ratz et al. |
| 2017/0056171 A1 | 3/2017 | Cooper et al. |
| 2017/0071733 A1 | 3/2017 | Ghione et al. |
| 2017/0071736 A1 | 3/2017 | Zhu et al. |
| 2017/0076014 A1 | 3/2017 | Bressloff |
| 2017/0079786 A1 | 3/2017 | Li et al. |
| 2017/0079795 A1 | 3/2017 | Morrissey |
| 2017/0100246 A1 | 4/2017 | Rust et al. |

(56) References Cited

U.S. PATENT DOCUMENTS

| | | |
|---|---|---|
| 2017/0112620 A1 | 4/2017 | Curley et al. |
| 2017/0128208 A1 | 5/2017 | Christianson et al. |
| 2017/0143488 A1 | 5/2017 | Lashinski |
| 2017/0143489 A1 | 5/2017 | Lashinski |
| 2017/0165065 A1 | 6/2017 | Rothstein et al. |
| 2017/0172737 A1* | 6/2017 | Kuetting .............. A61F 2/2448 |
| 2017/0172738 A1 | 6/2017 | Kassas |
| 2017/0181851 A1 | 6/2017 | Annest |
| 2017/0181852 A1 | 6/2017 | Kassas |
| 2017/0189177 A1 | 7/2017 | Schweich, Jr. et al. |
| 2017/0196690 A1 | 7/2017 | Racchini et al. |
| 2017/0209266 A1 | 7/2017 | Lane et al. |
| 2017/0209268 A1 | 7/2017 | Cunningham et al. |
| 2017/0216023 A1* | 8/2017 | Lane ..................... A61F 2/243 |
| 2017/0216026 A1 | 8/2017 | Quill et al. |
| 2017/0216030 A1 | 8/2017 | Jonsson |
| 2017/0224480 A1 | 8/2017 | Garde et al. |
| 2017/0224486 A1 | 8/2017 | Delaloye et al. |
| 2017/0231755 A1 | 8/2017 | Gloss et al. |
| 2017/0231760 A1 | 8/2017 | Lane et al. |
| 2017/0239047 A1 | 8/2017 | Quill et al. |
| 2017/0245993 A1 | 8/2017 | Gross et al. |
| 2017/0245994 A1 | 8/2017 | Khairkhahan et al. |
| 2017/0252163 A1 | 9/2017 | Kheradvar |
| 2017/0258584 A1 | 9/2017 | Chang et al. |
| 2017/0258585 A1 | 9/2017 | Marquez et al. |
| 2017/0273784 A1 | 9/2017 | Racchini et al. |
| 2017/0281337 A1 | 10/2017 | Campbell |
| 2017/0281341 A1 | 10/2017 | Lim et al. |
| 2017/0296340 A1 | 10/2017 | Gross et al. |
| 2017/0325948 A1 | 11/2017 | Wallace et al. |
| 2017/0325976 A1 | 11/2017 | Nguyen et al. |
| 2017/0333184 A1 | 11/2017 | Ryan |
| 2017/0333240 A1 | 11/2017 | Stangenes et al. |
| 2017/0348099 A1 | 12/2017 | Mendelson et al. |
| 2017/0348100 A1 | 12/2017 | Lane et al. |
| 2017/0360557 A1 | 12/2017 | Kheradvar et al. |
| 2017/0360558 A1 | 12/2017 | Ma |
| 2017/0360561 A1 | 12/2017 | Bell et al. |
| 2018/0014932 A1 | 1/2018 | Hammer et al. |
| 2018/0021130 A1 | 1/2018 | Danino |
| 2018/0035971 A1 | 2/2018 | Brenner et al. |
| 2018/0042549 A1 | 2/2018 | Ho et al. |
| 2018/0042723 A1 | 2/2018 | Yellin et al. |
| 2018/0043133 A1 | 2/2018 | Wong |
| 2018/0049875 A1 | 2/2018 | Iflah et al. |
| 2018/0049876 A1 | 2/2018 | Miraki |
| 2018/0055628 A1 | 3/2018 | Patel et al. |
| 2018/0055633 A1 | 3/2018 | Costello et al. |
| 2018/0056045 A1 | 3/2018 | Donoghue et al. |
| 2018/0056046 A1 | 3/2018 | Kiersey et al. |
| 2018/0071088 A1 | 3/2018 | Badhwar et al. |
| 2018/0078367 A1 | 3/2018 | Saar et al. |
| 2018/0078368 A1 | 3/2018 | Vidlund et al. |
| 2018/0078370 A1 | 3/2018 | Kovalsky et al. |
| 2018/0085219 A1 | 3/2018 | Krivoruchko |
| 2018/0098837 A1 | 4/2018 | Shahriari |
| 2018/0099124 A1 | 4/2018 | McLoughlin et al. |
| 2018/0116793 A1 | 5/2018 | Salahieh et al. |
| 2018/0116843 A1 | 5/2018 | Schreck et al. |
| 2018/0125642 A1 | 5/2018 | White et al. |
| 2018/0125654 A1 | 5/2018 | Duffy |
| 2018/0126127 A1 | 5/2018 | Devereux et al. |
| 2018/0133000 A1 | 5/2018 | Scheinblum et al. |
| 2018/0133006 A1 | 5/2018 | Jones et al. |
| 2018/0133011 A1 | 5/2018 | Perouse |
| 2018/0140417 A1 | 5/2018 | Sciscio et al. |
| 2018/0147041 A1 | 5/2018 | Chouinard et al. |
| 2018/0147055 A1 | 5/2018 | Vidlund et al. |
| 2018/0153689 A1 | 6/2018 | Maimon et al. |
| 2018/0161158 A1 | 6/2018 | Kovalsky et al. |
| 2018/0161161 A1 | 6/2018 | Yellin et al. |
| 2018/0168793 A1 | 6/2018 | Lees et al. |
| 2018/0177580 A9 | 6/2018 | Shemesh et al. |
| 2018/0177594 A1 | 6/2018 | Patel et al. |
| 2018/0185153 A1 | 7/2018 | Bishop et al. |
| 2018/0193138 A1 | 7/2018 | Vidlund |
| 2018/0200049 A1 | 7/2018 | Chambers et al. |
| 2018/0206983 A1 | 7/2018 | Noe et al. |
| 2018/0214141 A1 | 8/2018 | Mendez |
| 2018/0221016 A1 | 8/2018 | Conklin et al. |
| 2018/0243071 A1 | 8/2018 | Eigler et al. |
| 2018/0243532 A1 | 8/2018 | Willard et al. |
| 2018/0256322 A1 | 9/2018 | Zhang et al. |
| 2018/0256327 A1 | 9/2018 | Perszyk et al. |
| 2018/0256329 A1 | 9/2018 | Chambers et al. |
| 2018/0263767 A1 | 9/2018 | Chau et al. |
| 2018/0263773 A1 | 9/2018 | Poppe et al. |
| 2018/0280174 A1 | 10/2018 | Dwork |
| 2018/0289474 A1 | 10/2018 | Rajagopal et al. |
| 2018/0289475 A1 | 10/2018 | Chung et al. |
| 2018/0289485 A1 | 10/2018 | Rajagopal et al. |
| 2018/0296325 A1 | 10/2018 | McLean |
| 2018/0296335 A1 | 10/2018 | Miyashiro |
| 2018/0296337 A1 | 10/2018 | Duhay et al. |
| 2018/0296341 A1 | 10/2018 | Noe et al. |
| 2018/0303488 A1 | 10/2018 | Hill |
| 2018/0303612 A1 | 10/2018 | Pasquino et al. |
| 2018/0311037 A1 | 11/2018 | Morriss et al. |
| 2018/0311474 A1 | 11/2018 | Tyler, II et al. |
| 2018/0318073 A1 | 11/2018 | Tseng et al. |
| 2018/0318078 A1 | 11/2018 | Willard |
| 2018/0325665 A1 | 11/2018 | Gurovich et al. |
| 2018/0325671 A1 | 11/2018 | Abunassar et al. |
| 2018/0338832 A1 | 11/2018 | Ganesan et al. |
| 2018/0344456 A1 | 12/2018 | Barash et al. |
| 2018/0353293 A1 | 12/2018 | Colavito et al. |
| 2018/0353295 A1 | 12/2018 | Cooper et al. |
| 2018/0360439 A1 | 12/2018 | Niland et al. |
| 2018/0360599 A1 | 12/2018 | Drasler et al. |
| 2019/0000619 A1 | 1/2019 | Quijano et al. |
| 2019/0008640 A1 | 1/2019 | Cooper et al. |
| 2019/0015188 A1 | 1/2019 | Eigler et al. |
| 2019/0021834 A1 | 1/2019 | Nir et al. |
| 2019/0029819 A1 | 1/2019 | Huber |
| 2019/0029823 A1 | 1/2019 | Nguyen et al. |
| 2019/0038404 A1 | 2/2019 | Iamberger et al. |
| 2019/0038405 A1 | 2/2019 | Iamberger et al. |
| 2019/0053894 A1 | 2/2019 | Levi et al. |
| 2019/0053895 A1 | 2/2019 | Levi |
| 2019/0053897 A1 | 2/2019 | Levi et al. |
| 2019/0053898 A1 | 2/2019 | Maimon et al. |
| 2019/0053899 A1 | 2/2019 | Levi |
| 2019/0060051 A1 | 2/2019 | Scheeff et al. |
| 2019/0060057 A1 | 2/2019 | Cohen et al. |
| 2019/0060059 A1 | 2/2019 | Delgado et al. |
| 2019/0060069 A1 | 2/2019 | Maimon et al. |
| 2019/0060071 A1 | 2/2019 | Lane et al. |
| 2019/0069995 A1 | 3/2019 | Levi et al. |
| 2019/0070003 A1 | 3/2019 | Siegel et al. |
| 2019/0076233 A1 | 3/2019 | Fish |
| 2019/0076249 A1 | 3/2019 | Khairkhahan et al. |
| 2019/0083085 A1 | 3/2019 | Gilmore et al. |
| 2019/0091005 A1 | 3/2019 | Fifer et al. |
| 2019/0091015 A1 | 3/2019 | Dienno et al. |
| 2019/0091018 A1 | 3/2019 | Hariton et al. |
| 2019/0091022 A1 | 3/2019 | Yellin et al. |
| 2019/0099265 A1 | 4/2019 | Braido et al. |
| 2019/0099270 A1 | 4/2019 | Morrissey et al. |
| 2019/0105153 A1 | 4/2019 | Barash et al. |
| 2019/0117223 A1 | 4/2019 | Abunassar et al. |
| 2019/0117387 A1 | 4/2019 | Li et al. |
| 2019/0117391 A1 | 4/2019 | Humair |
| 2019/0117400 A1 | 4/2019 | Medema et al. |
| 2019/0117401 A1 | 4/2019 | Cortez, Jr. et al. |
| 2019/0125287 A1 | 5/2019 | Itou et al. |
| 2019/0125536 A1 | 5/2019 | Prabhu et al. |
| 2019/0133528 A1 | 5/2019 | Kassab et al. |
| 2019/0133756 A1 | 5/2019 | Zhang et al. |
| 2019/0133757 A1 | 5/2019 | Zhang et al. |
| 2019/0133765 A1 | 5/2019 | Yellin et al. |
| 2019/0142566 A1 | 5/2019 | Lansky et al. |
| 2019/0142582 A1 | 5/2019 | Drasler et al. |
| 2019/0150867 A1 | 5/2019 | Itou et al. |

(56) References Cited

U.S. PATENT DOCUMENTS

| | | |
|---|---|---|
| 2019/0151509 A1 | 5/2019 | Kheradvar et al. |
| 2019/0167423 A1 | 6/2019 | Hariton et al. |
| 2019/0167429 A1 | 6/2019 | Stearns et al. |
| 2019/0175338 A1 | 6/2019 | White et al. |
| 2019/0175339 A1 | 6/2019 | Vidlund |
| 2019/0175344 A1 | 6/2019 | Khairkhahan |
| 2019/0183639 A1 | 6/2019 | Moore |
| 2019/0183644 A1 | 6/2019 | Hacohen |
| 2019/0183648 A1 | 6/2019 | Trapp et al. |
| 2019/0192287 A1 | 6/2019 | Sandstrom et al. |
| 2019/0192296 A1 | 6/2019 | Schwartz et al. |
| 2019/0209317 A1 | 7/2019 | Zhang et al. |
| 2019/0209320 A1 | 7/2019 | Drasler et al. |
| 2019/0231523 A1 | 8/2019 | Lombardi et al. |
| 2019/0240020 A1 | 8/2019 | Rafiee et al. |
| 2019/0240022 A1 | 8/2019 | Rafiee et al. |
| 2019/0247050 A1 | 8/2019 | Goldsmith |
| 2019/0254815 A1 | 8/2019 | Bruchman et al. |
| 2019/0254816 A1 | 8/2019 | Anderson et al. |
| 2019/0262118 A1 | 8/2019 | Eigler et al. |
| 2019/0262129 A1 | 8/2019 | Cooper et al. |
| 2019/0269413 A1 | 9/2019 | Yodfat et al. |
| 2019/0269504 A1 | 9/2019 | Wang et al. |
| 2019/0269839 A1 | 9/2019 | Wilson et al. |
| 2019/0282360 A1 | 9/2019 | Colavito et al. |
| 2019/0290426 A1 | 9/2019 | Maimon et al. |
| 2019/0290427 A1 | 9/2019 | Mantanus et al. |
| 2019/0307563 A1 | 10/2019 | Sandstrom et al. |
| 2019/0307589 A1 | 10/2019 | Goldberg et al. |
| 2019/0365538 A1 | 12/2019 | Chambers et al. |
| 2019/0388219 A1* | 12/2019 | Lane ............ A61F 2/2409 |
| 2020/0121452 A1 | 4/2020 | Saikrishnan et al. |
| 2020/0121458 A1 | 4/2020 | Vidlund et al. |
| 2020/0179146 A1 | 6/2020 | Christianson et al. |
| 2020/0188097 A1 | 6/2020 | Perrin et al. |
| 2020/0237506 A1 | 7/2020 | Christianson et al. |
| 2020/0289259 A1 | 9/2020 | Christianson et al. |
| 2020/0289263 A1 | 9/2020 | Christianson et al. |
| 2021/0000592 A1 | 1/2021 | Christianson et al. |
| 2021/0137677 A1 | 5/2021 | Christianson et al. |
| 2021/0154011 A1 | 5/2021 | Christianson et al. |
| 2021/0186693 A1 | 6/2021 | Vidlund, I et al. |
| 2021/0220127 A1 | 7/2021 | Vidlund et al. |
| 2021/0220134 A1 | 7/2021 | Christianson et al. |
| 2021/0228349 A1 | 7/2021 | Vidlund et al. |
| 2021/0236280 A1 | 8/2021 | Christianson et al. |
| 2021/0244533 A1 | 8/2021 | Vidlund et al. |
| 2021/0244535 A1* | 8/2021 | Iyer ............ A61F 2/2418 |
| 2021/0244536 A1 | 8/2021 | Christianson et al. |
| 2021/0290381 A1 | 9/2021 | Vidlund et al. |
| 2021/0290385 A1 | 9/2021 | Christianson et al. |
| 2021/0315694 A1 | 10/2021 | Vidlund et al. |
| 2021/0330459 A1* | 10/2021 | Christianson ...... A61F 2/2418 |

FOREIGN PATENT DOCUMENTS

| | | |
|---|---|---|
| AU | 2011238752 A1 | 10/2012 |
| AU | 2011240940 A1 | 10/2012 |
| AU | 2012272855 A1 | 1/2014 |
| AU | 2011236036 B2 | 6/2014 |
| AU | 2011248657 B2 | 12/2014 |
| AU | 2016228261 A1 | 4/2017 |
| AU | 2017210659 A1 | 8/2017 |
| AU | 2013245201 B2 | 10/2017 |
| AU | 2014360294 B2 | 10/2017 |
| AU | 2016249819 A1 | 11/2017 |
| AU | 2016371525 A1 | 5/2018 |
| AU | 2016366783 A1 | 6/2018 |
| AU | 2017214672 B2 | 10/2018 |
| AU | 2017285993 A1 | 1/2019 |
| AU | 2014201920 B2 | 2/2019 |
| AU | 2015411406 B2 | 2/2019 |
| AU | 2019202290 A1 | 4/2019 |
| AU | 2017388857 A1 | 8/2019 |
| BR | PI0909379 B1 | 9/2019 |
| CA | 2531528 A1 | 1/2005 |
| CA | 2609800 A1 | 1/2007 |
| CA | 2822636 A1 | 10/2008 |
| CA | 2398948 C | 8/2009 |
| CA | 2813419 A1 | 4/2012 |
| CA | 2856088 A1 | 5/2013 |
| CA | 2866315 A1 | 9/2013 |
| CA | 2922123 A1 | 4/2015 |
| CA | 2504258 C | 6/2015 |
| CA | 2677648 C | 10/2015 |
| CA | 2815331 C | 10/2015 |
| CA | 2986584 A1 | 11/2015 |
| CA | 2975294 A1 | 8/2016 |
| CA | 2995603 A1 | 2/2017 |
| CA | 2753853 C | 4/2017 |
| CA | 2702615 C | 6/2017 |
| CA | 2744395 C | 8/2017 |
| CA | 3020238 A1 | 11/2017 |
| CA | 3033666 A1 | 2/2018 |
| CA | 3031572 A1 | 3/2018 |
| CA | 3022641 A1 | 5/2018 |
| CA | 3044062 A1 | 6/2018 |
| CA | 3048893 A1 | 7/2018 |
| CA | 3049792 A1 | 7/2018 |
| CA | 3046693 A1 | 8/2018 |
| CA | 2778944 C | 8/2019 |
| CN | 2855366 Y | 1/2007 |
| CN | 100584292 C | 1/2010 |
| CN | 101677820 A | 3/2010 |
| CN | 101677851 A | 3/2010 |
| CN | 102858272 A | 1/2013 |
| CN | 102869320 A | 1/2013 |
| CN | 102892384 A | 1/2013 |
| CN | 103118630 A | 5/2013 |
| CN | 103189015 A | 7/2013 |
| CN | 103228231 A | 7/2013 |
| CN | 103298426 A | 9/2013 |
| CN | 103370035 A | 10/2013 |
| CN | 103391756 A | 11/2013 |
| CN | 102245120 B | 8/2014 |
| CN | 104220027 A | 12/2014 |
| CN | 102917668 B | 1/2015 |
| CN | 104394803 A | 3/2015 |
| CN | 104582637 A | 4/2015 |
| CN | 102905647 B | 7/2015 |
| CN | 103648570 B | 9/2015 |
| CN | 104884000 A | 9/2015 |
| CN | 104160076 B | 12/2015 |
| CN | 105380730 A | 3/2016 |
| CN | 105451687 A | 3/2016 |
| CN | 105520792 A | 4/2016 |
| CN | 105530893 A | 4/2016 |
| CN | 102458309 B | 5/2016 |
| CN | 103200900 B | 5/2016 |
| CN | 105555232 A | 5/2016 |
| CN | 105578992 A | 5/2016 |
| CN | 103338709 B | 6/2016 |
| CN | 105658178 A | 6/2016 |
| CN | 105792780 A | 7/2016 |
| CN | 103347467 B | 8/2016 |
| CN | 103648439 B | 8/2016 |
| CN | 103889472 B | 8/2016 |
| CN | 105899150 A | 8/2016 |
| CN | 103153232 B | 9/2016 |
| CN | 106061437 A | 10/2016 |
| CN | 106068109 A | 11/2016 |
| CN | 106073946 A | 11/2016 |
| CN | 106255475 A | 12/2016 |
| CN | 103917194 B | 2/2017 |
| CN | 106456324 A | 2/2017 |
| CN | 106456325 A | 2/2017 |
| CN | 105073068 B | 3/2017 |
| CN | 106470641 A | 3/2017 |
| CN | 105451684 B | 4/2017 |
| CN | 106573129 A | 4/2017 |
| CN | 103945792 B | 5/2017 |
| CN | 106659394 A | 5/2017 |
| CN | 106716098 A | 5/2017 |
| CN | 106794063 A | 5/2017 |

(56) References Cited

FOREIGN PATENT DOCUMENTS

| | | |
|---|---|---|
| CN | 106890035 A | 6/2017 |
| CN | 106943207 A | 7/2017 |
| CN | 106999054 A | 8/2017 |
| CN | 106999281 A | 8/2017 |
| CN | 104114127 B | 9/2017 |
| CN | 107115161 A | 9/2017 |
| CN | 107249482 A | 10/2017 |
| CN | 107260366 A | 10/2017 |
| CN | 104918582 B | 11/2017 |
| CN | 107374783 A | 11/2017 |
| CN | 107427364 A | 12/2017 |
| CN | 106255476 B | 1/2018 |
| CN | 107530157 A | 1/2018 |
| CN | 107530167 A | 1/2018 |
| CN | 107530177 A | 1/2018 |
| CN | 107613908 A | 1/2018 |
| CN | 104869948 B | 2/2018 |
| CN | 107714240 A | 2/2018 |
| CN | 107920897 A | 4/2018 |
| CN | 104853696 B | 6/2018 |
| CN | 108135696 A | 6/2018 |
| CN | 108430392 A | 8/2018 |
| CN | 108472142 A | 8/2018 |
| CN | 106726007 B | 11/2018 |
| CN | 109124829 A | 1/2019 |
| CN | 109199641 A | 1/2019 |
| CN | 109561962 A | 4/2019 |
| CN | 109567991 A | 4/2019 |
| CN | 109862835 A | 6/2019 |
| CN | 109906063 A | 6/2019 |
| CN | 109996581 A | 7/2019 |
| CN | 110013358 A | 7/2019 |
| CN | 110290764 A | 9/2019 |
| DE | 102014102648 A1 | 9/2015 |
| DE | 102014102650 A1 | 9/2015 |
| DE | 102014102718 A1 | 9/2015 |
| DE | 102014102722 A1 | 9/2015 |
| DE | 202017104793 U1 | 11/2018 |
| DE | 202016008737 U1 | 4/2019 |
| DK | 2549953 T3 | 2/2017 |
| DK | 2254514 T3 | 12/2018 |
| EA | 027348 B1 | 7/2017 |
| EP | 0902704 A4 | 3/1999 |
| EP | 1301225 A2 | 4/2003 |
| EP | 1684666 A2 | 8/2006 |
| EP | 1996246 A2 | 12/2008 |
| EP | 2211779 A1 | 8/2010 |
| EP | 2254513 A1 | 12/2010 |
| EP | 2263605 A1 | 12/2010 |
| EP | 2273947 A1 | 1/2011 |
| EP | 2296744 A1 | 3/2011 |
| EP | 2379008 A2 | 10/2011 |
| EP | 2400926 A2 | 1/2012 |
| EP | 2427145 A2 | 3/2012 |
| EP | 1582178 B1 | 9/2012 |
| EP | 2542186 A2 | 1/2013 |
| EP | 2558030 A1 | 2/2013 |
| EP | 2560579 A1 | 2/2013 |
| EP | 2575681 A1 | 4/2013 |
| EP | 2603172 A2 | 6/2013 |
| EP | 2637607 A1 | 9/2013 |
| EP | 2651337 A2 | 10/2013 |
| EP | 2658476 A1 | 11/2013 |
| EP | 2699201 A1 | 2/2014 |
| EP | 2405966 B1 | 4/2014 |
| EP | 2055263 B1 | 6/2014 |
| EP | 2741711 A2 | 6/2014 |
| EP | 2793763 A1 | 10/2014 |
| EP | 2822503 A2 | 1/2015 |
| EP | 2538879 B1 | 4/2015 |
| EP | 2444031 B1 | 7/2015 |
| EP | 1702247 B1 | 8/2015 |
| EP | 2772228 B1 | 11/2015 |
| EP | 2943160 A2 | 11/2015 |
| EP | 2470098 B1 | 12/2015 |
| EP | 1991168 B1 | 1/2016 |
| EP | 2254512 B1 | 1/2016 |
| EP | 2964152 A1 | 1/2016 |
| EP | 2967853 A1 | 1/2016 |
| EP | 2967860 A1 | 1/2016 |
| EP | 2994073 A1 | 3/2016 |
| EP | 3001978 A1 | 4/2016 |
| EP | 3003187 A1 | 4/2016 |
| EP | 3007649 A1 | 4/2016 |
| EP | 3010447 A1 | 4/2016 |
| EP | 3017792 A1 | 5/2016 |
| EP | 3019092 A1 | 5/2016 |
| EP | 2563236 B1 | 6/2016 |
| EP | 3027143 A1 | 6/2016 |
| EP | 3037064 A1 | 6/2016 |
| EP | 2211758 B1 | 7/2016 |
| EP | 3052053 A1 | 8/2016 |
| EP | 3060140 A1 | 8/2016 |
| EP | 3062745 A1 | 9/2016 |
| EP | 3071149 A1 | 9/2016 |
| EP | 2282700 B1 | 11/2016 |
| EP | 2967854 B1 | 11/2016 |
| EP | 1998713 B1 | 12/2016 |
| EP | 3099271 A1 | 12/2016 |
| EP | 3100701 A1 | 12/2016 |
| EP | 3141219 A1 | 3/2017 |
| EP | 3157469 A1 | 4/2017 |
| EP | 2538880 B1 | 5/2017 |
| EP | 2967852 B1 | 6/2017 |
| EP | 3174503 A1 | 6/2017 |
| EP | 3182931 A1 | 6/2017 |
| EP | 2830536 B1 | 8/2017 |
| EP | 2830537 B1 | 9/2017 |
| EP | 2720642 B1 | 10/2017 |
| EP | 3232941 A1 | 10/2017 |
| EP | 3256076 A1 | 12/2017 |
| EP | 3281608 A1 | 2/2018 |
| EP | 2608815 B1 | 3/2018 |
| EP | 3310302 A1 | 4/2018 |
| EP | 3311778 A1 | 4/2018 |
| EP | 3337412 A1 | 6/2018 |
| EP | 3340931 A1 | 7/2018 |
| EP | 3344188 A1 | 7/2018 |
| EP | 3344197 A1 | 7/2018 |
| EP | 3345573 A1 | 7/2018 |
| EP | 2822473 B1 | 8/2018 |
| EP | 3354208 A1 | 8/2018 |
| EP | 3370649 A1 | 9/2018 |
| EP | 3372198 A1 | 9/2018 |
| EP | 3372199 A1 | 9/2018 |
| EP | 3375411 A1 | 9/2018 |
| EP | 2928538 B1 | 11/2018 |
| EP | 3399947 A1 | 11/2018 |
| EP | 3400913 A1 | 11/2018 |
| EP | 3406224 A1 | 11/2018 |
| EP | 2555709 B1 | 12/2018 |
| EP | 3417813 A1 | 12/2018 |
| EP | 3426188 A1 | 1/2019 |
| EP | 3429507 A1 | 1/2019 |
| EP | 3431040 A1 | 1/2019 |
| EP | 3432825 A1 | 1/2019 |
| EP | 3432834 A1 | 1/2019 |
| EP | 3437669 A1 | 2/2019 |
| EP | 3448312 A1 | 3/2019 |
| EP | 3454787 A1 | 3/2019 |
| EP | 2663259 B1 | 5/2019 |
| EP | 3302364 B1 | 5/2019 |
| EP | 3478224 A1 | 5/2019 |
| EP | 3484411 A1 | 5/2019 |
| EP | 3487420 A1 | 5/2019 |
| EP | 2560580 B1 | 6/2019 |
| EP | 3508113 A1 | 7/2019 |
| EP | 3518748 A1 | 8/2019 |
| EP | 3522830 A1 | 8/2019 |
| EP | 3528749 A1 | 8/2019 |
| EP | 3288495 B1 | 9/2019 |
| EP | 3538024 A1 | 9/2019 |
| EP | 3538025 A1 | 9/2019 |
| EP | 3019123 B1 | 10/2019 |

(56) References Cited

FOREIGN PATENT DOCUMENTS

| | | | |
|---|---|---|---|
| EP | 3552584 A1 | 10/2019 |
| EP | 3552655 A1 | 10/2019 |
| ES | 2369241 T3 | 11/2011 |
| ES | 2647777 T3 | 12/2017 |
| ES | 2664243 T3 | 4/2018 |
| ES | 2675726 T3 | 7/2018 |
| GB | 2539444 A | 12/2016 |
| JP | 2003530956 A | 10/2003 |
| JP | 2005521513 A | 7/2005 |
| JP | 2008506459 A | 3/2008 |
| JP | 2008512211 A | 4/2008 |
| JP | 2009148579 A | 7/2009 |
| JP | 2009525138 A | 7/2009 |
| JP | 2009527316 A | 7/2009 |
| JP | 2009254864 A | 11/2009 |
| JP | 4426182 B2 | 3/2010 |
| JP | 2010518947 A | 6/2010 |
| JP | 2010537680 A | 12/2010 |
| JP | 2011510797 A | 4/2011 |
| JP | 2013503009 A | 1/2013 |
| JP | 2013505082 A | 2/2013 |
| JP | 2013508027 A | 3/2013 |
| JP | 2013512765 A | 4/2013 |
| JP | 2013523261 A | 6/2013 |
| JP | 2013527010 A | 6/2013 |
| JP | 2013543399 A | 12/2013 |
| JP | 2014501563 A | 1/2014 |
| JP | 2014505537 A | 3/2014 |
| JP | 5527850 B2 | 6/2014 |
| JP | 2014518697 A | 8/2014 |
| JP | 2014522678 A | 9/2014 |
| JP | 2015503948 A | 2/2015 |
| JP | 2015510819 A | 4/2015 |
| JP | 2015517854 A | 6/2015 |
| JP | 5767764 B2 | 8/2015 |
| JP | 5803010 B2 | 11/2015 |
| JP | 2015531283 A | 11/2015 |
| JP | 2015534887 A | 12/2015 |
| JP | 2016503710 A | 2/2016 |
| JP | 2016506794 A | 3/2016 |
| JP | 2016508858 A | 3/2016 |
| JP | 2016517748 A | 6/2016 |
| JP | 2016520391 A | 7/2016 |
| JP | 2016526438 A | 9/2016 |
| JP | 2016530046 A | 9/2016 |
| JP | 2016533787 A | 11/2016 |
| JP | 2016540617 A | 12/2016 |
| JP | 2017000729 A | 1/2017 |
| JP | 2017504410 A | 2/2017 |
| JP | 2017515609 A | 6/2017 |
| JP | 2017516536 A | 6/2017 |
| JP | 2017516609 A | 6/2017 |
| JP | 2017131738 A | 8/2017 |
| JP | 2017159055 A | 9/2017 |
| JP | 2017529908 A | 10/2017 |
| JP | 2018501001 A | 1/2018 |
| JP | 2018501901 A | 1/2018 |
| JP | 2018506412 A | 3/2018 |
| JP | 6329570 B2 | 5/2018 |
| JP | 2018515306 A | 6/2018 |
| JP | 2018118136 A | 8/2018 |
| JP | 2018532556 A | 11/2018 |
| JP | 2018535074 A | 11/2018 |
| JP | 2019500952 A | 1/2019 |
| JP | 2019501696 A | 1/2019 |
| JP | 2019501712 A | 1/2019 |
| JP | 6466853 B2 | 2/2019 |
| JP | 6480343 B2 | 3/2019 |
| JP | 2019507664 A | 3/2019 |
| JP | 6506813 B2 | 4/2019 |
| JP | 6526043 B2 | 6/2019 |
| JP | 2019103821 A | 6/2019 |
| JP | 2019514490 A | 6/2019 |
| JP | 2019516527 A | 6/2019 |
| JP | 2019517346 A | 6/2019 |
| JP | 6568213 B2 | 8/2019 |
| JP | 2019134972 A | 8/2019 |
| JP | 2019523090 A | 8/2019 |
| JP | 2019155178 A | 9/2019 |
| JP | 2019526303 A | 9/2019 |
| KR | 20010013991 A | 2/2001 |
| KR | 20120101625 A | 9/2012 |
| KR | 101223313 B1 | 1/2013 |
| KR | 101354189 B1 | 1/2014 |
| KR | 20140139060 A | 12/2014 |
| KR | 20150097757 A | 8/2015 |
| KR | 20160024992 A | 3/2016 |
| RU | 177405 U1 | 2/2018 |
| WO | WO-0044308 A2 | 8/2000 |
| WO | WO-03072287 A1 | 9/2003 |
| WO | WO-2004093728 A2 | 11/2004 |
| WO | WO-2006029062 A1 | 3/2006 |
| WO | WO-2006066150 A2 | 6/2006 |
| WO | WO-2007047945 A2 | 4/2007 |
| WO | WO-2007054015 A1 | 5/2007 |
| WO | WO-2007095233 A2 | 8/2007 |
| WO | WO-2007129220 A2 | 11/2007 |
| WO | WO-2008013915 A2 | 1/2008 |
| WO | WO-2008091925 A2 | 7/2008 |
| WO | WO-2008103280 A2 | 8/2008 |
| WO | WO-2009081396 A2 | 7/2009 |
| WO | WO-2009094188 A2 | 7/2009 |
| WO | WO-2009094189 A1 | 7/2009 |
| WO | WO-2009094197 A1 | 7/2009 |
| WO | WO-2009094501 A1 | 7/2009 |
| WO | WO-2009100242 A2 | 8/2009 |
| WO | WO-2010029190 A1 | 3/2010 |
| WO | WO-2010119110 A1 | 10/2010 |
| WO | WO-2011112706 A2 | 9/2011 |
| WO | WO-2011137531 A1 | 11/2011 |
| WO | WO-2012009558 A2 | 1/2012 |
| WO | WO 2012/035279 | 3/2012 |
| WO | WO-2012063228 A1 | 5/2012 |
| WO | WO-2012063242 A1 | 5/2012 |
| WO | WO-2012112469 A2 | 8/2012 |
| WO | WO-2012145545 A1 | 10/2012 |
| WO | WO-2012161786 A1 | 11/2012 |
| WO | WO-2012175483 A1 | 12/2012 |
| WO | WO-2012178115 A2 | 12/2012 |
| WO | WO-2013021375 A2 | 2/2013 |
| WO | WO-2013085719 A1 | 6/2013 |
| WO | WO-2013103612 A1 | 7/2013 |
| WO | WO-2013116785 A1 | 8/2013 |
| WO | WO-2013128436 A1 | 9/2013 |
| WO | WO-2013148019 A1 | 10/2013 |
| WO | WO-2013166356 A2 | 11/2013 |
| WO | WO-2013177684 A1 | 12/2013 |
| WO | WO-2013184945 A1 | 12/2013 |
| WO | WO-2014011330 A1 | 1/2014 |
| WO | WO-2014064695 A2 | 5/2014 |
| WO | WO-2014121042 A1 | 8/2014 |
| WO | WO-2014133667 A1 | 9/2014 |
| WO | WO-2014137805 A1 | 9/2014 |
| WO | WO-2014140230 A1 | 9/2014 |
| WO | WO-2014162306 A2 | 10/2014 |
| WO | WO-2014164151 A1 | 10/2014 |
| WO | WO-2014168655 A1 | 10/2014 |
| WO | WO-2015004173 A1 | 1/2015 |
| WO | WO-2015014960 A1 | 2/2015 |
| WO | WO-2015017075 A1 | 2/2015 |
| WO | WO-2015055605 A1 | 4/2015 |
| WO | WO-2015057735 A1 | 4/2015 |
| WO | WO-2015058039 A1 | 4/2015 |
| WO | WO-2015061021 A1 | 4/2015 |
| WO | WO-2015117025 A1 | 8/2015 |
| WO | WO-2015120122 A2 | 8/2015 |
| WO | WO-2015123607 A1 | 8/2015 |
| WO | WO-2015127264 A1 | 8/2015 |
| WO | WO-2015142834 A1 | 9/2015 |
| WO | WO-2015153755 A2 | 10/2015 |
| WO | WO-2016011267 A1 | 1/2016 |
| WO | WO-2016025733 A1 | 2/2016 |
| WO | WO-2016083351 A1 | 6/2016 |
| WO | WO-2016097337 A1 | 6/2016 |

(56) References Cited

FOREIGN PATENT DOCUMENTS

| | | |
|---|---|---|
| WO | WO-2016100799 A1 | 6/2016 |
| WO | WO-2016118851 A1 | 7/2016 |
| WO | WO-2016130913 A1 | 8/2016 |
| WO | WO-2016148777 A1 | 9/2016 |
| WO | WO-2016149083 A1 | 9/2016 |
| WO | WO-2016150806 A1 | 9/2016 |
| WO | WO-2016189391 A2 | 12/2016 |
| WO | WO-2017040684 A1 | 3/2017 |
| WO | WO-2017096157 A1 | 6/2017 |
| WO | WO-2017114928 A1 | 7/2017 |
| WO | WO-2017120404 A1 | 7/2017 |
| WO | WO-2017121193 A1 | 7/2017 |
| WO | WO-2017121194 A1 | 7/2017 |
| WO | WO-2017121195 A1 | 7/2017 |
| WO | WO-2017136596 A1 | 8/2017 |
| WO | WO-2017151292 A1 | 9/2017 |
| WO | WO-2017155892 A1 | 9/2017 |
| WO | WO-2017156352 A1 | 9/2017 |
| WO | WO-2017161204 A1 | 9/2017 |
| WO | WO-2017165842 A1 | 9/2017 |
| WO | WO-2017196511 A1 | 11/2017 |
| WO | WO-2017201082 A1 | 11/2017 |
| WO | WO-2017202042 A1 | 11/2017 |
| WO | WO-2017210356 A1 | 12/2017 |
| WO | WO-2017218375 A1 | 12/2017 |
| WO | WO-2018008019 A2 | 1/2018 |
| WO | WO-2018026445 A1 | 2/2018 |
| WO | WO-2018026904 A1 | 2/2018 |
| WO | WO-2018035105 A1 | 2/2018 |
| WO | WO-2018040244 A1 | 3/2018 |
| WO | WO-2018042439 A1 | 3/2018 |
| WO | WO-2018045156 A2 | 3/2018 |
| WO | WO-2018071115 A1 | 4/2018 |
| WO | WO-2018077143 A1 | 5/2018 |
| WO | WO-2018077146 A1 | 5/2018 |
| WO | WO-2018080328 A1 | 5/2018 |
| WO | WO-2018083493 A1 | 5/2018 |
| WO | WO-2018090576 A1 | 5/2018 |
| WO | WO-2018098032 A1 | 5/2018 |
| WO | WO-2018106460 A1 | 6/2018 |
| WO | WO-2018119304 A1 | 6/2018 |
| WO | WO-2018138658 A1 | 8/2018 |
| WO | WO-2018145055 A1 | 8/2018 |
| WO | WO-2018156767 A1 | 8/2018 |
| WO | WO-2018156922 A1 | 8/2018 |
| WO | WO-2018158747 A1 | 9/2018 |
| WO | WO-2018160790 A1 | 9/2018 |
| WO | WO-2018165358 A1 | 9/2018 |
| WO | WO-2018170149 A1 | 9/2018 |
| WO | WO-2018175220 A1 | 9/2018 |
| WO | WO-2018175619 A1 | 9/2018 |
| WO | WO-2018178208 A1 | 10/2018 |
| WO | WO-2018178977 A1 | 10/2018 |
| WO | WO-2018183832 A1 | 10/2018 |
| WO | WO-2018184225 A1 | 10/2018 |
| WO | WO-2018184226 A1 | 10/2018 |
| WO | WO-2018187495 A1 | 10/2018 |
| WO | WO-2018187753 A1 | 10/2018 |
| WO | WO-2018191681 A1 | 10/2018 |
| WO | WO-2018200531 A1 | 11/2018 |
| WO | WO-2018200942 A2 | 11/2018 |
| WO | WO-2018201111 A2 | 11/2018 |
| WO | WO-2018201212 A1 | 11/2018 |
| WO | WO-2018204106 A1 | 11/2018 |
| WO | WO-2018209302 A1 | 11/2018 |
| WO | WO-2018213209 A1 | 11/2018 |
| WO | WO-2018217525 A1 | 11/2018 |
| WO | WO-2018222799 A1 | 12/2018 |
| WO | WO-2018226628 A1 | 12/2018 |
| WO | WO-2019003221 A1 | 1/2019 |
| WO | WO-2019006383 A2 | 1/2019 |
| WO | WO-2019010458 A1 | 1/2019 |
| WO | WO-2019014473 A1 | 1/2019 |
| WO | WO-2019018319 A1 | 1/2019 |
| WO | WO-2019023385 A1 | 1/2019 |
| WO | WO-2019026059 A1 | 2/2019 |
| WO | WO-2019032992 A2 | 2/2019 |
| WO | WO-2019037579 A1 | 2/2019 |
| WO | WO-2019040357 A1 | 2/2019 |
| WO | WO-2019042472 A1 | 3/2019 |
| WO | WO-2019046099 A1 | 3/2019 |
| WO | WO-2019046205 A1 | 3/2019 |
| WO | WO-2019051168 A2 | 3/2019 |
| WO | WO-2019051180 A2 | 3/2019 |
| WO | WO-2019051587 A1 | 3/2019 |
| WO | WO-2019055577 A1 | 3/2019 |
| WO | WO-2019058178 A1 | 3/2019 |
| WO | WO-2019067219 A1 | 4/2019 |
| WO | WO-2019081689 A1 | 5/2019 |
| WO | WO-2019081985 A2 | 5/2019 |
| WO | WO-2019086958 A1 | 5/2019 |
| WO | WO-2019089136 A1 | 5/2019 |
| WO | WO-2019089821 A1 | 5/2019 |
| WO | WO-2019093387 A1 | 5/2019 |
| WO | WO-2019095049 A1 | 5/2019 |
| WO | WO-2019096033 A1 | 5/2019 |
| WO | WO-2019099722 A2 | 5/2019 |
| WO | WO-2019116322 A1 | 6/2019 |
| WO | WO-2019119674 A1 | 6/2019 |
| WO | WO-2019126518 A1 | 6/2019 |
| WO | WO-2019131148 A1 | 7/2019 |
| WO | WO-2019136162 A1 | 7/2019 |
| WO | WO-2019140293 A1 | 7/2019 |
| WO | WO-2019143775 A1 | 7/2019 |
| WO | WO-2019144036 A1 | 7/2019 |
| WO | WO-2019147585 A1 | 8/2019 |
| WO | WO-2019165213 A1 | 8/2019 |
| WO | WO-2019173475 A1 | 9/2019 |
| WO | WO-2019190800 A1 | 10/2019 |
| WO | WO-2019191102 A1 | 10/2019 |
| WO | WO-2019195860 A2 | 10/2019 |

OTHER PUBLICATIONS

International Search Report and Written Opinion for International Application No. PCT/US2019/051615, dated Mar. 2, 2020, 14 pages.
International Search Report and Written Opinion for International Application No. PCT/US2019/051957, dated Apr. 30, 2020, 16 pages.
Office Action for U.S. Appl. No. 16/155,890, dated Feb. 8, 2019, 13 pages.
Office Action for U.S. Appl. No. 16/448,108, dated Jan. 21, 2020, 14 pages.
Office Action for U.S. Appl. No. 16/448,108, dated Sep. 1, 2020, 14 pages.
Office Action for U.S. Appl. No. 16/455,417, dated Sep. 23, 2019, 11 pages.
International Search Report and Written Opinion for International Application No. PCT/US2019/067010, dated Mar. 10, 2020, 17 pages.
Office Action for U.S. Appl. No. 16/455,740, dated Jul. 24, 2020, 7 pages.
International Search Report and Written Opinion for International Application No. PCT/US2020/015231, dated Apr. 23, 2020, 10 pages.
International Search Report and Written Opinion for International Application No. PCT/US2020/021300, dated Oct. 7, 2020, 6 pages.
International Search Report and Written Opinion for International Application No. PCT/US2020/031390, dated Aug. 3, 2020, 10 pages.
International Search Report and Written Opinion for International Application No. PCT/US2020/013240, dated Jun. 3, 2020, 7 pages.
International Search Report and Written Opinion for International Application No. PCT/US2020/022828, dated May 19, 2020, 12 pages.
Office Action for U.S. Appl. No. 16/442,504, dated Jan. 14, 2020, 11 pages.

(56) References Cited

OTHER PUBLICATIONS

International Search Report and Written Opinion for International Application No. PCT/US2020/045195, dated Jan. 8, 2021, 18 pages.
International Search Report and Written Opinion for International Application No. PCT/US2020/047162, dated Dec. 30, 2020, 9 pages.
Office Action for U.S. Appl. No. 16/448,108, dated Mar. 8, 2021, 8 pages.
Office Action for U.S. Appl. No. 16/163,577, dated Mar. 8, 2021, 10 pages.
Office Action for U.S. Appl. No. 17/154,227, dated Mar. 29, 2021, 6 pages.
Office Action for U.S. Appl. No. 16/445,210, dated Jan. 28, 2021, 7 pages.
International Search Report and Written Opinion for International Application No. PCT/US2021/013570, dated Apr. 1, 2021, 9 pages.
International Search Report and Written Opinion for International Application No. PCT/US2019/028822, dated Oct. 24, 2019, 14 pages.
Office Action for U.S. Appl. No. 16/449,420, dated Sep. 1, 2021, 16 pages.
Office Action for U.S. Appl. No. 17/154,227, dated Jun. 18, 2021, 8 pages.
Office Action for U.S. Appl. No. 17/167,983, dated Apr. 13, 2021, 20 pages.
Office Action for U.S. Appl. No. 17/167,988, dated Sep. 22, 2021, 19 pages.
Office Action for U.S. Appl. No. 17/193,936, dated May 27, 2021, 6 pages.
Office Action for U.S. Appl. No. 17/221,547, dated Aug. 4, 2021, 11 pages.
Office Action for U.S. Appl. No. 17/222,182, dated Sep. 2, 2021, 23 pages.
Office Action for U.S. Appl. No. 17/222,430, dated Oct. 7, 2021, 17 pages.
Office Action for U.S. Appl. No. 17/236,219, dated Aug. 4, 2021, 17 pages.
Office Action for U.S. Appl. No. 17/221,547, dated Oct. 21, 2021, 9 pages.

* cited by examiner distal view proximal view

```
                                   10
                                      ↘

┌─────────────────────────────────────────────────────────┐
│ Dispose in the atrium of the heart a distal end of a    │
│ delivery catheter having disposed in a lumen thereof    │
│ a prosthetic heart valve in a compressed configuration  │
│                           11                            │
└─────────────────────────────────────────────────────────┘
                              │
                              ▼
┌─────────────────────────────────────────────────────────┐
│ Release the prosthetic valve from the lumen of the      │
│ delivery catheter such that the prosthetic valve        │
│ transitions from the compressed configuration to an     │
│ expanded configuration                                  │
│                           12                            │
└─────────────────────────────────────────────────────────┘
                              │
                              ▼
┌─────────────────────────────────────────────────────────┐
│ Seat at least a portion of the prosthetic valve in the  │
│ annulus of the native valve                             │
│                           13                            │
└─────────────────────────────────────────────────────────┘
                              │
                              ▼
┌─────────────────────────────────────────────────────────┐
│ Place a septal anchoring element of the prosthetic      │
│ valve in contact with at least one of a native septal   │
│ wall or a septal leaflet area to stabilize the          │
│ prosthetic valve in the annulus when the prosthetic     │
│ valve is seated in the annulus.                         │
│                           14                            │
└─────────────────────────────────────────────────────────┘
```

FIG. 22 ial Patent Application Ser. No. 62/962,902, filed
VENTRICULAR STABILITY ELEMENTS FOR SIDE-DELIVERABLE PROSTHETIC HEART VALVES AND METHODS OF DELIVERY

CROSS-REFERENCE TO RELATED APPLICATIONS

This application is a continuation of International Patent Application Serial No. PCT/US2021/013570, filed Jan. 15, 2021, entitled "Ventricular Stability Elements for Side-Deliverable Prosthetic Heart Valve and Methods of Delivery," which claims priority to and the benefit of U.S. Provisional Patent Application Ser. No. 62/962,902, filed Jan. 17, 2020, entitled "Ventricular Stability Tab for Side-Delivered Transcatheter Heart Valve and Methods of Delivery," the disclosures of which are incorporated herein by reference in their entireties.

BACKGROUND

Embodiments are described herein that relate to prosthetic heart valves, and devices and methods for use in the delivery and deployment of such valves.

Prosthetic heart valves can pose challenges for delivery and deployment within a heart, particularly for delivery by catheters through the patient's vasculature rather than through a surgical approach. Delivery of traditional transcatheter prosthetic valves generally includes compressing the valve in a radial direction and loading the valve into a delivery catheter such that a central annular axis of the valve is parallel to the lengthwise axis of the delivery catheter. The valves are deployed from the end of the delivery catheter and expanded outwardly in a radial direction from the central annular axis. The expanded size (e.g., diameter) of traditional valves, however, can be limited by the internal diameter of the delivery catheter. The competing interest of minimizing delivery catheter size presents challenges to increasing the expanded diameter of traditional valves (e.g., trying to compress too much material and structure into too little space).

Some transcatheter prosthetic valves can be configured for orthogonal delivery, which can have an increased expanded diameter relative to traditional valves. In orthogonal delivery, for example, the valve is compressed and loaded into a delivery catheter such that a central annular axis of the valve is substantially orthogonal to the lengthwise axis of the delivery catheter, which can allow the valve to be compressed laterally and extended longitudinally (e.g., in a direction parallel to the lengthwise axis of the delivery catheter). With traditional and/or orthogonally delivered transcatheter prosthetic valves, it is also desirable to provide one or more ways of anchoring, securing, and/or stabilizing the valve in the native annuls without substantially increasing a compressed size of the valve.

Accordingly, a need exists for prosthetic valves with one or more anchoring and/or stabilizing features while maintaining a relatively small compressed size that allows for transcatheter delivery of the valve.

SUMMARY

The embodiments described herein relate generally to transcatheter prosthetic valves and methods for delivering transcatheter prosthetic valves. In some embodiments, a prosthetic heart valve includes a valve frame defining an aperture that extends along a central axis and a flow control component mounted within the aperture. The flow control component is configured to permit blood flow along the central axis in a first direction from an inflow end to an outflow end of the flow control component and block blood flow in a second direction, opposite the first direction. The valve frame includes a distal anchoring element, a proximal anchoring element, and a septal subannular anchoring element. The prosthetic heart valve has a compressed configuration for side-delivery to a heart of a patient via a delivery. The prosthetic heart valve is configured to transition from the compressed configuration to an expanded configuration when released from the delivery catheter. The prosthetic heart valve is configured to be seated in an annulus of a native valve of the heart when in the expanded configuration. The distal, proximal, and septal anchoring elements are configured to be inserted through the annulus of the native valve prior to the prosthetic heart valve being fully seated therein. The septal anchoring element is configured to extend below the annulus and contact ventricular septal tissue to stabilize the prosthetic heart valve in the annulus when the prosthetic heart valve is seated in the annulus.

BRIEF DESCRIPTION OF THE DRAWINGS

FIG. 22 is a flowchart illustrating a method of deploying a prosthetic heart valve in an annulus of a native valve of a heart of a patient, according to an embodiment.

DETAILED DESCRIPTION

Figure 1:
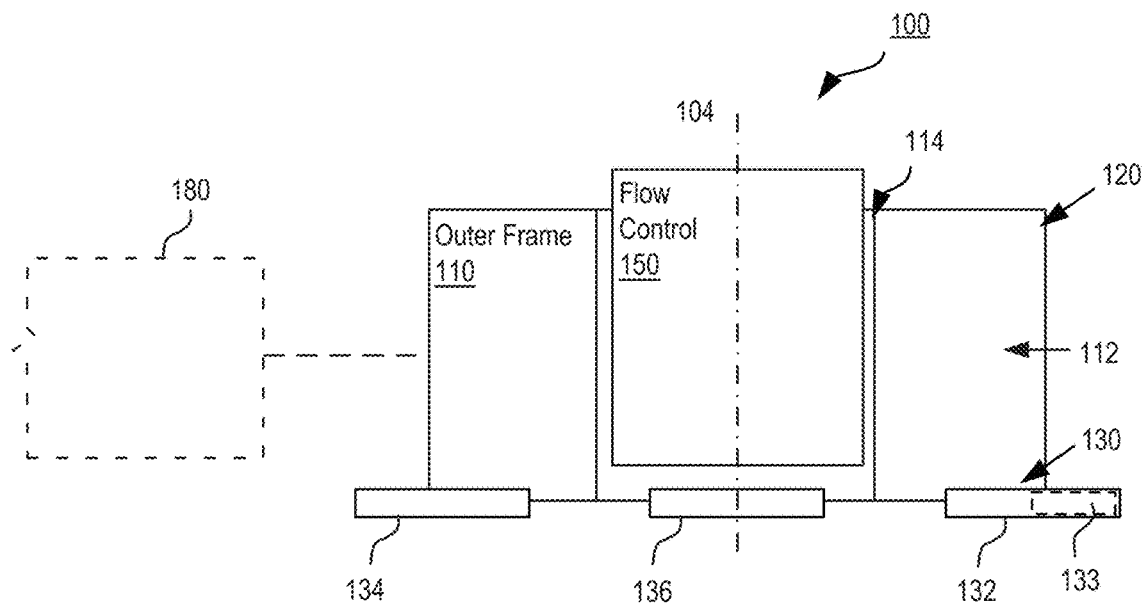
FIGS. 1-5 are schematic illustrations of a side-deliverable transcatheter prosthetic valve according to an embodiment.

Disclosed embodiments are directed to transcatheter prosthetic heart valves and/or components thereof, and methods of manufacturing, loading, delivering, and/or deploying the transcatheter prosthetic valves and/or components thereof. The transcatheter prosthetic heart valves can have a valve frame having at least a septal subannular anchoring element mounted on a septal side of the valve frame and a flow control component mounted within a central lumen or aperture of the valve frame. The flow control component can be configured to permit blood flow in a first direction through an inflow end of the valve and block blood flow in a second direction, opposite the first direction, through an outflow end of the valve. The valves described herein can be compressible and expandable along a long-axis (also referred to as a longitudinal axis) substantially parallel to a lengthwise cylindrical axis of a delivery catheter used to deliver the valves. The valves can be configured to transition between a compressed configuration for introduction into the body using the delivery catheter, and an expanded configuration for implanting at a desired location in the body.

In some implementations, the embodiments described herein are directed to a prosthetic heart valve that is a low-profile, side-delivered implantable prosthetic heart valve. The prosthetic heart valves can have at least a ring-shaped or annular valve frame, an inner flow control component (e.g., a 2-leaflet or 3-leaflet sleeve, and/or the like) mounted in the valve frame, a distal anchoring element (e.g., a subannular distal anchoring element, tab, or the like) configured to extend into the right ventricular outflow tract (RVOT), a septal anchoring element configured to extend down the septal wall to pin the septal leaflet away from the coapting leaflets of the prosthetic valve, and a proximal anchoring element (e.g., a subannular proximal anchoring element, tab, or the like) configured to extend into the proximal subannular space, preferably between the septal and the posterior leaflets of the heart.

In some embodiments, a prosthetic heart valve includes a valve frame defining an aperture that extends along a central axis and a flow control component mounted within the aperture. The flow control component is configured to permit blood flow along the central axis in a first direction from an inflow end to an outflow end of the flow control component and block blood flow in a second direction, opposite the first direction. The valve frame includes a distal anchoring element, a proximal anchoring element, and a septal subannular anchoring element. The prosthetic heart valve has a compressed configuration for side-delivery to a heart of a patient via a delivery. The prosthetic heart valve is configured to transition from the compressed configuration to an expanded configuration when released from the delivery catheter. The prosthetic heart valve is configured to be seated in an annulus of a native valve of the heart when in the expanded configuration. The distal, proximal, and septal anchoring elements are configured to be inserted through the annulus of the native valve prior to the prosthetic heart valve being fully seated therein. The septal anchoring element is configured to extend below the annulus and contact ventricular septal tissue to stabilize the prosthetic heart valve in the annulus when the prosthetic heart valve is seated in the annulus.

In some implementations, the distal anchoring element is configured to engage, for example, ventricular tissue distal to the annulus, the proximal anchoring element is configured to engage, for example, ventricular tissue proximal to the annulus, and the septal anchoring element is configured to engage, for example, at least one of a native septal wall or a native septal leaflet when the prosthetic heart valve is seated in the annulus. In some implementations, the septal anchoring element can stabilize the valve against any intra-annular rolling forces and/or any intra-annular twisting forces that might affect a desired location or positioning of the prosthetic valve within the annulus, (e.g., tilted, angled, twisted, rolled, etc.).

In some embodiments, a prosthetic heart valve includes a valve frame having a transannular section and a supra-annular section (e.g., an atrial collar) attached around a top edge of the transannular section, a distal anchoring element coupled to the transannular section, a proximal anchoring element coupled to the transannular section, a septal anchoring element coupled to the transannular section, and a flow control component mounted within the valve frame. The flow control component is configured to permit blood flow in a first direction from an inflow end to an outflow end of the prosthetic heart valve and to block blood flow in a second direction, opposite the first direction. The prosthetic heart valve has a compressed configuration for introduction into a heart of a patient via a delivery catheter and an expanded configuration when the prosthetic heart valve is released from the delivery catheter into the heart. The prosthetic heart valve is configured to be seated in an annulus of a native valve of the heart when in the expanded configuration. When the prosthetic heart valve is seated in the annulus of the native valve, the distal anchoring element is configured to be disposed in a ventricular outflow tract, he proximal anchoring element is configured to be disposed in a proximal subannular area of the heart, and the septal anchoring element is configured to extend below the annulus and contact at least one of a native septal wall or a native septal leaflet.

In some embodiments, a side-deliverable transcatheter prosthetic heart valve includes (i) a self-expanding annular support frame, said annular support frame with an outer perimeter wall having at least a distal side, a proximal side, and a septal side and circumscribing a central channel extending along a central vertical axis in an expanded configuration; (ii) a flow control component mounted within the annular support frame and configured to permit blood flow in a first direction through an inflow end of the valve and block blood flow in a second direction, opposite the first direction, through an outflow end of the valve; (iii) a distal subannular anchoring element mounted on the distal side of the annular support frame; (iv) a proximal subannular anchoring element mounted on the proximal side of the annular support frame; and (v) a septal subannular anchoring element or tab mounted on the septal side of the annular support frame. The valve is compressible to a compressed configuration for introduction into the body using a delivery catheter. The valve in the compressed configuration has a height of 8-12 mm, a width of 8-12 mm, and a length of 25-80 mm. A horizontal axis of the valve in the compressed configuration is substantially parallel to a lengthwise cylindrical axis of the delivery catheter. The valve in the expanded configuration has a height of about 5-60 mm and a diameter of about 25-80 mm. In some implementations, the valve in the compressed configuration can be oriented such that the horizontal axis is at an intersecting angle of between 45-135 degrees to the central vertical axis. In some implementations, the valve in the expanded configuration can be oriented such that the horizontal axis is at an intersecting angle of between 45-135 degrees to the central vertical axis.

Any of the prosthetic heart valves described herein can be configured to transition between an expanded configuration and a compressed configuration. For example, any of the embodiments described herein can be a balloon-inflated prosthetic heart valve, a self-expanding prosthetic heart valve, and/or the like.

Any of the prosthetic heart valves described herein can be compressible—into the compressed configuration—in a lengthwise or orthogonal direction relative to the central axis of the flow control component that can allow a large diameter valve (e.g., having a height of about 5-60 mm and a diameter of about 20-80 mm) to be delivered and deployed from the inferior vena cava directly into the annulus of a native mitral or tricuspid valve using, for example, a 24-36 Fr delivery catheter and without delivery and deployment from the delivery catheter at an acute angle of approach.

Any of the prosthetic heart valves described herein can have a central axis when in a compressed configuration that is co-axial or at least substantially parallel with blood flow direction through the valve. In some embodiments, the compressed configuration of the valve is orthogonal to the blood flow direction. In some embodiments, a long-axis is oriented at an intersecting angle of between 45-135 degrees to the first direction when in the compressed configuration and/or the expanded configuration.

In some embodiments, the annular support frame is a compressible wire frame including one of braided-wire cells, laser-cut wire cells, photolithography produced wire cells, 3D printed wire cells, wire cells formed from intermittently connected single strand wires in a wave shape, a zig-zag shape, or spiral shape, and combinations thereof.

Any of the prosthetic heart valves described herein can include a septal anchoring element extending from a lower septal side of a frame of the prosthetic heart valve, which can be used, for example, as a septal tissue and/or leaflet anchoring and/or stabilization element or tab. The septal anchoring element can include and/or can be formed from a wire loop or wire frame, an integrated frame section, and/or a stent, extending from the frame (e.g., about 10-40 mm away from the frame).

Any of the prosthetic heart valves described herein can include a distal anchoring element extending from a lower distal side of the frame of the prosthetic heart valve, which can be used, for example, as a ventricular outflow tract tab. The distal anchoring element can include and/or can be formed from a wire loop or wire frame, an integrated frame section, and/or a stent, extending from the frame (e.g., about 10-40 mm away the tubular frame).

Any of the prosthetic heart valves described herein can include a proximal anchoring element extending from a lower proximal side of the frame of the prosthetic heart valve, which can be used, for example, as a proximal tissue and/or area anchoring and/or stabilization tab. The proximal anchoring element can include and/or can be formed from a wire loop or wire frame, an integrated frame section, and/or a stent, extending away from the frame (e.g., about 10-40 mm away from the frame). The proximal anchoring element can be one of a fixed anchoring element or an anchoring element configured to transition from a first (e.g., compressed) configuration to a second (e.g., expanded) configuration after the prosthetic heart valve is seated in an annulus of a native heart valve. For example, the proximal anchoring element can be moveable from a first stowed position (e.g., held against an outer perimeter wall of the frame) while the prosthetic heart valve is being positioned in the native annulus to a second deployed position that extends away from the outer perimeter wall to provide a proximal subannular anchor.

Any of the prosthetic heart valves described herein can include (i) an upper anchoring element attached to a distal upper edge of the tubular frame, the upper anchoring element can include or be formed from a wire loop or wire frame extending from about 2-20 mm away from the tubular frame, and (ii) a lower anchoring element (e.g., used as a RVOT tab) extending from a distal side of the tubular frame, the lower anchoring element can include and/or can be formed from a wire loop or wire frame extending from about 10-40 mm away from the tubular frame.

Any of the prosthetic heart valves described herein can include a distal lower anchoring element configured to be positioned into the RVOT of the right ventricle, a proximal lower anchoring element configured to be positioned into a subannular position in contact with and/or adjacent to subannular tissue of the right ventricle on a proximal side of the annulus, and a septal subannular anchoring tab mounted on the septal side of the annular support frame and configured to be positioned into a subannular position in contact with and/or in contact with septal wall tissue and/or native septal leaflets. The prosthetic heart valve can also include a distal upper anchoring element configured to be positioned into a supra-annular position in contact with and/or adjacent to supra-annular tissue of the right atrium. The distal upper anchoring element can provide a supra-annular downward force in the direction of the right ventricle and the distal and proximal lower anchoring elements can provide a subannular upward force in the direction of the right atrium. The septal anchoring element similarly can provide an upward force in the direction of the right atrium and/or can stabilize the valve against any intra-annular rolling forces and/or any intra-annular twisting forces that might affect a desired location or positioning of the prosthetic valve within the annulus, (e.g., tilted, angled, twisted, rolled, etc.).

Any of the prosthetic valves and/or components thereof may be fabricated from any suitable biocompatible material or combination of materials. For example, an outer valve frame, an inner valve frame (e.g., of an inner flow control component), and/or components thereof may be fabricated from biocompatible metals, metal alloys, polymer coated metals, and/or the like. Suitable biocompatible metals and/or metal alloys can include stainless steel (e.g., 316 L stainless steel), cobalt chromium (Co—Cr) alloys, nickel-titanium alloys (e.g., Nitinol®), and/or the like. Moreover, any of the outer or inner frames described herein can be formed from superelastic or shape-memory alloys such as nickel-titanium alloys (e.g., Nitinol®). Any of the prosthetic valves and/or components thereof can include any suitable coating, covering, and/or the like. Suitable polymer coatings can include, for example, polyethylene vinyl acetate (PEVA), poly-butyl methacrylate (PBMA), translute Styrene Isoprene Butadiene (SIBS) copolymer, polylactic acid, polyester, polylactide, D-lactic polylactic acid (DLPLA), polylactic-co-glycolic acid (PLGA), and/or the like. Some such polymer coatings may form a suitable carrier matrix for drugs such as, for example, Sirolimus, Zotarolimus, Biolimus, Novolimus, Tacrolimus, Paclitaxel, Probucol, and/or the like.

Additional biocompatible synthetic material(s) can include, for example, polyesters, polyurethanes, elastomers, thermoplastics, thermoplastic polycarbonate urethane, polyether urethane, segmented polyether urethane, silicone polyether urethane, polyetheretherketone (PEEK), silicone-polycarbonate urethane, polypropylene, polyethylene, low-density polyethylene (LDPE), high-density polyethylene (HDPE), ultra-high density polyethylene (UHDPE), polyolefins, polyethylene-glycols, polyethersulphones, polysulphones, polyvinylpyrrolidones, polyvinylchlorides, other fluoropolymers, polyesters, polyethylene-terephthalate (PET) (e.g., Dacron), Poly-L-lactic acids (PLLA), polyglycolic acid (PGA), poly(D, L-lactide/glycolide) copolymer (PDLA), silicone polyesters, polyamides (Nylon), polytetrafluoroethylene (PTFE) (e.g., Teflon), elongated PTFE, expanded PTFE, siloxane polymers and/or oligomers, polylactones, and/or the like or block co-polymers using the same. For example, where a thin, durable synthetic material is contemplated (e.g., for a covering), synthetic polymer materials such expanded PTFE or polyester (or any of the other materials described herein) may optionally be used.

Any of the outer valve frames, inner valve frames (e.g., of the flow control components), and/or portions or components thereof can be internally or externally covered, partially or completely, with a biocompatible material such as pericardium. A valve frame may also be optionally externally covered, partially or completely, with a second biocompatible material such as polyester or Dacron®. Disclosed embodiments may use tissue, such as a biological tissue that is a chemically stabilized pericardial tissue of an animal, such as a cow (bovine pericardium), sheep (ovine pericardium), pig (porcine pericardium), or horse (equine pericardium). Preferably, the tissue is bovine pericardial tissue. Examples of suitable tissue include that used in the products DuraGuard®, Peri-Guard®, and Vascu-Guard®, all products currently used in surgical procedures, and which are marketed as being harvested generally from cattle less than 30 months old. Alternatively, disclosed embodiments may use and/or may be covered, partially or completely, with a biocompatible synthetic such as any of those described above.

Any method for delivering prosthetic heart valves described herein can include side/orthogonal delivery of the prosthetic heart valve to a desired location in the body that includes advancing a delivery catheter to the desired location in the body and delivering the prosthetic heart valve in a compressed configuration to the desired location in the body by releasing the valve from the delivery catheter. The valve transitions to an expanded configuration when released from the delivery catheter.

Any method for delivering prosthetic heart valves described herein can include attaching a pulling/pushing wire (e.g., a rigid elongated rod, draw wire, and/or the like) to a sidewall or an anchoring element (e.g., a distal anchoring element) of the prosthetic heart valve. Such methods can include releasing the valve from the delivery catheter by one of (i) pulling the valve out of the delivery catheter using the pulling/pushing wire, wherein advancing the pulling/pushing wire away from a distal end of the delivery catheter pulls the compressed valve out of the delivery catheter, or (ii) pushing the valve out of the delivery catheter using the pulling/pushing wire, wherein advancing the pulling/pushing wire through and/or out of a distal end of the delivery catheter pushes the compressed valve out of the delivery catheter.

Any method for delivering prosthetic heart valves described herein can include orthogonal delivery of the prosthetic heart valve to a native annulus of a human heart that includes at least one of (i) advancing the delivery catheter to the tricuspid valve or pulmonary artery of the heart through the inferior vena cava (IVC) via the femoral vein, (ii) advancing to the tricuspid valve or pulmonary artery of the heart through the superior vena cava (SVC) via the jugular vein, or (iii) advancing to the mitral valve of the heart through a trans-atrial approach (e.g., fossa ovalis or lower), via the IVC-femoral or the SVC jugular approach; and (iv) delivering prosthetic heart valve to the native annulus by releasing the valve from the delivery catheter.

In some embodiments, a prosthetic heart valve has a valve frame with a distal anchoring element, a proximal anchoring element, a septal anchoring element, and a flow control component mounted within the valve frame. In some implementations, a method of deploying the prosthetic heart valve in an annulus of a native valve of a heart of a patient includes disposing in the atrium of the heart a distal end of a delivery catheter having disposed in a lumen thereof the prosthetic heart valve in a compressed configuration. The prosthetic heart valve is released from the lumen of the delivery catheter such that the prosthetic heart valve transitions from the compressed configuration to an expanded configuration. At least a portion of the prosthetic heart valve is seated in the annulus of the native valve. The septal anchoring element is placed in contact with at least one of a native septal wall or a septal leaflet area to stabilize the prosthetic heart valve in the annulus when the prosthetic heart valve is seated in the annulus.

Any method for delivering prosthetic heart valves described herein can include releasing the valve from a delivery catheter while increasing blood flow during deployment of the valve by partially releasing the valve from the delivery catheter to establish blood flow around the partially released valve and blood flow through the flow control component; (ii) completely releasing the valve from the delivery catheter while maintaining attachment to the valve to transition to a state with increased blood flow through the flow control component and decreased blood flow around the valve; (iii) deploying the valve into a final mounted position in a native annulus to transition to a state with complete blood flow through the flow control component and minimal or no blood flow around the valve; and (iv) disconnecting and withdrawing a positioning catheter, pulling or pushing wire or rod, and/or the delivery catheter.

In some embodiments, a method of delivering a prosthetic heart valve to an annulus of a native valve between an atrium and a ventricle of a heart of a patient includes disposing adjacent to the annulus of the native valve a distal end of a delivery catheter having disposed in a lumen thereof the prosthetic heart valve. The prosthetic heart valve includes a valve frame with a septal anchoring element configured to extend down the septal wall to pin the septal leaflet away from the coapting leaflets of the prosthetic heart valve, a distal anchoring element and a proximal anchoring element, and a flow control component mounted within the valve frame. The prosthetic heart valve is in a compressed configuration within the lumen of the delivery catheter. The prosthetic heart valve is released from the lumen of the delivery catheter. The prosthetic heart valve is configured to transition from the compressed configuration to an expanded configuration in response to being released. A portion of the distal anchoring element is placed on the ventricle side of the annulus of the native valve. The prosthetic heart valve is seated in the annulus when the proximal anchoring element is in a first configuration and the proximal anchoring element is transitioned from the first configuration to a second configuration after the prosthetic heart valve is seated in the annulus.

In some embodiments, the septal anchoring element is transitioned from a first stowed or folded position to a second expanded position. For example, the septal anchoring element can be formed from a shape-memory alloy or the like that can transition between two or more configurations. In some implementations, the transition can be actuated and/or initiated when the valve is sufficiently released from the delivery catheter. In some implementations, the transition can be actuated and/or initiated by releasing a tensile element. In some implementations, the transition can be actuated and/or initiated by a secondary catheter tool that folds the septal anchoring element down from a first stowed position and into the second expanded, subannular position. Similarly, in some embodiments, the proximal anchoring element is transitioned from a first stowed or folded position to a second expanded position. In such embodiments, the seating of the proximal anchoring element includes releasing the proximal anchoring element from a compressed pre-release configuration to an expanded post-release configuration with the proximal anchoring element extending into the proximal subannular anchoring area.

The terminology used herein is for the purpose of describing particular embodiments only and is not intended to limit the full scope of the claims. Unless defined otherwise, all technical and scientific terms used herein have the same meanings as commonly understood by one of ordinary skill in the art.

As used herein, the singular forms "a," "an," and "the" are intended to include the plural forms as well, unless the context clearly indicates otherwise. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (e.g., bodies of the appended claims) are generally intended as "open" terms (e.g., the term "including" should be interpreted as "including but not limited to," the term "having" should be interpreted as "having at least," etc.). Similarly, the terms "comprises" and/or "comprising," when used in this specification, specify the presence of stated features, integers (or fractions thereof), steps, operations, elements, and/or components, but do not preclude the presence or addition of one or more other features, integers (or fractions thereof), steps, operations, elements, components, and/or groups thereof. As used in this document, the term "comprising" means "including, but not limited to."

As used herein the term "and/or" includes any and all combinations of one or more of the associated listed items. It should be understood that any suitable disjunctive word and/or phrase presenting two or more alternative terms, whether in the description, claims, or drawings, contemplate the possibilities of including one of the terms, either of the terms, or both/all terms. For example, the phrase "A or B" will be understood to include the possibilities of "A" or "B" or "A and B."

All ranges disclosed herein also encompass any and all possible subranges and combinations of subranges thereof unless expressly stated otherwise. Any listed range should be recognized as sufficiently describing and enabling the same range being broken down into at least equal subparts unless expressly stated otherwise. As will be understood by one skilled in the art, a range includes each individual member.

The term "valve prosthesis," "prosthetic heart valve," and/or "prosthetic valve" can refer to a combination of a frame and a leaflet or flow control structure or component, and can encompass both complete replacement of an anatomical part (e.g., a new mechanical valve replaces a native valve), as well as medical devices that take the place of and/or assist, repair, or improve existing anatomical parts (e.g., the native valve is left in place).

Prosthetic valves disclosed herein can include a member (e.g., a frame) that can be seated within a native valve annulus and can be used as a mounting element for a leaflet structure, a flow control component, or a flexible reciprocating sleeve or sleeve-valve. It may or may not include such a leaflet structure or flow control component, depending on the embodiment. Such members can be referred to herein as an "annular support frame," "tubular frame," "wire frame," "valve frame," "flange," "collar," and/or any other similar terms.

The term "flow control component" can refer in a non-limiting sense to a leaflet structure having 2-, 3-, 4-leaflets of flexible biocompatible material such a treated or untreated pericardium that is sewn or joined to a annular support frame, to function as a prosthetic heart valve. Such a valve can be a heart valve, such as a tricuspid, mitral, aortic, or pulmonary, that is open to blood flowing during diastole from atrium to ventricle, and that closes from systolic ventricular pressure applied to the outer surface. Repeated opening and closing in sequence can be described as "reciprocating." The flow control component is contemplated to include a wide variety of (bio)prosthetic artificial heart valves and/or components. For example, such (bio)prosthetics can include ball valves (e.g., Starr-Edwards), bileaflet valves (St. Jude), tilting disc valves (e.g., Bjork-Shiley), stented pericardium heart-valve prosthesis' (bovine, porcine, ovine) (Edwards line of bioprostheses, St. Jude prosthetic valves), as well as homograft and autograft valves. Bioprosthetic pericardial valves can include bioprosthetic aortic valves, bioprosthetic mitral valves, bioprosthetic tricuspid valves, and bioprosthetic pulmonary valves.

The terms "anchoring element" or "tab" or "arm" refer to structural elements extending from a portion of the valve or valve frame (e.g., extending away from a valve sidewall or body or collar) to provide an anchoring or stabilizing function to the valve. When used in conjunction with the terms distal, proximal, septal, and/or anterior, it should be understood that the anchoring or stabilizing element so described is attached to and/or integral with the valve at a distal, proximal, septal, and/or anterior location, respectively. A distal location on a valve refers to a portion of the valve furthest from the practitioner which exits the delivery catheter first, and which can be placed at or near distal subannular native tissue such as the ventricular outflow tract. A proximal location on a valve refers to a portion of the valve closest to the practitioner which exits the delivery catheter last, and which can be placed at or near proximal subannular native tissue such as tissue closest to the inferior vena cava. A septal location on a valve refers to a portion of the valve at a point between a proximal and a distal location, and which can be placed at or near septal subannular native tissue such as the septal leaflet or septal wall. An anterior location on a valve refers to a portion of the valve at a point between a proximal and a distal location, and which can be placed at or near anterior tissue opposite the septal tissue. When used in conjunction with the term "lower," it should be understood that the anchoring or stabilizing element so described is attached to and/or integral with the valve sidewall or body at or along subannular region of the valve. Conversely, when used in conjunction with the term "upper," it should be understood that the anchoring or stabilizing element so described is attached to and/or integral with the valve at or along a supra-annular region, collar, or atrial cuff of the valve.

Any of the disclosed valve embodiments may be delivered by a transcatheter approach. The term "transcatheter" is used to define the process of accessing, controlling, and/or delivering a medical device or instrument within the lumen of a catheter that is deployed into a heart chamber (or other desired location in the body), as well as an item that has been delivered or controlled by such as process. Transcatheter access is known to include cardiac access via the lumen of the femoral artery and/or vein, via the lumen of the brachial artery and/or vein, via lumen of the carotid artery, via the lumen of the jugular vein, via the intercostal (rib) and/or sub-xiphoid space, and/or the like. Moreover, transcatheter cardiac access can be via the inferior vena cava (IVC), superior vena cava (SVC), and/or via a trans-atrial (e.g., fossa ovalis or lower). Transcatheter can be synonymous with transluminal and is functionally related to the term "percutaneous" as it relates to delivery of heart valves. As used herein, the term "lumen" can refer to the inside of a cylinder or tube.

The mode of cardiac access can be based at least in part on a "body channel," used to define a blood conduit or vessel within the body, and the particular application of the disclosed embodiments of prosthetic valves can determine the body channel at issue. An aortic valve replacement, for example, would be implanted in, or adjacent to, the aortic annulus. Likewise, a tricuspid or mitral valve replacement would be implanted at the tricuspid or mitral annulus, respectively. While certain features described herein may be particularly advantageous for a given implantation site, unless the combination of features is structurally impossible or excluded by claim language, any of the valve embodiments described herein could be implanted in any body channel.

The term "expandable" as used herein may refer to a prosthetic heart valve or a component of the prosthetic heart valve capable of expanding from a first, delivery size or configuration to a second, implantation size or configuration. An expandable structure, therefore, is not intended to refer to a structure that might undergo slight expansion, for example, from a rise in temperature or other such incidental cause, unless the context clearly indicates otherwise. Conversely, "non-expandable" should not be interpreted to mean completely rigid or a dimensionally stable, as some slight expansion of conventional "non-expandable" heart valves, for example, may be observed.

The prosthetic valves disclosed herein and/or components thereof are generally capable of transitioning between two or more configurations, states, shapes, and/or arrangements. For example, prosthetic valves described herein can be "compressible" and/or "expandable" between any suitable number of configurations. Various terms can be used to describe or refer to these configurations and are not intended to be limiting unless the context clearly states otherwise. For example, a prosthetic valve can be described as being placed in a "delivery configuration," which may be any suitable configuration that allows or enables delivery of the prosthetic valve. Examples of delivery configurations can include a compressed configuration, a folded configuration, a rolled configuration, and/or similar configuration or any suitable combinations thereof. Similarly, a prosthetic valve can be described as being placed in an "expanded configuration," which may be any suitable configuration that is not expressly intended for delivery of the prosthetic valve. Examples of expanded configuration can include a released configuration, a relaxed configuration, a deployed configuration, a non-delivery configuration, and/or similar configurations or any suitable combinations thereof. Some prosthetic valves described herein and/or components or features thereof can have a number of additional configurations that can be associated with various modes, levels, states, and/or portions of actuation, deployment, engagement, etc. Examples of such configurations can include an actuated configuration, a seated configuration, a secured configuration, an engaged configuration, and/or similar configurations or any suitable combinations thereof. While specific examples are provided above, it should be understood that they are not intended to be an exhaustive list of configurations. Other configurations may be possible. Moreover, various terms can be used to describe the same or substantially similar configurations and thus, the use of particular terms are not intended to be limiting and/or to the exclusion of other terms unless the terms and/or configurations are mutually exclusive, or the context clearly states otherwise.

Any of the disclosed valve embodiments may be delivered via traditional transcatheter delivery techniques or via orthogonal delivery techniques. For example, traditional delivery of prosthetic valves can be such that a central cylinder axis of the valve is substantially parallel to a length-wise axis of a delivery catheter used to deliver the valve. Typically, the valves are compressed in a radial direction relative to the central cylinder axis and advanced through the lumen of the delivery catheter. The valves are deployed from the end of the delivery catheter and expanded outwardly in a radial direction from the central cylinder axis. The delivery orientation of the valve generally means that the valve is completely released from the delivery catheter while in the atrium of the heart and reoriented relative to the annulus, which in some instances, can limit a size of the valve.

As used herein the terms "side-delivered," "side-delivery," "orthogonal delivery," "orthogonally delivered," and/or so forth can be used interchangeably to describe such a delivery method and/or a valve delivered using such a method. Orthogonal delivery of prosthetic valves can be such that the central cylinder axis of the valve is substantially orthogonal to the length-wise axis of the delivery catheter. With orthogonal delivery, the valves are compressed (or otherwise reduced in size) in a direction substantially parallel to the central cylinder axis and/or in a lateral direction relative to the central cylinder axis. As such, a length-wise axis (e.g., a longitudinal axis) of an orthogonally delivered valve is substantially parallel to the length-wise axis of the delivery catheter. In other words, an orthogonally delivered prosthetic valve is compressed and/or delivered at a roughly 90-degree angle compared to traditional processes of compressing and delivering transcatheter prosthetic valves. Moreover, in some instances, the orientation of orthogonally delivered valves relative to the annulus can allow a distal portion of the valve to be at least partially inserted into the annulus of the native heart valve while the proximal portion of the valve, at least in part, remains in the delivery catheter, thereby avoiding at least some of the size constraints faced with some know traditional delivery techniques.

Examples of prosthetic valves configured to be orthogonally delivered and processes of delivering such valves are described in detail in U.S. Patent Publication No. 2020/0188097, filed Dec. 11, 2019, entitled "Compressible Bileaflet Frame for Side Delivered Transcatheter Heart Valve" ("the '097 publication"); International Patent Publication No. WO 2020/061331, filed Sep. 19, 2019, entitled "Transcatheter Deliverable Prosthetic Heart Valves and Method of Delivery" ("the '331 WIPO publication"); International Patent Publication No. WO 2020/131978, filed Dec. 18, 2019, entitled "Transcatheter Deliverable Prosthetic Heart Valves and Methods of Delivery" ("the '978 WIPO publication"); International Patent Publication No. WO 2020/154734, filed Jan. 27, 2020, entitled "Collapsible Inner Flow Control Component for Side-Deliverable Transcatheter Heart Valve Prosthesis" ("the '734 WIPO publication"); International Patent Publication No. WO 2020/227249, filed May 4, 2020, entitled "Cinch Device and Method for Deployment of a Side-Delivered Prosthetic Heart Valve in a Native Annulus" ("the '249 WIPO publication"); International Patent Application Serial No. PCT/US2020/045195, filed Aug. 6, 2020, entitled "Side-Deliverable Transcatheter Prosthetic Valves and Methods for Delivering and Anchoring the Same" ("the '195 PCT application"); and/or International Patent Application Serial No. PCT/US2020/047162, filed Aug. 20, 2020, entitled "Delivery and Retrieval Devices and Methods for Side-Deliverable Transcatheter Prosthetic Valves" ("the '162 PCT application"), the disclosure of each of which is incorporated herein by reference in its entirety.

Mathematically, the term "orthogonal" refers to an intersecting angle of 90 degrees between two lines or planes. As used herein, the term "substantially orthogonal" refers to an intersecting angle of 90 degrees plus or minus a suitable tolerance. For example, "substantially orthogonal" can refer to an intersecting angle ranging from 75 to 105 degrees.

The embodiments herein, and/or the various features or advantageous details thereof, are explained more fully with reference to the non-limiting embodiments that are illustrated in the accompanying drawings and detailed in the following description. Descriptions of well-known components and processing techniques are omitted so as to not unnecessarily obscure the embodiments herein. Like numbers refer to like elements throughout.

The examples and/or embodiments described herein are intended to facilitate an understanding of structures, functions, and/or aspects of the embodiments, ways in which the embodiments may be practiced, and/or to further enable those skilled in the art to practice the embodiments herein. Similarly, methods and/or ways of using the embodiments described herein are provided by way of example only and not limitation. Specific uses described herein are not provided to the exclusion of other uses unless the context expressly states otherwise. For example, any of the prosthetic valves described herein can be used to replace a native valve of a human heart including, for example, a mitral valve, a tricuspid valve, an aortic valve, and/or a pulmonary valve. While some prosthetic valves are described herein in the context of replacing a native mitral valve or a native tricuspid valve, it should be understood that such a prosthetic valve can be used to replace any native valve unless expressly stated otherwise or unless one skilled in the art would clearly recognize that one or more components and/or features would otherwise make the prosthetic valve incompatible for such use. Accordingly, specific examples, embodiments, methods, and/or uses described herein should not be construed as limiting the scope of the inventions or inventive concepts herein. Rather, examples and embodiments are provided so that this disclosure will be thorough and complete, and will fully convey the scope of the inventive concepts to those skilled in the art.

FIGS. 1-5 are various schematic illustrations of a side-deliverable transcatheter prosthetic heart valve 100 (also referred to herein as "prosthetic valve" or simply "valve") according to an embodiment. The prosthetic valve 100 is configured to be deployed in a desired location within a body (e.g., of a human patient) and to permit blood flow in a first direction through a flow control component from an inflow end of the prosthetic valve 100 to an outflow end of the prosthetic valve 100 and to block blood flow in a second direction, opposite the first direction. For example, the prosthetic valve 100 can be configured to be deployed within the annulus of a native tricuspid valve or native mitral valve of a human heart to supplement and/or replace the functioning of the native valve.

The prosthetic valve 100 is compressible and expandable between an expanded configuration (FIGS. 1, 3, and 5) for implanting at a desired location in a body (e.g., a human heart) and a compressed or delivery configuration (FIGS. 2 and 4) for introduction into the body using a delivery catheter. For example, the prosthetic valve 100 can be compressible and expandable in at least one direction relative to a long-axis 102 of the valve 100 (also referred to herein as "horizontal axis," "longitudinal axis," or "length-wise axis"). In some embodiments, the prosthetic valve 100 can be compressible and expandable in at least two directions relative to the long-axis 102 of the valve 100.

In some embodiments, the valve 100 (and/or at least a portion thereof) may be heat-shaped and/or otherwise formed into any desired shape such as, for example, a roughly tubular shape, a roughly hourglass shape, and/or the like. In some embodiments, the valve 100 can include an upper atrial cuff or flange for atrial sealing, a lower ventricle cuff or flange for ventricular sealing, and a transannular section or region (e.g., a body section, a tubular section, a cylindrical section, etc.) disposed therebetween. The transannular region can have an hourglass cross-section for about 60-80% of the circumference to conform to the native annulus along the posterior and anterior annular segments while remaining substantially vertically flat along 20-40% of the annular circumference to conform to the septal annular segment. While the valve 100 is shown in FIGS. 1-5 as having a given shape, it should be understood that the size and/or shape of the valve 100 (and/or at least a portion thereof) can be based on a size and/or shape of the anatomical structures of the native tissue.

For example, the valve 100 can be centric (e.g., radially symmetrical relative to a central y-axis 104) or eccentric (e.g., radially asymmetrical relative to the central y-axis axis 104). In some eccentric embodiments, the valve 100, or an outer frame thereof, may have a complex shape determined by the anatomical structures where the valve 100 is being mounted. For example, in some instances, the valve 100 may be deployed in an annulus of a native tricuspid valve having a circumference in the shape of a rounded ellipse with a substantially vertical septal wall, which is known to enlarge in disease states along an anterior-posterior line. In some instances, the valve 100 may be deployed in an annulus of a native mitral valve (e.g., near the anterior leaflet) having a circumference in the shape of a rounded ellipse with a substantially vertical septal wall, which is known to enlarge in disease states. As such, the valve 100 can have a complex shape that determined, at least in part, by the native annulus and/or a disease state of the native valve. By way of example, the valve 100 or the outer frame thereof may have a D-shape (viewed from the top) so the flat portion can be matched to the anatomy in which the valve 100 will be deployed (e.g., a substantially vertical septal wall). In some embodiments, the valve 100 or the outer frame thereof can have a circumference in the shape of a rounded ellipse, such as a hyperbolic paraboloid, to account for the positions of native septal, anterior, and/or posterior leaflets, and/or the native septal wall; to avoid native electrical bundles such as the atrioventricular (A-V) node and/or A-V node-related structures like the Triangle of Koch, AV bundle, etc.; to avoid interference with coronary blood flow such as the coronary sinus; to accommodate variances in the septal wall that is known to be substantially vertical but that enlarges along the Anterior-Posterior axis toward the free wall in disease states.

As shown, the valve 100 generally includes an annular support frame 110 and a flow control component 150 mounted within the annular support frame 110. In addition, the valve 100 and/or at least the annular support frame 110 of the valve 100 can include, couple to, and/or otherwise engage a delivery system 180. In some implementations, the valve 100 and/or aspects or portions thereof can be similar to and/or substantially the same as the valves (and/or the corresponding aspects or portions thereof) described in detail in the '097 publication, the '331 WIPO publication, the '978 WIPO publication, the '734 WIPO publication, the '249 WIPO publication, the '195 PCT application, and/or the '162 PCT application incorporated by reference hereinabove. Accordingly, certain aspects, portions, and/or details of the valve 100 may not be described in further detail herein.

The annular support frame 110 (also referred to herein as "tubular frame," "valve frame," "wire frame," "outer frame," or "frame") can have a supra-annular region 120, a subannular region 130, and a transannular region 112, disposed and/or coupled therebetween. In some embodiments, the frame 110 can be monolithically and/or unitarily constructed. In some embodiments, one or more of the supra-annular region 120, the subannular region 130, and/or the transannular region 112 can be separate, independent, and/or modular components that are coupled to collectively form the frame 110. For example, in some embodiments, the supra-annular region 120 can be, for example, an atrial collar or cuff coupled to a top, upper, and/or supra-annular edge of the transannular region 112 and the subannular region 130 can be a bottom, lower, and/or subannular portion or section of the transannular region 112 of the fame 110.

In some implementations, a modular and/or at least partially modular configuration can allow the frame 110 to be adapted to a given size and/or shape of the anatomical structures where the valve 100 is being mounted. For example, one or more of the supra-annular region(s) 120, the subannular region 130, and/or the transannular region 112 can be designed and/or adapted so that that the support frame 110 has any desirable height, outer diameter, and/or inner diameter such as any of those described above. Moreover, such a modular configuration can allow the frame 110 to bend, flex, compress, fold, roll, and/or otherwise reconfigure without plastic or permanent deformation thereof. For example, the frame 110 is compressible to a compressed or delivery configuration for delivery and when released it is configured to return to its original shape (uncompressed, expanded, or released configuration) substantially without plastic or permanent deformation.

The support frame 110 and/or the supra-annular region 120, sub annular region 130, and/or transannular region 112 can be formed from or of any suitable material. In some embodiments, the frame 110 and/or one or more portions or regions thereof can be formed from or of a shape-memory or superelastic metal, metal alloy, plastic, and/or the like. For example, the frame 110 (e.g., one or more of the supra-annular region 120, the subannular region 130, and the transannular region 112) can be formed from or of Nitinol or the like. In some embodiments, the frame 110 (and/or any of the regions thereof) can be laser cut from a Nitinol sheet or tube. In other embodiments, the frame 110 (and/or any of the regions thereof) can be formed of or from a Nitinol wire that is bent, kink, formed, and/or manipulated into a desired shape. In still other embodiments, the frame 110 (and/or any of the regions thereof) can be formed of or from a desired material using any suitable additive or subtractive manufacturing process such as those described above. Moreover, the frame 110 and/or one or more of the supra-annular region 120, the subannular region 130, and the transannular region 112 can be formed of or from a metal or other structural frame material, which in turn, is covered by a biocompatible material such as, for example, pericardium tissue (e.g., DuraGuard®, Peri-Guard®, VascuGuard®, etc.), polymers (e.g., polyester, Dacron®, etc.), and/or the like, as described above.

The supra-annular region 120 of the frame 110 can be and/or can form, for example, a cuff or collar that can be attached or coupled to an upper edge or upper portion of the transannular region 112. When the valve 100 is deployed within a human heart, the supra-annular region 120 can be an atrial collar that is shaped to conform to the native deployment location. In a tricuspid and/or mitral valve replacement, for example, the supra-annular region 120 (e.g., atrial collar) can have various portions configured to conform to the native valve and/or a portion of the atrial floor surrounding the tricuspid and/or mitral valve, respectively. In some implementations, the supra-annular region 120 can be deployed on the atrial floor to direct blood from the atrium into the flow control component 150 of the valve 100 and to seal against blood leakage (perivalvular leakage) around the frame 110.

In some embodiments, the supra-annular region 120 can be a wire frame that is laser cut out of any suitable material. In some embodiments, the supra-annular region 120 can be formed from a tube or sheet of a shape-memory or superelastic material such as, for example, Nitinol and, for example, heat-set into a desired shape and/or configuration. In some embodiments, forming the supra-annular region 120 in such a manner can allow the supra-annular region 120 to bend, flex, fold, compress, and/or otherwise reconfigure substantially without plastically deforming and/or without fatigue that may result in failure or breaking of one or more portions thereof. Moreover, the wire frame of the supra-annular region 120 can be covered by any suitable biocompatible material such as any of those described above.

The supra-annular region 120 includes a distal portion and a proximal portion. In some embodiments, the distal portion can be and/or can include a distal supra-annular anchoring element and/or the like that can engage supra-annular native tissue on a distal side of the annulus as the prosthetic valve 100 is seated into the annulus. In some embodiments, the proximal portion can be and/or can include a proximal supra-annular anchoring element and/or the like that can engage supra-annular native tissue on a proximal side of the annulus as the prosthetic valve 100 is seated in the annulus. In some embodiments, the distal portion and/or the distal supra-annular anchoring element can be sized and/or shaped to correspond to a size and/or shape of the distal portion of the atrial floor of the heart in which the prosthetic valve 100 is disposed. Similarly, the proximal portion and/or the proximal supra-annular anchoring element can be sized and/or shaped to correspond to a size and/or shape of a proximal portion of the atrial floor of the heart.

Although not shown in FIGS. 1-5, the supra-annular region 120 can be shaped and/or formed to include any number of features configured to engage native tissue and/or one or more other portions of the valve 100, the delivery system 180, and/or the like. For example, in some embodiments, the supra-annular region 120 can include and/or can form an outer portion and an inner portion that is suspended from and/or coupled to the outer portion. In some implementations, the outer portion can be sized and/or shaped to engage native tissue, the inner portion can provide structure for mounting the flow control component 150 to the support frame 110, and one or more coverings, spacers, struts, splines, and/or structures can be disposed therebetween. In some implementations, a portion of the supra-annular region 120 can be at least temporarily coupled to and/or can at least temporarily receive a portion of the delivery system 180, at least a portion of an actuator, at least a portion of a guidewire, and/or the like.

The transannular region 112 of the support frame 110 is coupled to the supra-annular region 120 and extends from the supra-annular region 120 and at least partially through the annulus of the native valve when the prosthetic valve 100 is seated therein. In some embodiments, the transannular region 112 can be coupled to the supra-annular region 120 such that a desired amount of movement and/or flex is allowed therebetween (e.g., welded, bonded, sewn, bound, and/or the like). For example, in some implementations, the transannular region 112 and/or portions thereof can be sewn to the supra-annular region 120 (and/or portions thereof).

The transannular region 112 can be shaped and/or formed into a ring, a cylindrical tube, a conical tube, D-shaped tube, and/or any other suitable annular shape. In some embodiments, the transannular region 112 may have a side profile of a flat-cone shape, an inverted flat-cone shape (narrower at top, wider at bottom), a concave cylinder (walls bent in), a convex cylinder (walls bulging out), an angular hourglass, a curved, graduated hourglass, a ring or cylinder having a flared top, flared bottom, or both. Moreover, the transannular region 112 can form and/or define an aperture or central channel 114 that extends along the central axis 104 (e.g., the y-axis). The central channel 114 (e.g., a central axial lumen or channel) can be sized and configured to receive the flow control component 150 across at least a portion of a diameter of the central channel 114. In some embodiments, the transannular region 112 can have a shape and/or size that is at least partially based on a size, shape, and/or configuration of the supra-annular region 120 (and/or subannular region 130) and/or the native annulus in which it is configured to be deployed. For example, the transannular region 112 can have an outer circumference surface for engaging native annular tissue that may be tensioned against an inner aspect of the native annulus to provide structural patency to a weakened native annular ring.

In some embodiments, the transannular region 112 can be a wire frame that is laser cut out of any suitable material. For example, the transannular region 112 can be formed from a tube or sheet of a shape-memory or superelastic material such as, for example, Nitinol and, for example, heat-set into a desired shape and/or configuration. Although not shown in FIGS. 1-5, in some embodiments, the transannular region 112 can include and/or can be formed with two laser cut halves that can be formed into a desired shape and/or configuration and coupled together to form the transannular region 112. The transannular region 112 can be formed to include a set of compressible wire cells having an orientation and/or cell geometry substantially orthogonal to the central axis 104 (FIG. 1) to minimize wire cell strain when the transannular region 112 is in a vertical compressed configuration, a rolled and compressed configuration, or a folded and compressed configuration. In some embodiments, forming the transannular region 112 in such a manner can allow the transannular region 112 to bend, flex, fold, deform, and/or otherwise reconfigure (substantially without plastic deformation and/or undue fatigue) in response to lateral folding along or in a direction of a lateral axis 106 (FIG. 3) and/or vertical compression along or in a direction of the central axis 104 (FIG. 4), as described in further detail herein.

As described above with reference to the supra-annular region 120, the wire frame of the transannular region 112 can be covered by any suitable biocompatible material such as any of those described above. In some implementations, the wire frame of at least the supra-annular region 120 and transannular region 112 can be flexibly coupled (e.g., sewn) to form a wire frame portion of the support frame 110, which in turn, is covered in the biocompatible material. Said another way, at least the supra-annular region 120 and the transannular region 112 can be covered with the biocompatible material prior to being coupled or after being coupled. In embodiments in which the wire frames are covered after being coupled, the biocompatible material can facilitate and/or support the coupling therebetween.

The subannular region 130 of the frame 110 can be and/or can form, for example, a cuff or collar along an end of the transannular region 112 opposite the supra-annular region 120. In some embodiments, the subannular region 130 is a lower or subannular portion of the transannular region 112 (e.g., the transannular region 112 and the subannular region 130 are monolithically and/or unitarily formed). Said another way, a lower or subannular portion of the transannular region 112 can form and/or include the subannular annular region 130. In other embodiments, the subannular region 130 is a separate and/or independent component that can be attached or coupled to a lower edge or portion of the transannular region 112, as described above with reference to the supra-annular region 120. In such embodiments, for example, the subannular region 130 can be a wire frame that is laser cut out of any suitable material such as a shape-memory or superelastic material like Nitinol, heat-set into a desired shape and/or configuration, covered by any suitable biocompatible material, and attached to a lower edge of the transannular region 112, as described above with reference to the supra-annular region. In some implementations, forming the subannular region 130 in such a manner can allow the subannular region 130 to bend, flex, fold, compress, and/or otherwise reconfigure substantially without plastically deforming and/or without fatigue that may result in failure or breaking of one or more portions thereof.

When the valve 100 is deployed within a human heart, the subannular region 130 can be and/or can form a ventricular collar that is shaped to conform to the native deployment location. In a tricuspid and/or mitral valve replacement, for example, the subannular region 130 or collar can have various portions configured to conform to the native valve and/or a portion of the ventricular ceiling surrounding the tricuspid and/or mitral valve, respectively. In some implementations, the subannular region 130 or at least a portion thereof can engage the ventricular ceiling surrounding the native annulus to secure the valve 100 in the native annulus, to stabilize the valve 100 in the annulus, to prevent dislodging of the valve 100, to sandwich or compress the native annulus or adjacent tissue between the supra-annular region 120 and the subannular region 130 (or lower portion of the transannular region 112), and/or to seal against blood leakage (perivalvular leakage and/or regurgitation during systole) around the frame 110.

The subannular region 130 of the frame 110 can be shaped and/or formed to include any number of features configured to engage native tissue, one or more other portions of the valve 100, one or more portions of the delivery system 180, one or more actuators (not shown), and/or the like. For example, as shown in FIG. 1, the subannular region 130 can include and/or can form a distal portion having a distal anchoring element 132, a proximal portion having a proximal anchoring element 134, and a septal portion having a septal stability and/or anchoring element. In some embodiments, the subannular region 130 can include and/or can form any number of additional anchoring elements (not shown in FIGS. 1-5). In some embodiments, the anchoring elements 132, 134, and/or 136 are integrally and/or monolithically formed with the subannular region 130 and/or the lower or subannular portion of the transannular region 112. The distal anchoring element 132 and the proximal anchoring element 134 can be any suitable shape, size, and/or configuration such as any of those described in detail in the '097 publication, the '331 WIPO publication, the '978 WIPO publication, the '734 WIPO publication, the '249 WIPO publication, the '195 PCT application, and/or the '162 PCT application incorporated by reference hereinabove, and/or any of those described herein with respect to specific embodiments. Accordingly, portions, aspects, and/or features of the distal anchoring element 132 and/or the proximal anchoring element 134 may not be described in further detail herein.

In some embodiments, the distal anchoring element 132 can optionally include a guidewire coupler 133 configured to selectively engage and/or receive a portion of a guidewire or a portion of a guidewire assembly (not shown). The guidewire coupler 133 is configured to allow a portion of the guidewire to extend through an aperture of the guidewire coupler 133, thereby allowing the valve 100 to be advanced over or along the guidewire during delivery and deployment. In some embodiments, the guidewire coupler 133 can selectively allow the guidewire to be advanced therethrough while blocking or preventing other elements and/or components such as a pusher or the like.

The distal anchoring element 132 is configured to engage a desired portion of the native tissue on a distal side of the native annulus to facilitate the seating, mounting, and/or deploying of the valve 100 in the annulus of the native valve. For example, in some implementations, the distal anchoring element 132 can be a projection or protrusion extending from the frame 110 (e.g., the subannular region 130 and/or the lower portion of the transannular region 112) and into a distal subannular position relative to the annulus (e.g., the RVOT for tricuspid valve replacement, and/or the like). In such implementations, the distal anchoring element 132 can be shaped and/or biased such that the distal anchoring element 132 exerts a force on the subannular tissue operable to at least partially secure, stabilize, and/or anchor the distal end portion of the valve 100 in the native annulus. In some embodiments, the distal anchoring element 132 can extend from the distal portion of the subannular region 130 (or lower portion of the transannular region 112) by about 10-40 mm.

The proximal anchoring element 134 is configured to engage subannular tissue on a proximal side of the native annulus to facilitate the seating, mounting, and/or deploying of the valve 100 in the annulus. In some embodiments, the proximal anchoring element 134 can be an anchoring element having a substantially fixed configuration. In such embodiments, the proximal anchoring element 134 can be flexible and/or movable through a relatively limited range of motion but otherwise has a single configuration. In some such embodiments, the proximal anchoring element 134 can extend from the proximal portion of the subannular region 130 (or lower portion of the transannular region 112) by about 10-40 mm.

In other embodiments, the proximal anchoring element 134 can be configured to transition, move, and/or otherwise reconfigure between two or more configurations. For example, the proximal anchoring element 134 can be transitioned between a first configuration in which the proximal anchoring element 134 extends from the subannular region 130 a first amount or distance and a second configuration in which the proximal anchoring element 134 extends from the subannular region 130 a second amount or distance, different from the first amount or distance. For example, in some embodiments, the proximal anchoring element 134 can have a first configuration in which the proximal anchoring element 134 is in a compressed, contracted, retracted, undeployed, folded, and/or restrained state (e.g., in a position that is near, adjacent to, and/or in contact with the transannular region 112 and/or the supra-annular region 120 of the frame 110), and a second configuration in which the proximal anchoring element 134 is in an expanded, extended, deployed, unfolded, and/or unrestrained state (e.g., extending away from the transannular region 112). In some implementations, the proximal anchoring element 134 in the expanded or deployed configuration (e.g., the second configuration) can extend from the transannular region 112 by about 10-40 mm and in the compressed or undeployed configuration (e.g., the first configuration) can be in contact with the transannular region 112 or can extend from the transannular region 112 by less than about 10 mm. Moreover, in some implementations, the proximal anchoring element 134 can be transitioned from the first configuration to the second configuration in response to actuation of an actuator, tensile member, portion of the delivery system 180, and/or the like, as described in further detail herein.

The frame 110 also includes the septal stability and/or anchoring element 136 (also referred to herein as "septal anchoring element"). The septal anchoring element 136 can be any suitable shape, size, and/or configuration such as any of those described herein with respect to specific embodiments. In some embodiments, for example, the septal anchoring element 136 can be, for example, integrally formed with the lower sidewall portion 130 of the frame 110 (e.g., can be a portion of the wireframe or laser-cut frame portion). In some embodiments, the septal anchoring element 136 can be formed at least in part by a wire-braid frame, a wire loop, an integrated frame section, a stent, and/or the like and can extend away from the transannular region 112 and/or the supra-annular region 120 (e.g., downward and outward).

The septal anchoring element 136 can be positioned along the septal side of the subannular region 130 (or lower portion of the transannular region 112) at any suitable position. For example, in some embodiments, the septal anchoring element 136 can be a wire frame or the like have a U-shape, an inverted parabolic shape, and/or the like such that a local minima of the septal anchoring element 136 is substantially centered along the septal side of the subannular region 130. In other embodiments, the septal anchoring element 136 can have the U-shape, the inverted parabolic shape, and/or the like but can be shifted in a proximal direction or in a distal direction (e.g., closer to the proximal anchoring element 132 and further from the distal anchoring element 134, or vice versa). In some embodiments, the septal anchoring element 136 can be substantially symmetric relative to an anteroposterior (AP) plane. In other embodiments, the septal anchoring element 136 can be asymmetric relative to the AP plane. In some embodiments, the septal anchoring element 136 can have an irregular or an at least semi-irregular shape that can be based, for example, on the anatomy of the heart in which the valve 100 is disposed. In some embodiments, the septal anchoring element 136 can extend from the septal portion of the subannular region 130 (or lower portion of the transannular region 112) by about 10-40 mm.

In some implementations, the septal anchoring element 136 is a lower anchoring element configured to engage subannular tissue of the ventricle to aid in the stability, anchoring, and/or securement of the valve 100 in the annulus. More specifically, the septal anchoring element 136 can be configured to engage subannular septal tissue, septal leaflet tissue, and/or any other suitable tissue at, near, and/or along the septum of the heart. In some implementations, when the valve 100 is at least partially inserted into the annulus, the septal anchoring element 136 can extend down the septal wall to pin the native septal leaflet away from, for example, the coapting leaflets of the prosthetic valve 100. In some implementations, the septal anchoring element can stabilize the valve against any intra-annular rolling forces and/or any intra-annular twisting forces that might affect a desired location or positioning of the prosthetic valve within the annulus, (e.g., tilted, angled, twisted, rolled, etc.). In some embodiments, the septal anchoring element 136 can be size, shaped, and/or configured for treating specific anatomical structures, avoiding interference with native electrical tissue or with the coronary sinus return, avoiding excessive cutting effect on the ventricular tissue, blocking native tissue from interfering with the functioning of the prosthetic valve 100 (e.g., leaflets of the flow control component 150), providing additional ventricular stability to prevent unwanted movement of the prosthetic valve 100 prior to in-growth, such as rolling, tilting, twisting or other unwanted migration of the implant, and/or the like.

As described above with reference to the proximal anchoring element 134, the septal anchoring element 136 can be an anchoring element that has a substantially fixed configuration or can be an anchoring element that can be reconfigurable between any number of configurations. For example, in some embodiments, the septal anchoring element 136 can be configured to transition, move, and/or otherwise reconfigure between a first configuration in which the septal anchoring element 136 extends from the subannular region 130 a first amount or distance and a second configuration in which the septal anchoring element 136 extends from the subannular region 130 a second amount or distance, different from the first amount or distance. In some implementations, the septal anchoring element 136 can be compressed, contracted, retracted, undeployed, folded, and/or restrained when in the first configuration (e.g., in a position that is near, adjacent to, and/or in contact with the transannular region 112 and/or the supra-annular region 120 of the frame 110), and can be expanded, extended, deployed, unfolded, actuated, and/or unrestrained when in the second configuration (e.g., extending away from the transannular region 112). Moreover, in some implementations, the septal anchoring element 136 can be transitioned from the first configuration to the second configuration in response to actuation of an actuator, tensile member, portion of the delivery system 180, and/or the like, as described in further detail herein.

Although not shown in FIGS. 1-5, the frame 110 may also have and/or form additional functional elements (e.g., loops, anchors, etc.) for attaching accessory components such as biocompatible covers, tissue anchors, releasable deployment and retrieval controls (e.g., an actuator, a tensile member, a portion of the delivery system 180, and/or other suitable guides, knobs, attachments, rigging, etc.) and so forth. In some implementations, the frame 110 (or aspects and/or portions thereof) can be structurally and/or functionally similar to the frames (or corresponding aspects and/or portions thereof) described in detail in the '097 publication, the '331 WIPO publication, the '978 WIPO publication, the '734 WIPO publication, the '249 WIPO publication, the '195 PCT application, and/or the '162 PCT application incorporated by reference hereinabove.

The flow control component 150 can refer in a non-limiting sense to a device for controlling fluid flow therethrough. In some embodiments, the flow control component 150 can be a leaflet structure having two, three, four, or more leaflets, made of flexible biocompatible material such a treated or untreated pericardium. The leaflets can be sewn or joined to a support structure such as an inner frame, which in turn, can be sewn or joined to the outer frame 110. The leaflets can be configured to move between an open and a closed or substantially sealed state to allow blood to flow through the flow control component 150 in a first direction through an inflow end of the valve 100 and block blood flow in a second direction, opposite to the first direction, through an outflow end of the valve 100. For example, the flow control component 150 can be configured such that the valve 100 functions, for example, as a heart valve, such as a tricuspid valve, mitral valve, aortic valve, or pulmonary valve, that can open to blood flowing during diastole from atrium to ventricle, and that can close from systolic ventricular pressure applied to the outer surface. Repeated opening and closing in sequence can be described as "reciprocating."

The inner frame and/or portions or aspects thereof can be similar in at least form and/or function to the outer frame 110 and/or portions or aspects thereof. For example, the inner frame can be a laser cut frame formed from or of a shape-memory material such as Nitinol. Moreover, the inner frame can be compressible for delivery and configured to return to its original (uncompressed) shape when released (e.g., after delivery). In some embodiments, the inner frame can include and/or can form any suitable number of compressible, elastically deformable diamond-shaped or eye-shaped wire cells, and/or the like. The wire cells can have an orientation and cell geometry substantially orthogonal to an axis of the flow control component 150 to minimize wire cell strain when the inner frame is in a compressed configuration.

Figure 2:
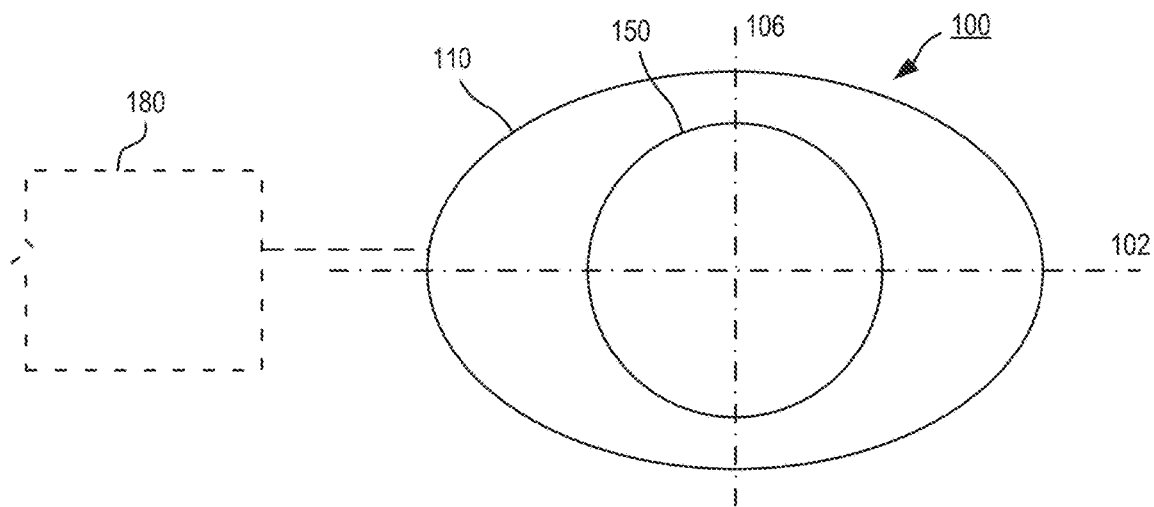
Figure 3:
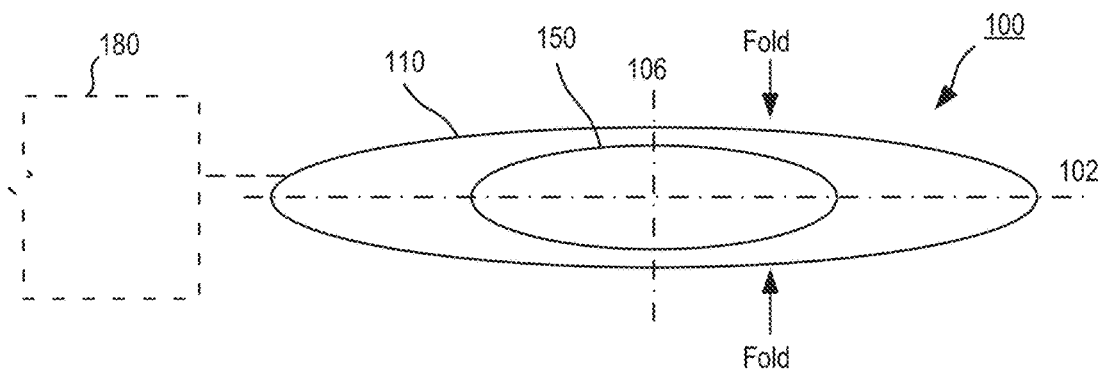
Figure 4:
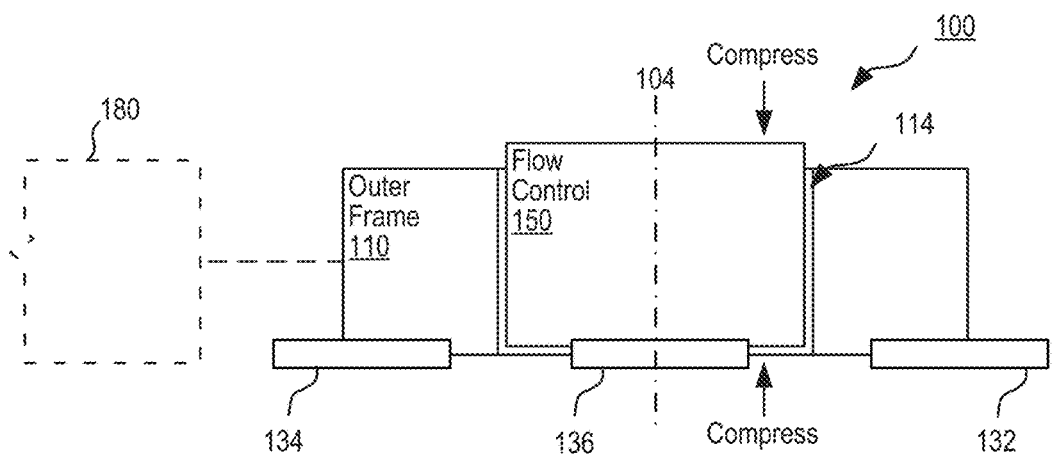

In some embodiments, the flow control component 150 and/or the inner frame thereof can have a substantially cylindrical or tubular shape when the valve 100 is in the expanded configuration (see e.g., FIG. 3) and can be configured to elastically deform when the valve 100 is placed in the compressed configuration (see e.g., FIGS. 2 and 4). Although not shown in FIGS. 1-5, in some embodiments, the inner frame of the flow control component 150 can include and/or can be formed with two halves that can be coupled together to allow the inner frame to elastically deform in response to lateral compression or folding along or in a direction of the lateral axis 106 (FIG. 3), as described in further detail herein.

As shown in FIGS. 1-4, the flow control component 150 is mounted within the central channel 114 of the frame 110. More specifically, the flow control component 150 is mounted and/or coupled to the supra-annular region 120 (e.g., an inner portion thereof) and is configured to extend into and/or through the central channel 114 formed and/or defined by the transannular region 112. In some embodiments, the flow control component 150 can be coupled to the supra-annular region 120 via tissue, a biocompatible mesh, one or more woven or knitted fabrics, one or more super-elastic or shape-memory alloy structures, which is sewn, sutured, and/or otherwise secured to a portion supra-annular region 120. In some embodiments, the flow control component 150 can be coupled to the supra-annular region 120 such that a portion of the flow control component 150 is disposed above and/or otherwise extends beyond the supra-annular region 120 (e.g., extends away from the annulus in the direction of the atrium). In some embodiments, the portion of the flow control component 150 extending above and/or beyond the supra-annular region 120 can form a ridge, ledge, wall, step-up, and/or the like. In some implementations, such an arrangement can facilitate ingrowth of native tissue over the supra-annular region 120 without occluding the flow control component 150.

The flow control component 150 can be at least partially disposed in the central channel 114 such that the axis of the flow control component 150 that extends in the direction of blood flow through the flow control component 150 is substantially parallel to the central axis 104 of the frame 110. In some embodiments, the arrangement of the support frame 110 can be such that the flow control component 150 is centered within the central channel 114. In other embodiments, the arrangement of the support frame 110 can be such that the flow control component 150 is off-centered within the central channel 114. In some embodiments, the central channel 114 can have a diameter and/or perimeter that is larger than a diameter and/or perimeter of the flow control component 150. Although not shown in FIGS. 1-5, in some embodiments, the valve 100 can include a spacer or the like that can be disposed within the central channel 114 adjacent to the flow control component 150. In other embodiments, a spacer can be a cover, or the like coupled to a portion of the frame 110 and configured to cover a portion of the central channel 114. In some instances, the spacer can be used to facilitate the coupling of the flow control component 150 to the frame 110.

In some embodiments, the flow control component 150 (or portions and/or aspects thereof) can be similar to, for example, any of the flow control components described in the '734 WIPO publication. Thus, the flow control component 150 and/or aspects or portions thereof are not described in further detail herein.

Referring back to FIG. 1, the valve 100 includes and/or is coupled to the delivery interface 180. In some embodiments, the valve 100 can also include an actuator and/or other suitable member, mechanism, and/or device configured to actuate at least a portion of the valve 100. For example, in some embodiments, the actuator can be configured to at least temporarily couple to the supra-annular region 120 of the support frame 110 and can be configured to actuate one or more portions of the valve 100 such as, for example, the proximal anchoring element 134 or the septal anchoring element 136. In some implementations, the actuator can include one or more cables, tethers, linkages, joints, connections, tensile members, etc., that can exert a force (or can remove an exerted force) on a portion of the proximal or septal anchoring elements 134 and/or 136 operable to transition the anchoring elements 134 and/or 136 between the first and second configuration.

The delivery system 180, shown in FIG. 1, can include any number of components having any suitable shape, size, and/or configuration. In some implementations, the delivery system 180 can be and/or can include, for example, at least a delivery catheter such as, for example, a 12-34 Fr delivery catheter with any suitable corresponding internal lumen diameter(s) sufficient to receive the prosthetic valve 100 in the compressed configuration, as described, for example, in any of the '097 publication, the '331 WIPO publication, the '978 WIPO publication, the '734 WIPO publication, the '249 WIPO publication, the '195 PCT application, and/or the '162 PCT application incorporated by reference hereinabove. In some embodiments, at least portion of the actuator or the like can extend through one or more lumens of the delivery catheter, thereby allowing a user (e.g., a doctor, surgeon, technician, etc.) to manipulate a distal end of the actuator and thus one or more portions of the valve 100. In some embodiments, a guidewire and/or guidewire assembly can similarly extend through one or more lumens of the delivery catheter. As described above, the distal anchoring element 132 can include a guidewire coupler 133 that can be coupled to and/or receive at least a portion of the guidewire and/or guidewire assembly and thus, the valve 100 can be advanced along the guidewire and/or guidewire assembly through the delivery system and into a desired position within the heart (e.g., the annulus of a native heart valve).

As described above, the valve 100 is compressible and expandable between the expanded configuration (FIGS. 1 and 2) and the compressed configuration (FIGS. 3 and 4). The valve 100 can have a first height or size along the central axis 104 when in the expanded configuration and can have a second height or size, less than the first height or size, along the central axis 104 when in the compressed configuration. The valve 100 can also be compressed in additional directions. For example, the valve 100 can be compressed along the lateral axis 106 that is perpendicular to both the longitudinal axis 102 and the central axis 104 (see e.g., FIGS. 2 and 3).

The valve 100 is compressed during delivery of the valve 100 and is configured to expand once released from the delivery catheter. More specifically, the valve 100 is configured for transcatheter orthogonal delivery to the desired location in the body (e.g., the annulus of a native valve), in which the valve 100 is compressed in an orthogonal or lateral direction relative to the dimensions of the valve 100 in the expanded configuration (e.g., along the central axis 104 and/or the lateral axis 106). During delivery, the longitudinal axis 102 of the valve 100 is substantially parallel to a longitudinal axis of the delivery catheter, as described in the '331 WIPO publication.

The valve 100 is in the expanded configuration prior to being loaded into the delivery system 180 and after being released from the delivery catheter and deployed or implanted (or ready to be deployed or implanted) at the desired location in the body. When in the expanded configuration shown in FIGS. 1, 2, and 5, the valve 100 has an extent in any direction orthogonal or lateral to the longitudinal axis 102 (e.g., along the central axis 104 and/or the lateral axis 106) that is larger than a diameter of the lumen of the delivery catheter used to deliver the valve 100. For example, in some embodiments, the valve 100 can have an expanded height (e.g., along the central axis 104) of 5-60 mm. In some embodiments, the valve 100 can have an expanded diameter length (e.g., along the longitudinal axis 102) and width (e.g., along the lateral axis 106) of about 20-80 mm, or about 40-80 mm.

When in the compressed configuration shown in FIGS. 3 and 4, the valve 100 has an extent in any direction orthogonal or lateral to the longitudinal axis 102 (e.g., along the central axis 104 and/or the lateral axis 106) that is smaller than the diameter of the lumen of the delivery catheter, allowing the valve 100 to be delivered therethrough. For example, in some embodiments, the valve 100 can have a compressed height (e.g., along the central axis 104) and a compressed width (e.g., along the lateral axis 106) of about 6-15 mm, about 8-12 mm, or about 9-10 mm. The valve 100 can be compressed by compressing, rolling, folding, and/or any other suitable manner, or combinations thereof, as described in detail in the '097 publication, the '331 WIPO publication, the '978 WIPO publication, the '734 WIPO publication, the '249 WIPO publication, the '195 PCT application, and/or the '162 PCT application incorporated by reference hereinabove. It is contemplated in some embodiments that the length of the valve 100 (e.g., along the longitudinal axis 102) is not compressed for delivery. Rather, in some embodiments, the length of the valve 100 can be increased in response to compression of the valve 100 along the central axis 104 and/or the lateral axis 106.

Figure 5:
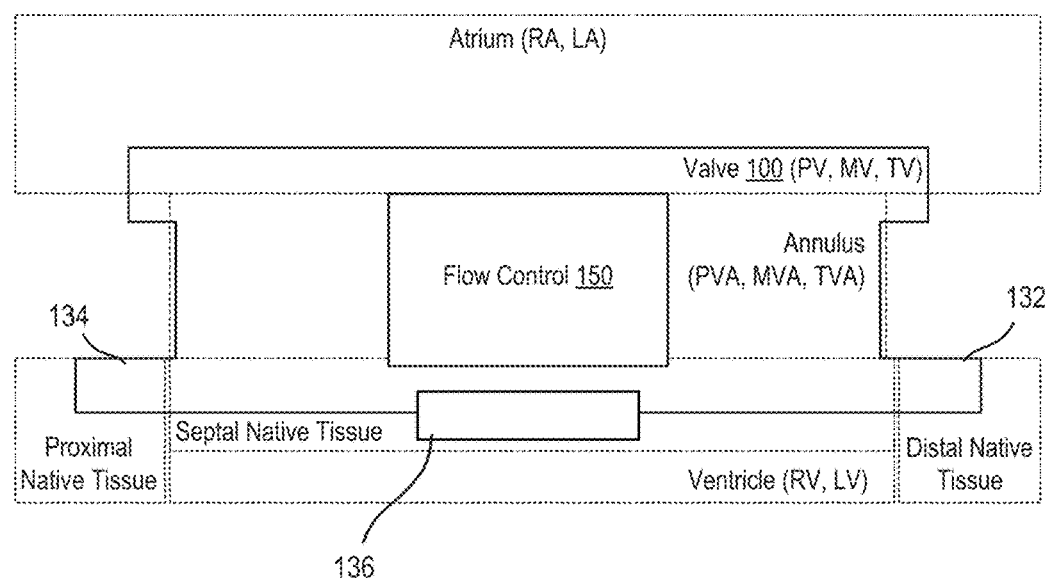

As shown in FIG. 5, the valve 100 can be delivered, for example, to an atrium of the human heart (or any other space or chamber of the human heart) and disposed within an annulus of a native valve such as, for example, the pulmonary valve (PV), the mitral valve (MV), the aortic valve (AV), and/or the tricuspid valve (TV). As described above, the valve 100 can be in the compressed configuration and delivered to the annulus via the delivery system 180 and can be released from the delivery system 180 and allowed to expand to the expanded configuration. For example, the valve 100 can be delivered to the atrium of the human heart and released from the delivery catheter (not shown) via any of the delivery systems, devices, and/or methods described in detail in the '097 publication, the '331 WIPO publication, the '978 WIPO publication, the '734 WIPO publication, the '249 WIPO publication, the '195 PCT application, and/or the '162 PCT application incorporated by reference hereinabove.

In some implementations, the delivery of the valve 100 can include advancing a guidewire into the atrium of the human heart, through the native valve, and to a desired position within the ventricle (e.g., the RVOT). After positioning the guidewire, the delivery catheter can be advanced along and/or over the guidewire and into the atrium (e.g., via the IVC, the SVC, and/or a trans-septal access). In some embodiments, a guidewire coupler 133 of the valve 100 (e.g., included in or on the distal anchoring element 132) can be coupled to a proximal end portion of the guidewire and the valve 100 can be placed in the compressed configuration, allowing the valve 100 to be advanced along the guidewire and through a lumen of the delivery catheter, and into the atrium.

The deployment of the valve 100 can include placing the distal anchoring element 132 of the subannular region 130 in the ventricle (RV, LV) below the annulus while the remaining portions of the valve 100 are in the atrium (RA, LA). In some instances, the distal anchoring element 132 can be advanced over and/or along the guidewire to a desired position within the ventricle such as, for example, an outflow tract of the ventricle. For example, in some implementations, the valve 100 can be delivered to the annulus of the native tricuspid valve (TV) and at least a portion of the distal anchoring element 132 can be positioned in the RVOT. In other implementations, the valve 100 can be delivered to the annulus of the native mitral valve (MV) and at least a portion of the distal anchoring element 132 can be positioned in a subannular position distal to the annulus and/or in any other suitable position in which the distal anchoring element 132 can engage native tissue, leaflets, chordae, etc.

In some implementations, the prosthetic valve 100 can be temporarily maintained in a partially deployed state. For example, the valve 100 can be partially inserted into the annulus and held at an angle relative to the annulus to allow blood to flow from the atrium to the ventricle partially through the native valve annulus around the valve 100, and partially through the valve 100, which can allow for assessment of the valve function.

The valve 100 can be placed or seated in the annulus (PVA, MVA, AVA, and/or TVA) of the native valve (PV, MV, AV, and/or TV) such that the subannular region 130 (e.g., a ventricular collar) is disposed in a subannular position, the transannular region 112 of the valve frame 110 extends through the annulus, and the supra-annular region 120 (e.g., a atrial collar) remains in a supra-annular position. For example, in some embodiments, the delivery system 180, the actuator, and/or any other suitable member, tool, etc. can be used to push at least the proximal end portion of the valve 100 into the annulus. In addition, the septal anchoring element 136 can be at least partially inserted through the annulus prior to the valve 100 being fully seated in the annulus. In some implementations, the septal anchoring element 136 can be in contact with, for example, subannular septal tissue (e.g., the native septal wall, a native septal leaflet, and/or the like) as the valve 100 is seated in the annulus, thereby providing stability during the seating process (e.g., rolling, twisting, rotating, and/or spinning about a distal-proximal axis of the valve 100 and/or about an axis associated with, for example, the guidewire or guidewire assembly extending along the longitudinal length of the valve 100.

In some implementations, the proximal anchoring element 134 can be maintained in its first configuration as the valve 100 is seated in the annulus. For example, as described above, the proximal anchoring element 134 can be in a compressed, contracted, and/or retracted configuration in which the proximal anchoring element 134 is in contact with, adjacent to, and/or near the transannular region 112 and/or the supra-annular region 120 of the frame 110, which in turn, can limit an overall circumference of the subannular region 130 of the frame 110, thereby allowing the subannular region 130 and the transannular region 112 of the frame 110 to be inserted into and/or through the annulus.

Once seated, the proximal anchoring element 134 can be transitioned from its first configuration to its second configuration, as described in detail in the '978 WIPO publication. For example, in some implementations, a user can manipulate a portion of the delivery system to actuate the actuator. In some implementations, actuating the actuator can release and/or reduce an amount of tension within or more tethers, cables, connections, and/or portions of the actuator, thereby allowing the proximal anchoring element 134 to transition. Accordingly, once the valve 100 is seated in the annulus, the proximal anchoring element 134 can be placed in its second configuration in which the proximal anchoring element 134 contacts, engages, and/or is otherwise disposed adjacent to subannular tissue. In some embodiments, the septal anchoring element 136 similarly can be transitioned from a first configuration to a second configuration. In some implementations, placing at least one of the proximal anchoring element 134 and/or the septal anchoring element 136 can reduce an extent (e.g., size or diameter) of the subannular region 130 or lower portion of the transannular region 112 to allow the valve 100 to be inserted into and at least partially through the annulus. In such implementations, once the valve 100 is at least partially seated in the annulus, the proximal anchoring element 134 and/or the septal anchoring element 136 can then be transitioned from the first (e.g., compressed) configuration(s) to the second (e.g., extended) configuration(s) to stabilize, anchor, and/or secure the valve 100 in the annulus of the native valve.

Although not shown in FIGS. 1-5, in some embodiments, any of the distal anchoring element 132, the proximal anchoring element 134, and/or the septal anchoring element 136 can be configured to selectively engage native tissue, chordae, trabeculae, annular tissue, leaflet tissue, and/or any other anatomic structures to aid in the securement of the valve 100 in the native annulus. For example, one or more of the anchoring elements 132, 134, and/or 136 can include any suitable feature, surface, member, etc. configured to facilitate the engagement between the anchoring elements 132, 134, and/or 136 and the native tissue. In some implementations, such features and/or members can engage and/or otherwise become entangled in the native tissue, chordae, trabeculae, annular tissue, leaflet tissue, and/or any other anatomic structures, thereby enhancing and/or facilitating the securement of the valve 100 in the annulus.

As described above, the distal anchoring element 132 can be configured to engage native tissue on a distal side of the annulus, the proximal anchoring element 134 can be configured to engage native tissue on a proximal side of the annulus (e.g., when in the second or expanded configuration), and the septal anchoring element 136 can be configured to engage native tissue of a septal side of the annulus (e.g., the septal wall or native septal leaflet tissue), thereby securely seating the valve 100 in the native annulus, as shown in FIG. 5. In some implementations, any other or additional portions of the valve 100 can similarly engage native tissue to securely seat the valve 100 in the native annulus and/or to form a seal between the support frame 110 and the tissue forming the native annulus (e.g., an anterior anchoring element can engage subannular tissue on an anterior side of the annulus, or the supra-annular region 120 can include any number of supra-annular anchoring elements for engaging supra-annular tissue (not shown in FIGS. 1-5)).

Figure 6:
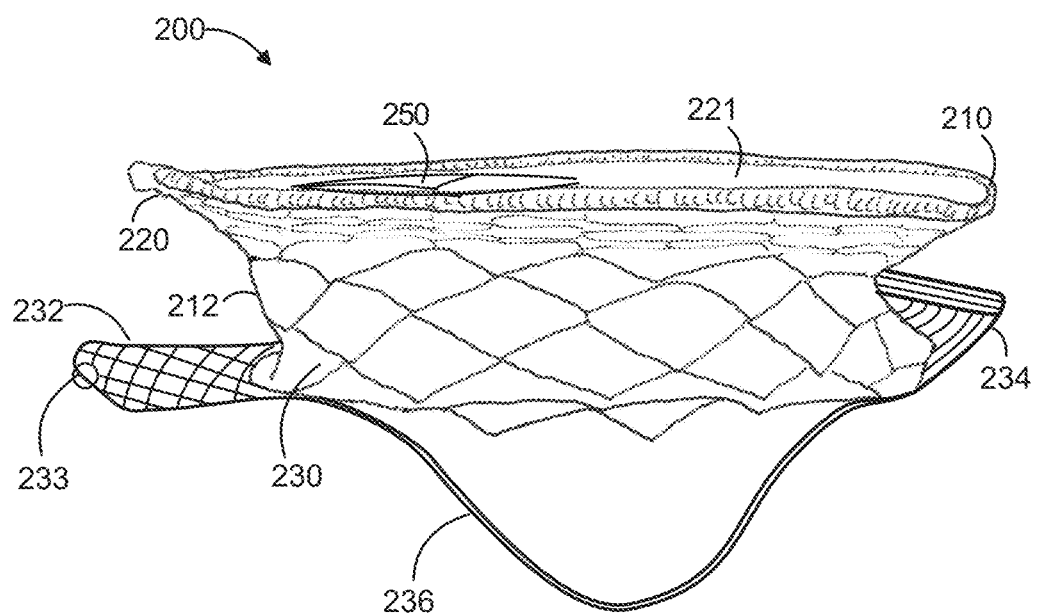
FIG. 6 is a side perspective view illustration of a side-deliverable transcatheter prosthetic valve having a valve frame with a septal area stability element, a distal anchoring element, and a proximal anchoring element, according to an embodiment.

FIG. 6 is a side perspective view illustration of a side-deliverable transcatheter prosthetic valve 200 (also referred to herein a "prosthetic valve" or simply "valve") according to an embodiment. The valve 200 can be any suitable shape, size, and/or configuration. For example, in some embodiments, the valve 200 can be similar in at least form and/or function to the valve 100 described above with reference to FIGS. 1-5.

As shown, the valve 200 generally includes an annular support frame 210 and a flow control component 250. In addition, the valve 200 and/or at least the annular support frame 210 of the valve 200 includes one or more anchoring element. For example, the annular support frame 210 can include at least a septal stability and/or anchoring element 236, a distal anchoring element 232 and a proximal anchoring element 234. In some implementations, the septal stability and/or anchoring element 236, the distal anchoring element 232 and the proximal anchoring element 234 can all be lower anchoring elements. In other embodiments, the valve 200 and/or the annular support frame 210 can include a distal upper anchoring element and a proximal upper anchoring element for atrial anchoring.

The annular support frame 210 (also referred to herein as "tubular frame," "valve frame," "wire frame," or "frame") can have or can define an aperture 214 that extends along a central axis. The aperture 214 (e.g., a central axial lumen) can be sized and configured to receive the flow control component 250 across a diameter of the aperture 214. The frame 210 may have an outer circumferential surface for engaging native annular tissue that may be tensioned against an inner aspect of the native annulus to provide structural patency to a weakened native annular ring.

The frame 210 includes a cuff or collar 220 (e.g., a supra-annular region) and a tubular or transannular section 212. The cuff or collar 220 (referred to herein as "collar") can be attached to and/or can form an upper edge of the frame 210. When the valve 200 is deployed within a human heart, the collar 220 can be an atrial collar. The collar 220 can be shaped to conform to the native deployment location. In a mitral replacement, for example, the collar 220 will be configured with varying portions to conform to the native valve. In one embodiment, the collar 220 will have a distal and proximal upper collar portion. The distal collar portion can be larger than the proximal upper collar portion to account for annular geometries, supra-annular geometries, and/or sub annular geometries.

The frame 210 may optionally have a separate atrial collar attached to the upper (atrial) edge of the frame 210, for deploying on the atrial floor that is used to direct blood from the atrium into the flow control component 250 and to seal against blood leakage (perivalvular leakage) around the frame 210. The frame 210 may also optionally have a separate ventricular collar (e.g., a subannular region) attached to the lower (ventricular) edge of the frame 210, for deploying in the ventricle immediately below the native annulus that is used to prevent regurgitant leakage during systole, to prevent dislodging of the valve 200 during systole, to sandwich or compress the native annulus or adjacent tissue against the atrial collar or collar 220, and/or optionally to attach to and support the flow control component 250. Some embodiments may have both an atrial collar and a ventricular collar, whereas other embodiments either include a single atrial collar, a single ventricular collar, or have no additional collar structure.

The frame 210 can be a ring, or cylindrical or conical tube, but may also have a side profile of a flat-cone shape, an inverted flat-cone shape (narrower at top, wider at bottom), a concave cylinder (walls bent in), a convex cylinder (walls bulging out), an angular hourglass, a curved, graduated hourglass, a ring or cylinder having a flared top, flared bottom, or both. The frame 210 may have a height in the range of about 5-60 mm, may have an outer diameter dimension, R, in the range of about 20-80 mm, and may have an inner diameter dimension in the range of about 21-79 mm, accounting for the thickness of the frame 210 (e.g., a wire material forming the frame 210).

The frame 210 is compressible for delivery and when released it is configured to return to its original (uncompressed) shape. The frame 210 may be compressed for transcatheter delivery and may be expandable using a transcatheter expansion balloon. In other implementations, the frame 210 can include and/or can be formed of a shape-memory element allowing the frame 210 to be self-expanding. In some instances, suitable shape-memory materials can include metals and/or plastics that are durable and biocompatible. For example, the frame 210 can be made from super elastic metal wire, such as a Nitinol wire or other similarly functioning material. The frame 210 may be constructed as a braid, wire, or laser cut wire frame. The frame 210 may also have and/or form additional functional elements (e.g., loops, anchors, etc.) for attaching accessory components such as biocompatible covers, tissue anchors, releasable deployment and retrieval control guides, knobs, attachments, rigging, and so forth.

As described above, the frame 210 and/or the valve 200 can include at least the distal anchoring element 232 and the proximal anchoring element 234. The distal and proximal anchoring elements 232 and 234 can be, for example, lower anchoring elements (e.g., coupled to and/or included in a lower portion or subannular region of the frame 210). In some embodiments, the frame 210 and/or the valve 200 can also optionally include one or more of a distal upper anchoring element and a proximal upper anchoring element. The anchoring elements 232 and 234 of the valve 200 can be configured to engage a desired portion of the annular tissue to mount the frame 210 to the annulus of the native valve in which the valve 200 is deployed, as described in further detail herein. The anchoring elements 232 and 234 of the valve 200 and/or the frame 210 can be any suitable shape, size, and/or configuration. Moreover, certain aspects, features, and/or configurations of at least the distal and proximal anchoring elements 232 and 234 are described below reference to specific embodiments.

The frame 210 can also include the septal stability and/or anchoring element 236 (also referred to herein as "septal anchoring element"). The septal anchoring element 236 can be any suitable shape, size, and/or configuration such as any of those described herein with respect to specific embodiments. In some embodiments, for example, the septal anchoring element 236 can be, for example, integrally formed with the lower sidewall portion 230 of the frame 210 (e.g., can be a portion of the wireframe or laser-cut frame portion). In some implementations, the septal anchoring element 236 (e.g., leaflet brace or the like) is a lower anchoring element configured to engage subannular tissue of the ventricle to aid in the securement of the valve 200 in the annulus. More specifically, the septal anchoring element 236 can be configured to engage subannular septal tissue, septal leaflet tissue, and/or any other suitable tissue at, near, and/or along the septum of the heart.

In some implementations, the proximal anchoring element 234 can be configured to transition between a first configuration in which the proximal anchoring element 234 is maintained in a compressed, undeployed, and/or restrained state, to a second configuration in which the proximal anchoring element 234 is expanded, extended, deployed, and/or unrestrained. More specifically, the proximal anchoring element 234 when in the first configuration can be maintained in a first position that is in contact with, adjacent to, and/or otherwise near the transannular section 250 of the valve frame 210, and when in the second configuration, can be released to a second position that extends away from the transannular section 250 of the frame 210. Said another way, the second position proximal anchoring element 234 can be further from the transannular section 250 than the first position of the proximal anchoring element 234.

In some embodiments, the valve 200 and/or the frame 210 can include a feature, member, mechanism, etc. configured to at least temporarily retain the proximal anchoring element 234 in the first configuration. For example, as shown in FIG. 6, the valve 200 and/or the frame 210 can include a tensile member configured to selectively engage the proximal anchoring element 234 to temporarily maintain the proximal anchoring element 234 in the first configuration. The tensile member can be any suitable shape, size, and/or configuration. For example, the tensile member can be an anchor, loop, tab, latch, hook, tether, elastomeric band, threaded coupler, ball and cup mechanism, and/or any other suitable removable attachment. The tensile member can removably couple to a portion of the proximal anchoring element 234 and can exert a force (e.g., a tensile or compression force) operable in maintaining the proximal anchoring element 234 in the first configuration. The tensile member can be reconfigurable allowing the tensile member to be disengaged from the proximal anchoring element 234, which in turn, can allow the proximal anchoring element 234 to transition from its first configuration to its second configuration, as described in further detail herein with reference to specific embodiments.

The flow control component 250 can refer in a non-limiting sense to a device for controlling fluid flow therethrough. In some embodiments, the flow control component 250 can be a leaflet structure having two, three, four, or more leaflets made of flexible biocompatible material such a treated or untreated pericardium. The flow control component 250 with leaflets can be sewn or joined to a support structure and/or can be sewn or joined to the frame 210. The flow control component 250 can be mounted within the frame 210 and configured to permit blood flow in a first direction through an inflow end of the valve and block blood flow in a second direction, opposite the first direction, through an outflow end of the valve. For example, the flow control component 250 can be configured such that the valve 200 functions, for example, as a heart valve, such as a tricuspid valve, mitral valve, aortic valve, or pulmonary valve, that can open to blood flowing during diastole from atrium to ventricle, and that can close from systolic ventricular pressure applied to the outer surface. Repeated opening and closing in sequence can be described as "reciprocating."

The flow control component 250 is contemplated to include a wide variety of (bio)prosthetic artificial valves, including ball valves (e.g., Starr-Edwards), bileaflet valves (St. Jude), tilting disc valves (e.g., Bjork-Shiley), stented pericardium heart-valve prosthesis' (bovine, porcine, ovine) (Edwards line of bioprostheses, St. Jude prosthetic valves), as well as homograft and autograft valves. Bioprosthetic pericardial valves can include bioprosthetic aortic valves, bioprosthetic mitral valves, bioprosthetic tricuspid valves, and bioprosthetic pulmonary valves. In some implementations, a suitable commercially available valve (flow control component 250) can be received or accepted by and/or otherwise mounted in the frame 210. Commercially available valves (flow control components 250) may include, for example, a Sapien, Sapien 3, or Sapien XT from Edwards Lifesciences, an Inspiris Resilia aortic valve from Edwards Lifesciences, a Masters HP 15 mm valve from Abbott, a Lotus Edge valve from Boston Scientific, a Crown PRT leaflet structure from Livanova/Sorin, a valve from the Carbomedics family of valves from Sorin, or other flow control component(s), or a flexible reciprocating sleeve or sleeve-valve.

In one embodiment, FIG. 6 is an illustration of a plan view of valve 200 with a septal anchoring or stability element 236 (e.g., arm, tab, extension, etc.), a distal anchoring element 232 (e.g., arm, tab, extension, etc.), and a proximal anchoring element 234 (e.g., arm, tab, extension, etc.), according to the invention. A guidewire coupler 233 is attached at the distal end of the distal anchor element 232 and provides one method of mounting and/or receiving the guidewire. The outer frame 210 is shown as an elliptic cylinder having the upper collar portion 220 (e.g., the supra-annular region), the lower sidewall portion 230 (e.g., the subannular region), and the transannular portion or region 212 disposed therebetween. The flow control component 250 (with leaflets mounted therein) is shown occupying a 25-35 mm diameter space within the elliptic cylinder of the outer frame 210 with a spacer panel 221 filling in the remaining space. In some embodiments, a catheter guide (not shown) can be attached at a proximal side of the upper collar portion 220 of the outer frame 210. The proximal anchoring element 234 is shown attached to a proximal end of the lower sidewall portion 230 of the outer frame 210. The septal anchoring element 236 is shown attached to a mid-point of the lower sidewall portion 230 of the outer frame 210 and extends in a septal direction or extends along the septal side of the lower sidewall portion 230 in a subannular direction.

Figure 7:
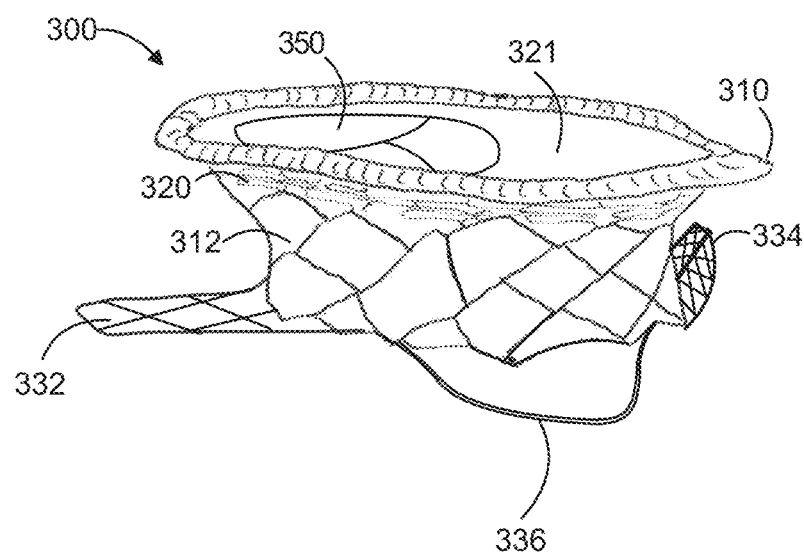
FIG. 7 is a distal-end side perspective view illustration of a side-deliverable transcatheter prosthetic valve having a valve frame with a septal area stability element, a distal anchoring element, and a proximal anchoring element, according to an embodiment.

FIG. 7 is a side perspective view illustration of a side-deliverable transcatheter prosthetic valve 300 (also referred to herein a "prosthetic valve" or simply "valve") according to an embodiment. The valve 300 has an outer frame 310, which is shown as an elliptic cylinder having an upper collar portion 320 (e.g., a supra-annular region) and a lower sidewall portion 330 (e.g., a subannular region). A flow control component 350 with prosthetic leaflets is shown occupying a portion (e.g., a 25-35 mm diameter space) within the elliptic cylinder of the outer frame 310 with a spacer panel 321 filling in the remaining space. The frame 310 is shown with a septal anchoring element 336, a distal anchoring element 332, and a proximal anchoring element 334 attached to a lower sidewall portion 330 of a transannular region 312 of the frame 310 (also referred to as a subannular region). A guidewire coupler 333 is attached at the distal end of the distal anchoring element 332 and provides one method of mounting and/or receiving a guidewire (not shown). In some embodiments, a catheter guide (not shown) can be attached at a proximal side of the upper collar portion 320 of the outer frame 310. The proximal anchoring element 334 is shown attached to the lower proximal sidewall portion 330 of the outer frame 310 and extends in a proximal direction. The septal anchoring element 336 is shown attached to a mid-point of the lower sidewall portion 330 and extends in a septal direction or extends along the septal side of the lower sidewall portion 330 in a subannular direction.

Figure 8:
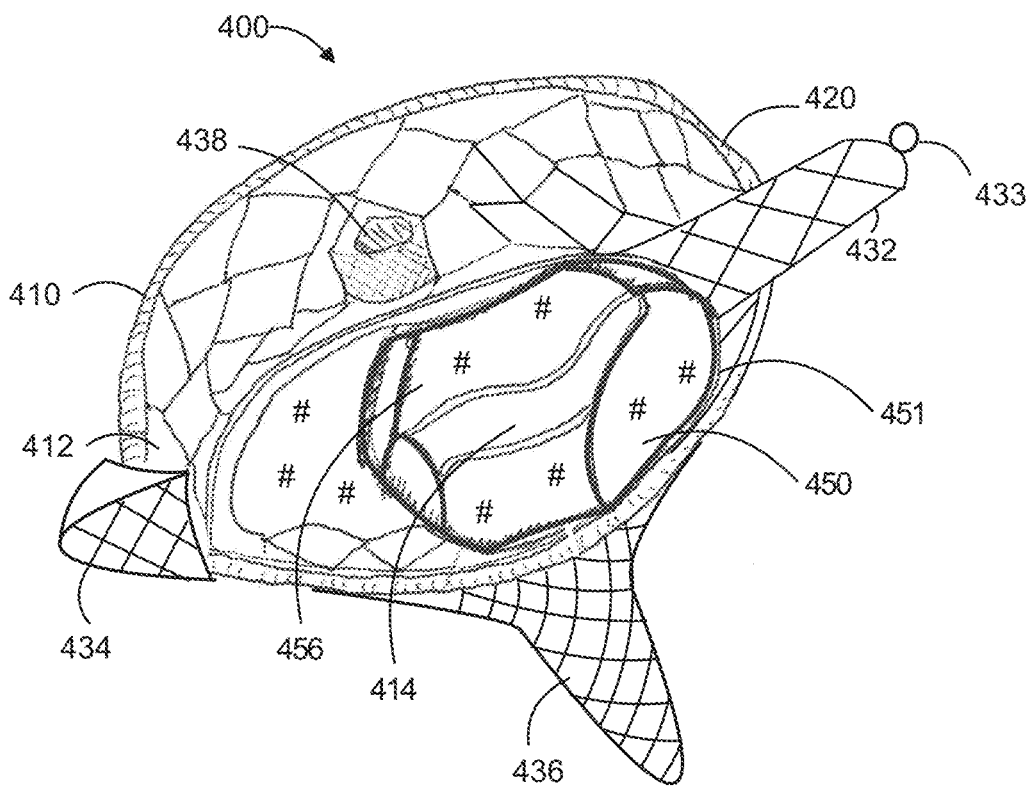
FIG. 8 is a postero-anterior underside perspective view illustration of a side-deliverable transcatheter prosthetic valve having a valve frame with a septal area stability element, a distal anchoring element, and a proximal anchoring element, according to an embodiment.

FIG. 8 is an underside view illustration of a side-deliverable transcatheter prosthetic valve 400 (also referred to herein a "prosthetic valve" or simply "valve") according to an embodiment. The valve 400 has an outer frame 410, which is shown as an elliptic cylinder having an upper collar portion 420 (e.g., a supra-annular region) and a lower sidewall portion 430 (e.g., a subannular region). A flow control component 450 is mounted within an aperture 414 defined by an interior of the frame 410. The flow control component 450 has leaflets 456 that are shown mounted on an inner leaflet frame 451. The frame 410 is shown with a septal anchoring element 436, a distal anchoring element 432, and a proximal anchoring element 434. A guidewire coupler 433 is attached at the distal end of the distal anchor element 432 and provides one method of mounting and/or receiving a guidewire (not shown). Another method of mounting the guidewire is configuring the distal anchor element 432 as a hollow tubular element. In some embodiments, a catheter guide (not shown) can be attached at a proximal side of the upper collar portion 420 (e.g., a supra-annular region) of the outer frame 410. The proximal anchoring element 434 is shown attached to the lower proximal sidewall portion 430 of the outer frame 410 and extends in a proximal direction. The septal anchoring element 436 is shown attached to a mid-point of the lower sidewall portion 430 and extends in a septal direction or extends along the septal side of the lower sidewall portion 430 in a subannular direction.

Figure 9:
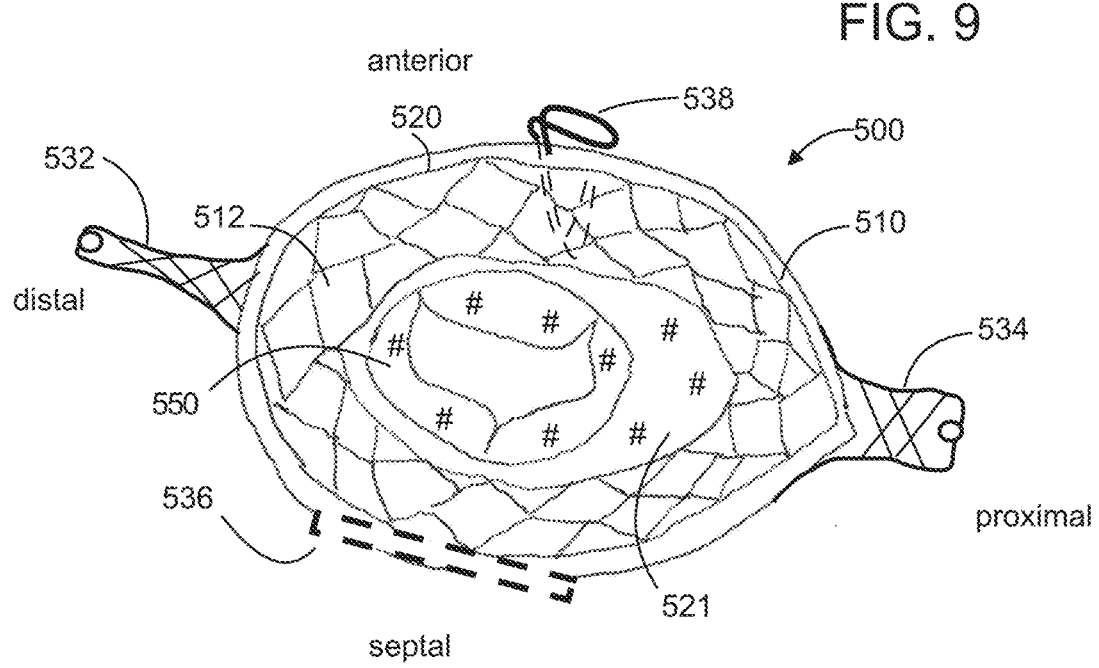
FIG. 9 is a topside perspective view illustration of a side-deliverable transcatheter prosthetic valve having a valve frame with a septal area stability element, a distal anchoring element, and a proximal anchoring element, according to an embodiment.

FIG. 9 is a top view illustration of a side-deliverable transcatheter prosthetic valve 500 (also referred to herein a "prosthetic valve" or simply "valve") according to an embodiment. The valve 500 has an outer frame 510, which is shown as an elliptic cylinder. A flow control component 550 with prosthetic leaflets is shown occupying a portion (e.g., a 25-35 mm diameter space) within the elliptic cylinder of the outer frame 510 with a spacer panel 521 filling in the remaining space. The frame 510 is shown with a septal anchoring element 536, a distal anchoring element 532, and a proximal anchoring element 534. In some embodiments, frame 510 can also include an anterior anchoring element 538 disposed on an anterior side of the frame 510 opposite the septal anchoring element 536. In some embodiments, a catheter guide (not shown) can be attached at a proximal side of an upper collar portion 520 (e.g., a supra-annular region) of the outer frame 510.

Figure 10:
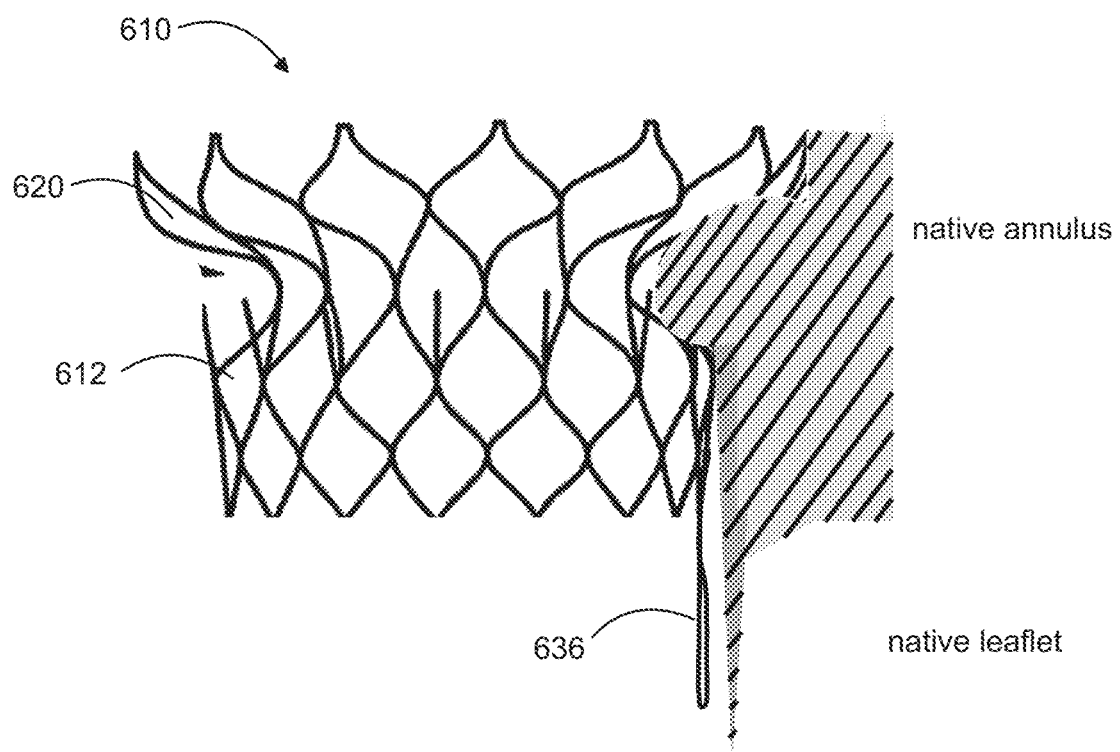
FIG. 10 is a side perspective view illustration of a wire frame for a side-deliverable transcatheter prosthetic valve highlighting a septal area stability element, according to an embodiment.

FIG. 10 is a side perspective view illustration of a wire frame 610 for a side-deliverable transcatheter prosthetic valve highlighting a septal stability and/or anchoring element 636, according to an embodiment. FIG. 10 shows an upper collar 620 (e.g., a supra-annular region) and a transannular frame sidewall 612 (e.g., a transannular region) of the wire frame 610. The septal stability and/or anchoring element 636 is shown abutting, for example, native septal tissue, septal side annular tissue, and/or septal leaflet tissue, which in turn, is blocked from interfering with the functioning of the leaflets of a flow control component (not shown) disposed in the valve frame 610.

Figure 11:
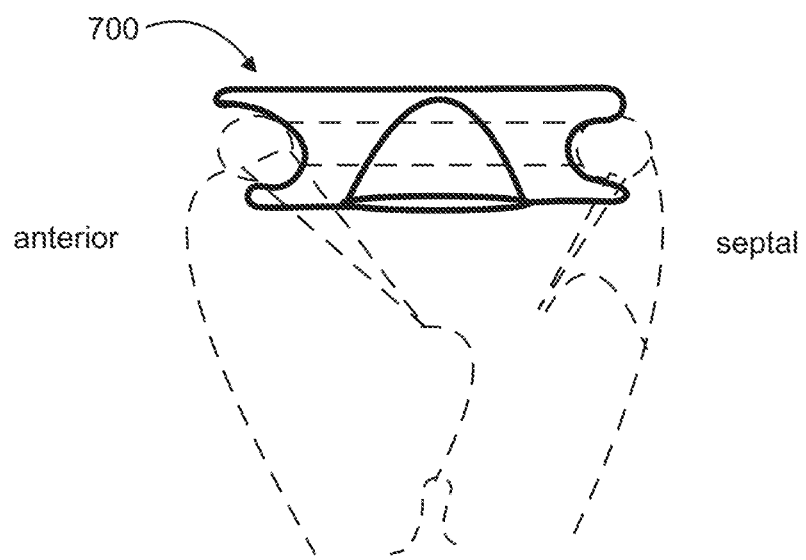
FIG. 11 is a side view illustration of a side-deliverable transcatheter prosthetic valve positioned in an annulus of a native tricuspid valve prior to stabilizing and/or anchoring the prosthetic valve according to an embodiment.
Figure 12:
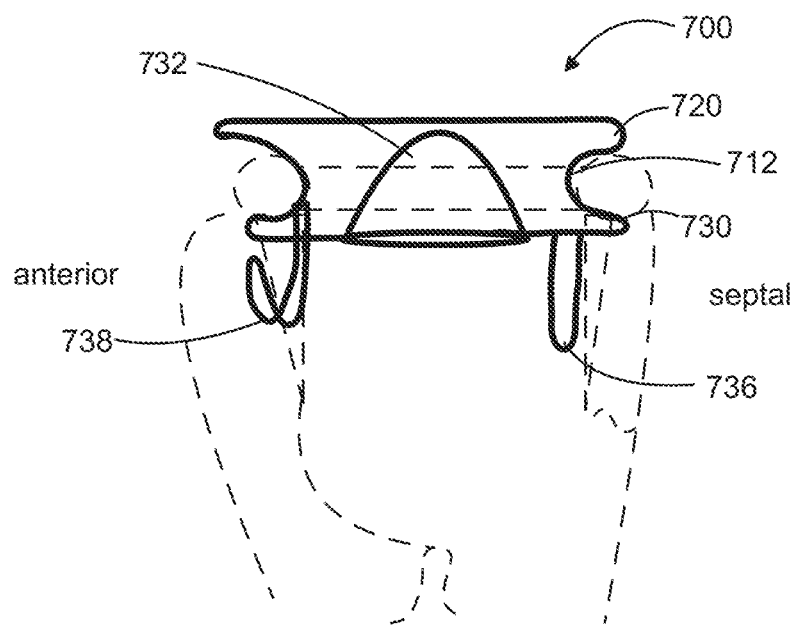
FIG. 12 is a side view illustration of the prosthetic valve of FIG. 11 positioned in the annulus of the native tricuspid valve showing a valve frame with at least a distal anchoring element, a septal area stability element, and an anterior anchoring element engaging native tissue to stabilize and/or anchor the prosthetic valve in the annulus.

FIGS. 11 and 12 are side view illustrations of a side-deliverable transcatheter prosthetic valve 700 (also referred to herein as "prosthetic valve" or simply "valve") according to an embodiment. FIG. 11 shows the prosthetic valve 700 positioned in an annulus of a native tricuspid valve prior to stabilizing and/or anchoring the prosthetic valve 700. FIG. 12 shows the prosthetic valve 700 with at least a distal anchoring element 732 that can anchor at least a distal portion of the valve 700 (e.g., in or at a ventricular outflow tract and/or the like). The prosthetic valve 700 is further shown with a septal anchoring element 736, and an anterior stability and/or anchoring element 738 engaging native septal tissue and native anterior tissue, respectively, to stabilize and/or anchor the prosthetic valve 700 in the annulus.

Figure 13:
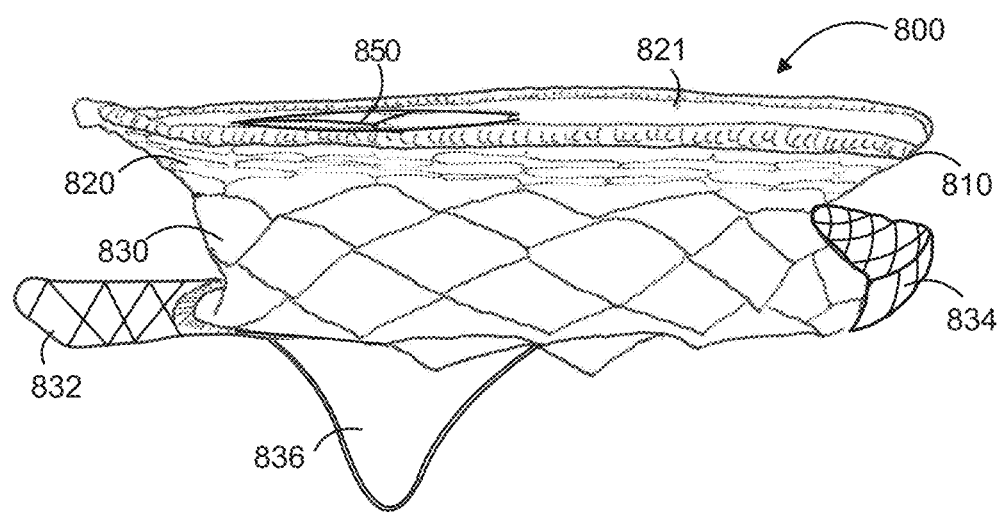
FIG. 13 is a side perspective view illustration of a side-deliverable transcatheter prosthetic valve having a valve frame with a distally located septal area stability element, a distal anchoring element, and a proximal anchoring element, according to an embodiment.

FIG. 13 is a side perspective view illustration of a side-deliverable transcatheter prosthetic valve 800 (also referred to herein as "prosthetic valve" or simply "valve") according to an embodiment. The valve 800 has an outer frame 810, which is shown as an elliptic cylinder having an upper collar portion 820 (e.g., a supra-annular region) and a lower sidewall portion 830 (e.g., a subannular region). A flow control component 850 with prosthetic leaflets is shown occupying a portion (e.g., a 25-35 mm diameter space) within the elliptic cylinder of the outer frame 810 with a spacer panel 821 filling in the remaining space. The frame 810 is shown having a distally located septal anchoring element 836, a distal anchoring element 832, and a proximal anchoring element 834. In some implementations, the distally located septal anchoring element 836 (e.g., a brace and/or the like) may be indicated for treating specific anatomical structures.

Figure 14:
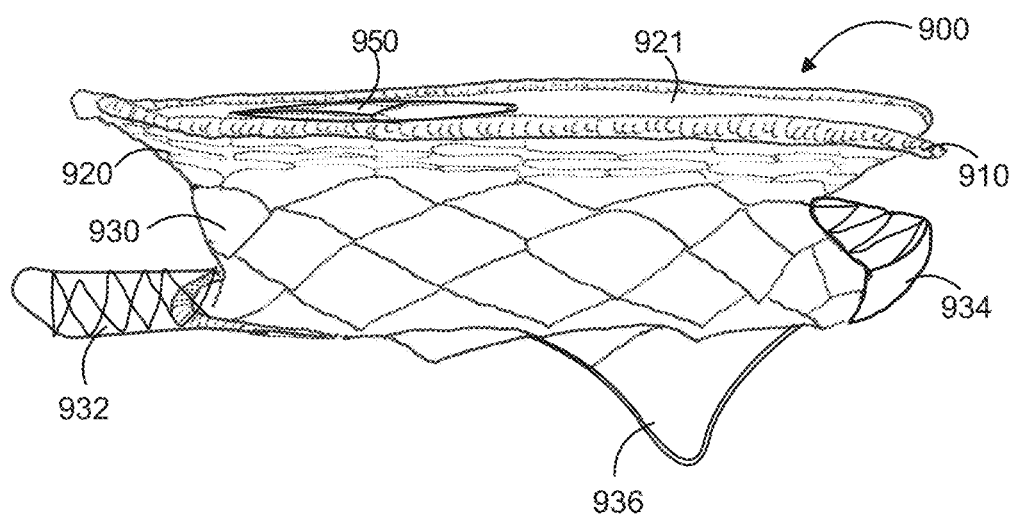
FIG. 14 is a side perspective view illustration of a side-deliverable transcatheter prosthetic valve having a valve frame with a proximally located septal area stability element, a distal anchoring element, and a proximal anchoring element, according to an embodiment.

FIG. 14 is a side perspective view illustration of a side-deliverable transcatheter prosthetic valve 900 (also referred to herein as "prosthetic valve" or simply "valve") according to an embodiment. The valve 900 has an outer frame 910, which is shown as an elliptic cylinder having an upper collar portion 920 (e.g., a supra-annular region) and a lower sidewall portion 930 (e.g., a subannular region). A flow control component 950 with prosthetic leaflets is shown occupying a portion (e.g., a 25-35 mm diameter space) within the elliptic cylinder of the outer frame 910 with a spacer panel 921 filling in the remaining space. The frame 910 is shown having a proximally located septal anchoring element 936, a distal anchoring element 932, and a proximal anchoring element 934. In some implementations, the proximally located septal anchoring element 936 may be indicated for avoiding interference with native electrical tissue or with the coronary sinus return.

Figure 15:
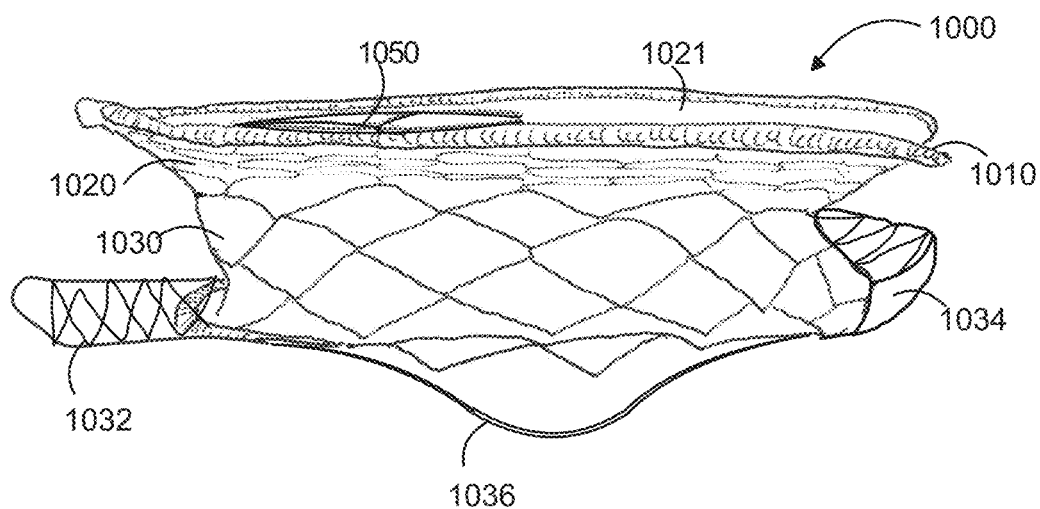
FIG. 15 is a side perspective view illustration of a side-deliverable transcatheter prosthetic valve having a valve frame with a shortened centrally located septal area stability element, a distal anchoring element, and a proximal anchoring element, according to an embodiment.

FIG. 15 is a side perspective view illustration of a side-deliverable transcatheter prosthetic valve 1000 (also referred to herein as "prosthetic valve" or simply "valve") according to an embodiment. The valve 1000 has an outer frame 1010, which is shown as an elliptic cylinder having an upper collar portion 1020 (e.g., a supra-annular region) and a lower sidewall portion 1030 (e.g., a subannular region). A flow control component 1050 with prosthetic leaflets is shown occupying a portion (e.g., a 25-35 mm diameter space) within the elliptic cylinder of the outer frame 1010 with a spacer panel 1021 filling in the remaining space. The frame 1010 is shown having a shortened (relatively shallow) centrally located septal anchoring element 1036, a distal anchoring element 1032, and a proximal anchoring element 1034. In some implementations, the shallow septal anchoring element 1036 (e.g., a brace and/or the like) may be indicated for avoiding excessive cutting effect on the ventricular tissue.

Figure 16:
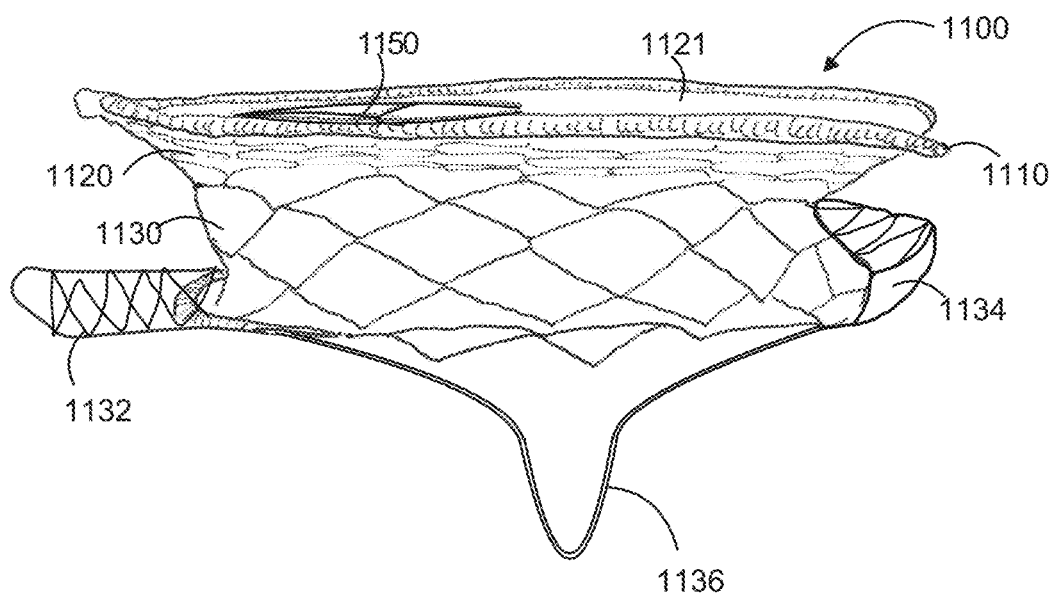
FIG. 16 is a side perspective view illustration of a side-deliverable transcatheter prosthetic valve having a valve frame with an extended-depth septal area stability element, a distal anchoring element, and a proximal anchoring element, according to an embodiment.

FIG. 16 is a side perspective view illustration of a side-deliverable transcatheter prosthetic valve 1100 (also referred to herein as "prosthetic valve" or simply "valve") according to an embodiment. The valve 1100 has an outer frame 1110, which is shown as an elliptic cylinder having an upper collar portion 1120 (e.g., a supra-annular region) and a lower sidewall portion 1130 (e.g., a subannular region). A flow control component 1150 with prosthetic leaflets is shown occupying a portion (e.g., a 25-35 mm diameter space) within the elliptic cylinder of the outer frame 1110 with a spacer panel 1121 filling in the remaining space. The frame 1110 is shown having an extended-depth, centrally located septal anchoring element 1136, a distal anchoring element 1132, and a proximal anchoring element 1134. In some implementations, the extended septal anchoring element 1136 (e.g., a brace and/or the like) may be indicated in treatment to block additional tissue from interfering with the functioning of the prosthetic valve 1100 and/or to provide additional ventricular stability to prevent unwanted movement of the prosthetic valve 1100 prior to in-growth, such as rolling, tilting, or other unwanted migration of the implant.

Figure 17:
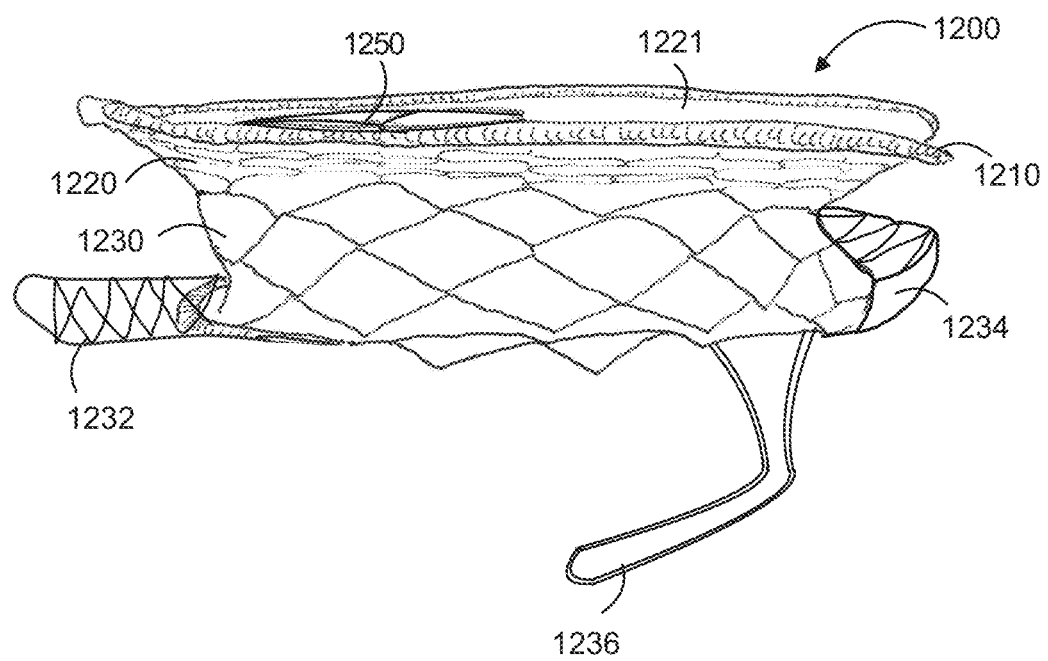
FIG. 17 is a side perspective view illustration of a side-deliverable transcatheter prosthetic valve having a valve frame with an asymmetric-shaped septal area stability element, a distal anchoring element, and a proximal anchoring element, according to an embodiment.

FIG. 17 is a side perspective view illustration of a side-deliverable transcatheter prosthetic valve 1200 (also referred to herein as "prosthetic valve" or simply "valve") according to an embodiment. The valve 1200 has an outer frame 1210, which is shown as an elliptic cylinder having an upper collar portion 1220 (e.g., a supra-annular region) and a lower sidewall portion 1230 (e.g., a subannular region). A flow control component 1250 with prosthetic leaflets is shown occupying a portion (e.g., a 25-35 mm diameter space) within the elliptic cylinder of the outer frame 1210 with a spacer panel 1221 filling in the remaining space. The frame 1210 is shown having an asymmetric-shaped septal anchoring element 1236, a distal anchoring element 1232, and a proximal anchoring element 1234. In some implementations, the asymmetrical septal anchoring element 1236 (e.g., a brace and/or the like) may be indicated for avoiding interference with native electrical tissue or with the coronary sinus return.

Figure 18:
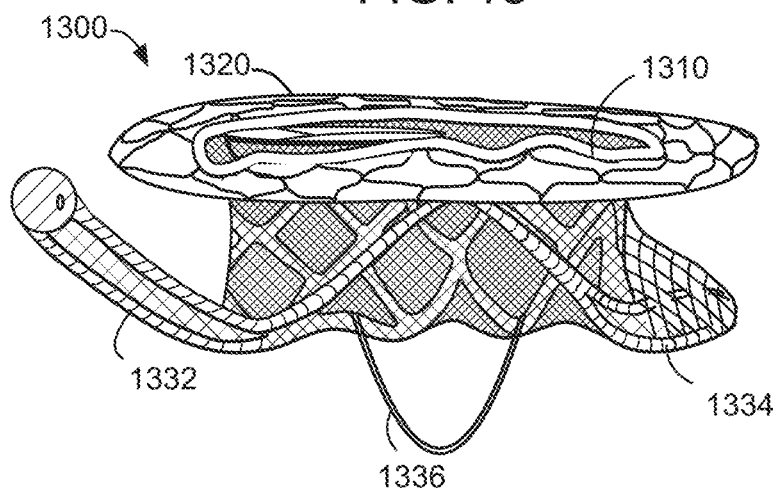
FIG. 18 is a side perspective view illustration of a wire-braid framed transcatheter prosthetic valve having a valve frame with a septal area stability element, a distal anchoring element, and a proximal anchoring element, according to an embodiment.

FIG. 18 is a side perspective view illustration of a side-deliverable transcatheter prosthetic valve 1300 having a wire-braid frame 1310, a septal anchoring element 1336, a distal anchoring element 1332, and a proximal anchoring element 1334, according to an embodiment. In some embodiments, the septal anchoring element 1336 can be formed by a portion of the wire-braid frame 1310 and can extend away from an atrial collar 1320 (e.g., a supra-annular region) of the frame 1310. The septal anchoring element 1336 can have any suitable configuration indicated, in some implementations, for treating specific anatomical structures, avoiding interference with native electrical tissue or with the coronary sinus return, avoiding excessive cutting effect on the ventricular tissue, blocking native tissue from interfering with the functioning of the prosthetic valve 1300 (e.g., leaflets of a flow control component), providing additional ventricular stability to prevent unwanted movement of the prosthetic valve 1300 prior to in-growth, such as rolling, tilting, or other unwanted migration of the implant, and/or the like.

Figure 19:
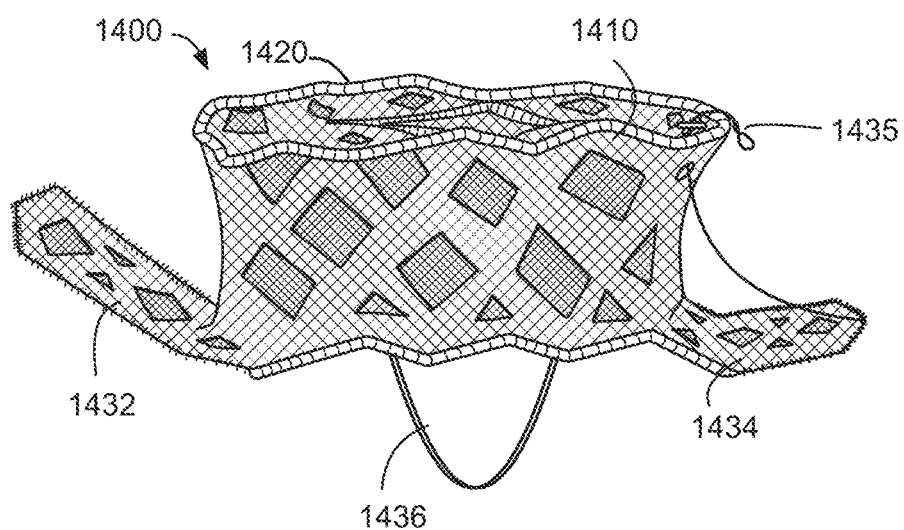
FIG. 19 is a side perspective view illustration of a laser-cut framed transcatheter prosthetic valve having a valve frame with a septal area stability element, a distal anchoring element, and a proximal anchoring element, according to an embodiment.

FIG. 19 is a side perspective view illustration of a side-deliverable transcatheter prosthetic valve 1400 having a laser-cut frame 1410, a septal anchoring element 1436, a distal anchoring element 1432, and a proximal anchoring element 1434, according to an embodiment. A tensile member 1435 is shown, which can be used to release and/or to otherwise facilitate the release of the proximal anchoring element 1434 from its compressed (first) configuration to its expanded (second) configuration. In some embodiments, the septal anchoring element 1436 can be formed by a portion of the wire-braid frame 1410 and can extend away from an atrial collar 1420 (e.g., a supra-annular region) of the frame 1410. The septal anchoring element 1436 can have any suitable configuration indicated, in some implementations, for treating specific anatomical structures, avoiding interference with native electrical tissue or with the coronary sinus return, avoiding excessive cutting effect on the ventricular tissue, blocking native tissue from interfering with the functioning of the prosthetic valve 1400 (e.g., leaflets of a flow control component), providing additional ventricular stability to prevent unwanted movement of the prosthetic valve 1400 prior to in-growth, such as rolling, tilting, or other unwanted migration of the implant, and/or the like.

Figure 20:
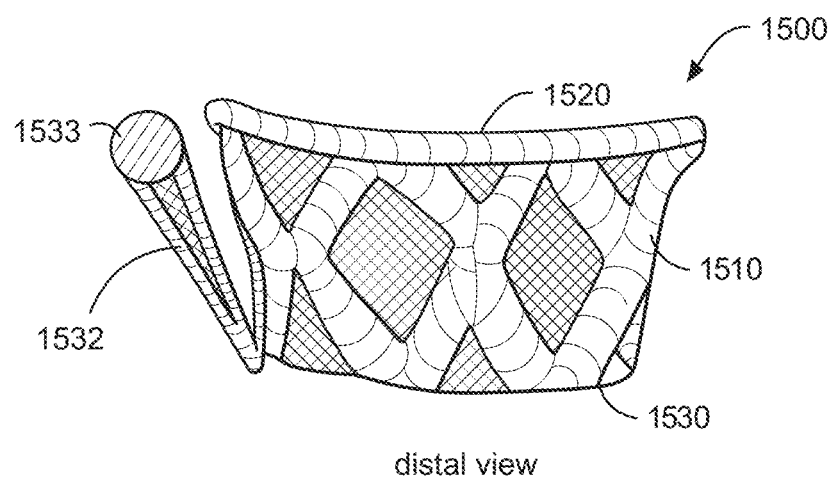
FIGS. 20 and 21 are a proximal side view illustration and a distal side view illustration, respectively, of a side-deliverable transcatheter prosthetic valve having a valve frame with a septal area stability element, a distal anchoring element (FIG. 21), and a proximal anchoring element (FIG. 20), according to an embodiment.
Figure 21:
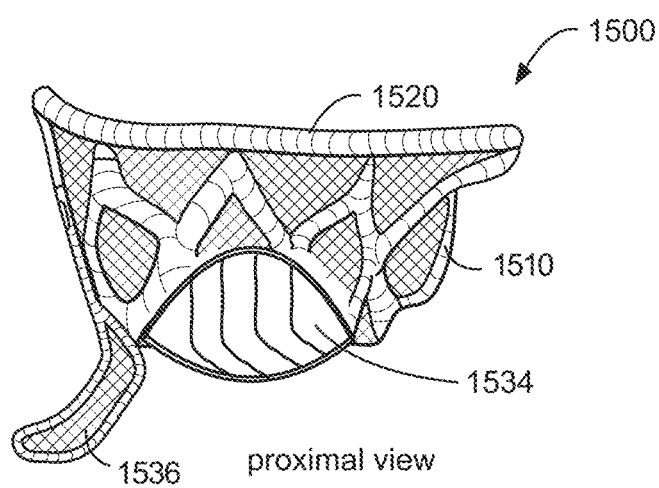

FIGS. 20 and 21 are a distal side view illustration and a proximal side view illustration, respectively, of a side-deliverable transcatheter prosthetic valve 1500 (also referred to herein as "prosthetic valve" or simply "valve") according to an embodiment. The valve 1500 has an outer frame 1510, which is shown as an elliptic cylinder having an upper collar portion 1520 (e.g., a supra-annular region) and a lower sidewall portion 1530 (e.g., a subannular region). A flow control component with prosthetic leaflets (not shown) can be mounted within the elliptic cylinder of the outer frame 1510. The frame 1510 is shown having a septal anchoring element 1536, a distal anchoring element 1532, and a proximal anchoring element 1534. FIG. 20 shows the distal anchoring element 1532 extending away from an annular support frame 1510 of the valve 1500. The distal anchoring element 1532 is shown with a guidewire coupler 1533 configured to at least temporarily couple to and/or otherwise receive a guidewire to facilitate delivery of the valve 1500 into an annulus of a native valve.

FIG. 21 shows the proximal anchoring element 1534 having an upper parabolic arch support member and a lower parabolic arch support member, with a flexible spacer fabric or structured-fabric stretched between the upper and lower arch supports. The lower arch support can rotate about its end portions, whereby in a stowed, or up position, the lower arch support is coextensive with the upper arch support (i.e. both lie atop one another with the parabolic opening facing down). A tensile member (not shown) can be used to hold the lower arch support in a stowed, upper position until the tensile member is released (e.g., holds the proximal anchoring element 1534 in its compressed (first) configuration). When the tensile member is released, the lower arch support rotates downward from shape-memory effect, pulling the flexible structured fabric taut and placing the proximal anchoring element 1534 in its expanded (second) configuration such that the lower arch support lays under the native annulus and the taut fabric substantially form fits the native annular and/or subannular tissue.

FIG. 21 further shows the septal anchoring element 1536 configured as an integrated tab, arm, extension, and/or the like of the frame 1510. The septal anchoring element 1536 is disposed along a septal side of the lower sidewall portion 1530 and adjacent to and/or otherwise near the proximal anchoring element 1534. Said another way, the septal anchoring element 1536 is proximally located.

Referring now to FIG. 22, a flowchart is shown illustrating a method 10 of deploying a prosthetic heart valve in an annulus of a native valve of a heart of a patient, according an embodiment. The prosthetic heart valve can be, for example, a side-deliverable transcatheter prosthetic heart valve such as any of those described herein. The prosthetic heart valve is transitionable between a first, compressed configuration for side-delivery via a delivery catheter and a second, expanded configuration for deployment into the annulus of the native valve. As described above, the native valve can be any of the valves of the heart. In some implementations, for example, the native valve is one of the tricuspid valve or the mitral valve. In some embodiments, for example, the prosthetic heart valve can include a frame and a flow control component mounted within a central channel of the frame. The flow control component is configured to permit blood flow in a first direction through the prosthetic heart valve from an inflow end to an outflow end and to block blood flow in a second direction, opposite the first direction. The frame can include, for example, at least a supra-annular region or collar and a transannular region coupled to the supra-annular region and extending in a perpendicular relative to a plane associated with and/or at least partially across the supra-annular region. In some implementations, a lower portion of the transannular region can form and/or include a subannular region of the frame. In some implementations, the subannular region is separate from the transannular region and coupled thereto in a manner similar to the coupling of the transannular region to the supra-annular region. The subannular region of the frame includes, forms, and/or is coupled to at least a distal anchoring element, a proximal anchoring element, and a septal anchoring element. In some embodiments, each of the distal anchoring element, the proximal anchoring element, and the septal anchoring element can be at least one of a wire loop, a wire frame, a laser cut frame, an integrated frame section, or a stent, and can extend from the subannular region a desired distance (e.g., about 10-40 mm).

The method 10 includes disposing in the atrium of the heart a distal end of a delivery catheter having disposed in a lumen thereof the prosthetic heart valve in the compressed configuration, at 11. For example, for tricuspid valve or pulmonary valve replacement, the atrium can be accessed, for example, through the inferior vena cava (IVC) via the femoral vein or through the superior vena cava (SVC) via the jugular vein. As another example, for mitral valve the atrium can be accessed through a trans-atrial approach (e.g., fossa ovalis or lower), via the IVC-femoral or the SVC jugular approach. When the distal end of the delivery catheter is disposed in a desired position in the atrium of the heart, the prosthetic valve in the compressed configuration can be advanced (e.g., along a guidewire) through the lumen of the delivery catheter. As described above, the prosthetic heart valve can be a side-deliverable prosthetic heart valve such that an axis extending through the inflow end and the outflow end of the prosthetic heart valve is substantially orthogonal to a lengthwise axis extending through the lumen of the delivery catheter. Said another way a longitudinal axis extending through the prosthetic valve is substantially parallel to the lengthwise axis extending through the lumen of the delivery catheter, as described in detail above with reference to the valve 100.

The prosthetic heart valve is released from the lumen of the delivery catheter such that the prosthetic heart valve transitions from the compressed configuration to the expanded configuration, at 12. In some implementations, the prosthetic heart valve can be advanced through the delivery catheter such that the distal anchoring element is distal to the remaining portions of the valve and thus, is first released from the distal end of the delivery catheter. As the prosthetic valve is further advances, the valve and/or at least the valve frame is allowed to expand (e.g., it is no longer constrained by the inner surface of the delivery catheter. In some implementations, the prosthetic valve can be in its expanded configuration when the prosthetic valve is completely released or otherwise outside of the delivery catheter (e.g., disposed in the atrium of the heart).

In some implementations, at least a portion of the prosthetic valve can be inserted into the annulus of the native valve while portions of the prosthetic valve are still being released from the delivery catheter. For example, for tricuspid valve replacement, the distal anchoring element can be inserted through the annulus and into a right ventricular outflow track (RVOT) as the prosthetic valve is released from the delivery catheter. As another example, for mitral valve replacement, the distal anchoring element can be inserted through the annulus and into a subannular position distal to the annulus as the prosthetic valve is released from the delivery catheter.

At least a portion of the prosthetic heart valve is seated in the annulus of the native valve, at 13. In some implementations, the seating of the prosthetic valve in the annulus can include inserting the proximal anchoring element and the septal anchoring element into and/or through the annulus prior to or as the prosthetic valve is being seated in the annulus. In addition, the method 10 includes placing the septal anchoring element in contact with at least one of a native septal wall or a septal leaflet area to stabilize the prosthetic heart valve in the annulus when the prosthetic heart valve is seated in the annulus, at 14. For example, the septal anchoring element can stabilize the prosthetic heart valve against at least one of intra-annular rolling forces or intra-annular twisting forces within the annulus during deployment or seating of the valve in the annulus or after the valve is deployed and/or secured in the annulus.

In some implementations, seating the prosthetic valve in the annulus is such that the proximal anchoring element is placed in contact with subannular tissue on the proximal side of the annulus. In some implementations, the proximal anchoring element is configured to transition from a first configuration to a second configuration after seating the prosthetic heart valve in the annulus to contact the proximal subannular tissue. In some implementations, the proximal anchoring element is transitioned from the first configuration to the second configuration by manipulating a tensile member coupled to the valve frame.

In some implementations, the septal anchoring element similarly can be configured to transition from a first configuration to a second configuration after the prosthetic valve in the annulus. In other implementations, the septal anchoring element can be an anchoring element having a single or substantially fixed configuration. The septal anchoring element can have any suitable configuration indicated, in some implementations, for treating specific anatomical structures, avoiding interference with native electrical tissue or with the coronary sinus return, avoiding excessive cutting effect on the ventricular tissue, blocking native tissue from interfering with the functioning of the prosthetic valve (e.g., leaflets of a flow control component), providing additional ventricular stability to prevent unwanted movement of the prosthetic valve prior to in-growth, such as rolling, tilting, or other unwanted migration of the implant, and/or the like, as described above with reference to the septal anchoring elements described above with reference to specific embodiments.

While various embodiments have been described above, it should be understood that they have been presented by way of example only, and not limitation. Likewise, it should be understood that the specific terminology used herein is for the purpose of describing particular embodiments and/or features or components thereof and is not intended to be limiting. Various modifications, changes, and/or variations in form and/or detail may be made without departing from the scope of the disclosure and/or without altering the function and/or advantages thereof unless expressly stated otherwise. Functionally equivalent embodiments, implementations, and/or methods, in addition to those enumerated herein, will be apparent to those skilled in the art from the foregoing descriptions and are intended to fall within the scope of the disclosure.

Where schematics and/or embodiments described above indicate certain components arranged in certain orientations or positions, the arrangement of components may be modified. Although various embodiments have been described as having particular features and/or combinations of components, other embodiments are possible having a combination of any features and/or components from any of embodiments described herein, except mutually exclusive combinations. The embodiments described herein can include various combinations and/or sub-combinations of the functions, components, and/or features of the different embodiments described.

Where methods described above indicate certain events occurring in certain order, the ordering of certain events may be modified. Additionally, certain of the events may be performed concurrently in a parallel process when possible, as well as performed sequentially as described above. While methods have been described as having particular steps and/or combinations of steps, other methods are possible having a combination of any steps from any of methods described herein, except mutually exclusive combinations and/or unless the context clearly states otherwise.

What is claimed is:

1. A side-deliverable prosthetic heart valve, the prosthetic heart valve comprising:
   a valve frame having a transannular section and supraannular section attached around a top edge of the transannular section and defining an aperture extending along a central axis of the valve frame, the transannular section including a plurality of wire cells having a geometry and orientation that allows compression of the valve frame along at least the central axis, the valve frame including a distal subannular anchoring element, a proximal subannular anchoring element, and a septal subannular anchoring element, the septal subannular anchoring element being asymmetric relative to an anteroposterior (AP) plane, at least a portion of the septal subannular anchoring element extending proximal to the AP plane; and
   a flow control component mounted within the aperture and configured to permit blood flow along the central axis in a first direction from an inflow end to an outflow end of the flow control component and block blood flow in a second direction, opposite the first direction,
   the prosthetic heart valve in an expanded configuration having a first height along the central axis, a first lateral width along a lateral axis perpendicular to the central axis, and a longitudinal length along a longitudinal axis perpendicular to the central axis and the lateral axis, the prosthetic heart valve in a compressed configuration having a second height along the central axis less than the first height and a second lateral width along the lateral axis less than the first lateral width,
   the prosthetic heart valve being placed in the compressed configuration for side-delivery to a heart of a patient via a delivery catheter, the prosthetic heart valve being transitionable from the compressed configuration to the expanded configuration when the prosthetic heart valve is released from the delivery catheter, the prosthetic heart valve configured to be seated in an annulus of a native valve of the heart when in the expanded configuration, the distal subannular anchoring element, the proximal subannular anchoring element, and the septal subannular anchoring element configured to be inserted through the annulus of the native valve prior to the prosthetic heart valve being seated therein, the septal subannular anchoring element is configured to extend below the annulus and contact ventricular septal tissue to stabilize the prosthetic heart valve in the annulus when the prosthetic heart valve is seated in the annulus.

2. The prosthetic heart valve of claim 1, wherein the distal subannular anchoring element is configured to engage ventricular tissue distal to the annulus when the prosthetic heart valve is seated in the annulus and the proximal subannular anchoring element is configuration to engage ventricular tissue proximal to the annulus when the prosthetic heart valve is seated in the annulus.

3. The prosthetic heart valve of claim 1, wherein the ventricular septal tissue is at least one of a septal wall of the heart or a septal leaflet area of the heart.

4. The prosthetic heart valve of claim 3, wherein the septal subannular anchoring element is configured to stabilize the prosthetic heart valve against at least one of intra-annular rolling forces or intra-annular twisting forces within the annulus.

5. The prosthetic heart valve of claim 1, wherein seating the prosthetic heart valve in the annulus of the native valve includes positioning the distal subannular anchoring element in a ventricular outflow tract before the prosthetic heart valve is seated in the annulus of the native valve.

6. The prosthetic heart valve of claim 1, wherein the distal subannular anchoring element includes a guidewire coupler that is configured to be temporarily coupled to a guidewire.

7. The prosthetic heart valve of claim 1, wherein the distal subannular anchoring element is at least one of a wire loop, a wire frame, an integrated frame section, or a stent, the proximal subannular anchoring element is at least one of a wire loop, a wire frame, an integrated frame section, or a stent, and the septal subannular anchoring element is at least one of a wire loop, a wire frame, an integrated frame section, or a stent.

8. The prosthetic heart valve of claim 1, wherein the proximal subannular anchoring element is configured to be transitioned from a first configuration to a second configuration after the prosthetic heart valve is seated in the annulus of the native valve.

9. The prosthetic heart valve of claim 8, further comprising:

a tensile member coupled to the valve frame, the tensile member having a first configuration in which the tensile member is engaged with the proximal subannular anchoring element to maintain the proximal subannular anchoring element in the first configuration, and a second configuration in which the tensile member is disengaged from the proximal subannular anchoring element to allow the proximal subannular anchoring element to transition to the second configuration.

10. A side-deliverable prosthetic heart valve, the prosthetic heart valve comprising:

a valve frame having a transannular section and supra-annular section attached around a top edge of the transannular section, the transannular section including a plurality of wire cells having a geometry and orientation that allows compression of the valve frame along at least the central axis;

a distal subannular anchoring element coupled to the transannular section of the valve frame;

a proximal subannular anchoring element coupled to the transannular section of the valve frame;

a septal subannular anchoring element coupled to the transannular section of the valve frame, the septal subannular anchoring element being asymmetric relative to an anteroposterior (AP) plane, at least a portion of the septal subannular anchoring element extending proximal to the AP plane; and a flow control component mounted within an aperture extending along a central axis of the valve frame and configured to permit blood flow along the central axis in a first direction through the prosthetic heart valve from an inflow end to an outflow end and to block blood flow in a second direction, opposite the first direction, the prosthetic heart valve having a compressed configuration for introduction into a heart of a patient via a delivery catheter in which the central axis is substantially orthogonal to a lengthwise axis extending through a lumen of the delivery catheter, the prosthetic heart valve having an expanded configuration when the prosthetic heart valve is released from the delivery catheter into the heart, the prosthetic heart valve configured to be seated in a annulus of a native valve of the heart when in the expanded configuration, the distal subannular anchoring element configured to be disposed in a ventricular outflow tract when the prosthetic heart valve is seated in the annulus, the proximal subannular anchoring element configured to be disposed in a proximal subannular area when the prosthetic heart valve is seated in the annulus, and the septal subannular anchoring element is configured to extend below the annulus and contact at least one of a native septal wall or a native septal leaflet when the prosthetic heart valve is seated in the annulus.

11. The prosthetic heart valve of claim 10, wherein each of the distal subannular anchoring element, the proximal subannular anchoring element, and the septal subannular anchoring element is coupled to a lower edge of the transannular section.

12. The prosthetic heart valve of claim 10, wherein the native valve is a native mitral valve and the ventricular outflow tract is a subannular position distal to the annulus.

13. The prosthetic heart valve of claim 1, wherein the longitudinal axis is parallel to a lengthwise axis extending through the lumen of the delivery catheter during delivery of the prosthetic heart valve.

14. The prosthetic heart valve of claim 10, wherein the native valve is a native tricuspid valve and the ventricular outflow tract is a right ventricular outflow track (RVOT).

15. The prosthetic heart valve of claim 10, wherein the septal subannular anchoring element is configured to stabilize the prosthetic heart valve against at least one of intra-annular rolling forces or intra-annular twisting forces within the annulus.

16. The prosthetic heart valve of claim 10, wherein the distal subannular anchoring element is at least one of a wire loop, a wire frame, a laser cut frame, an integrated frame section, or a stent, the proximal subannular anchoring element is at least one of a wire loop, a wire frame, an integrated frame section, or a stent, and the septal subannular anchoring element is at least one of a wire loop, a wire frame, an integrated frame section, or a stent.

17. The prosthetic heart valve of claim 10, wherein the distal subannular anchoring element includes a guidewire coupler that is configured to be temporarily coupled to a guidewire.

18. The prosthetic heart valve of claim 10, wherein the proximal subannular anchoring element is configured to be transitioned from a first configuration to a second configuration after the prosthetic heart valve is seated in the annulus of the native valve.

19. The prosthetic heart valve of claim 18, further comprising:
a tensile member coupled to the valve frame, the tensile member having a first configuration in which the tensile member is engaged with the proximal subannular anchoring element to maintain the proximal subannular anchoring element in the first configuration, and a second configuration in which the tensile member is disengaged from the proximal subannular anchoring element to allow the proximal subannular anchoring element to transition to the second configuration.

20. A method of deploying a side-deliverable prosthetic heart valve in an annulus of a native valve of a heart of a patient, the method comprising:
disposing in the atrium of the heart a distal end of a delivery catheter having disposed in a lumen thereof the prosthetic heart valve in a compressed configuration, the prosthetic heart valve having a valve frame with a transannular section, a supra-annular section attached around a top edge of the transannular section, a distal subannular anchoring element, a proximal subannular anchoring element, a septal subannular anchoring element, and a flow control component mounted within an aperture extending along a central axis of the valve frame, the transannular section including a plurality of wire cells having a geometry and orientation that allows compression of the valve frame along at least the central axis, the flow control component configured to permit blood flow along the central axis in a first direction through the prosthetic heart valve from an inflow end to an outflow end and to block blood flow in a second direction, opposite the first direction, the central axis being substantially orthogonal to a lengthwise axis extending through the lumen of the delivery catheter when the prosthetic valve is in the compressed configuration and disposed in the lumen of the delivery catheter;
releasing the prosthetic heart valve from the lumen of the delivery catheter such that the prosthetic heart valve transitions from the compressed configuration to an expanded configuration;
seating at least a portion of the prosthetic heart valve in the annulus of the native valve; and
placing the septal subannular anchoring element in contact with at least one of a native septal wall or a septal leaflet area to stabilize the prosthetic heart valve in the annulus when the prosthetic heart valve is seated in the annulus, the septal subannular anchoring element being asymmetric relative to an anteroposterior (AP) plane, at least a portion of the septal subannular anchoring element extending proximal to the AP plane.

21. The method of claim 20, wherein the septal subannular anchoring element is configured to stabilize the prosthetic heart valve against at least one of intra-annular rolling forces or intra-annular twisting forces within the annulus.

22. The method of claim 20, wherein the distal subannular anchoring element is at least one of a wire loop, a wire frame, a laser cut frame, an integrated frame section, or a stent,
the proximal subannular anchoring element is at least one of a wire loop, a wire frame, an integrated frame section, or a stent, and
the septal subannular anchoring element is at least one of a wire loop, a wire frame, an integrated frame section, or a stent.

23. The method of claim 20, wherein the native valve is a native mitral valve, the method further comprising:
placing the distal subannular anchoring element in a subannular position distal to the annulus.

24. The method of claim 20, wherein the native valve is a native tricuspid valve, the method further comprising:
placing the distal subannular anchoring element in a right ventricular outflow track (RVOT).

25. The method of claim 20, further comprising:
placing proximal subannular anchoring element in contact with proximal subannular tissue when the prosthetic heart valve is seated in the annulus.

26. The method of claim 20, wherein placing the proximal subannular anchoring element in contact with proximal subannular tissue includes transitioning the proximal subannular anchoring element from a first configuration to a second configuration after the seating the prosthetic heart valve in the annulus.

27. The method of claim 26, wherein transitioning the proximal subannular anchoring element from the first configuration to the second configuration includes manipulating a tensile member coupled to the valve frame to transition the proximal subannular anchoring element from the first configuration to the second configuration.

* * * * *